United States Patent
Zhu

(10) Patent No.: US 11,266,717 B2
(45) Date of Patent: Mar. 8, 2022

(54) DIAGNOSIS, PREVENTION, AND/OR TREATMENT OF AUTOIMMUNE DISEASES

(71) Applicant: IMMUNOWORK, LLC, North Hollywood, CA (US)

(72) Inventor: Quansheng Zhu, North Hollywood, CA (US)

(73) Assignee: IMMUNOWORK, LLC, North Hollywood, CA (US)

( * ) Notice: Subject to any disclaimer, the term of this patent is extended or adjusted under 35 U.S.C. 154(b) by 0 days.

(21) Appl. No.: 16/324,870

(22) PCT Filed: Aug. 11, 2017

(86) PCT No.: PCT/US2017/046626
§ 371 (c)(1),
(2) Date: Feb. 11, 2019

(87) PCT Pub. No.: WO2018/031947
PCT Pub. Date: Feb. 15, 2018

(65) Prior Publication Data
US 2019/0183969 A1 Jun. 20, 2019

Related U.S. Application Data

(60) Provisional application No. 62/374,382, filed on Aug. 12, 2016.

(51) Int. Cl.
| | |
|---|---|
| A61K 38/16 | (2006.01) |
| A61K 47/65 | (2017.01) |
| A61K 47/64 | (2017.01) |
| G01N 33/564 | (2006.01) |
| G01N 33/96 | (2006.01) |
| A61K 38/17 | (2006.01) |
| A61P 13/12 | (2006.01) |
| G01N 33/68 | (2006.01) |

(52) U.S. Cl.
CPC ............ *A61K 38/177* (2013.01); *A61K 38/16* (2013.01); *A61K 47/64* (2017.08); *A61K 47/65* (2017.08); *A61P 13/12* (2018.01); *G01N 33/564* (2013.01); *G01N 33/96* (2013.01); *G01N 33/68* (2013.01)

(58) Field of Classification Search
CPC ...... A61K 38/177; A61K 38/16; A61K 47/64; A61K 47/65; A61P 13/12; G01N 33/564; G01N 33/96; G01N 33/68
See application file for complete search history.

(56) References Cited

U.S. PATENT DOCUMENTS

| | | |
|---|---|---|
| 8,507,215 B2 | 8/2013 | Salant |
| 2007/0212733 A1 | 9/2007 | Martin |
| 2011/0177534 A1 | 7/2011 | Salant et al. |
| 2013/0280738 A1 | 10/2013 | Salant |
| 2014/0255346 A1 | 9/2014 | Kuerten |

FOREIGN PATENT DOCUMENTS

| | | | |
|---|---|---|---|
| CN | 105510575 | | 4/2016 |
| EP | 0365087 A1 | | 4/1990 |
| JP | 2009-517046 A | | 4/2009 |
| JP | 2011-528789 A | | 11/2011 |
| WO | WO 02/09649 A1 | | 2/2002 |
| WO | WO/2010/009457 | * | 1/2010 ........... G01N 33/564 |
| WO | WO 2010/009457 A1 | | 1/2010 |
| WO | WO 2015/004603 A1 | | 1/2015 |
| WO | WO 2015/185949 A1 | | 12/2015 |

OTHER PUBLICATIONS

Li et al., (2018) Diagnostic Test Accuracy of Serum Anti-PLA2R Autoantibodies and Glomerular PLA2R Antigen for Diagnosing Idiopathic Membranous Nephropathy: An Updated Meta-Analysis. Front. Med. 5:101. (Year: 2018).*
Schrezenmeier et al., J Am Soc Nephrol 29: 741-758, 2018. (Year: 2018).*
Goldmacher et al., Annual Reports in Medicinal Chemistry, vol. 47, Chapter 23, Elsevier Inc., (Year: 2012).*
Franz, B., et al., Ex vivo characterization and isolation of rare memory B cells with antigen tetramers, Immunobiology, vol. 118, No. 2, pp. 348-357, 2011.
Alewine, C., et al., Advances in Anticancer Immunotoxin Therapy, The Oncologist, vol. 20, pp. 176-185, 2015.
Beck, Jr., L.H., et al., M-Type Phospholipase A2 Receptor as Target Antigen in Idiopathic Membranous Nephropathy, The New England Journal of Medicine, vol. 361, No. 1, pp. 11-21, 2009.
Beck, Jr., L.H., et al., Rituximab-Induced Depletion of Anti-PLA$_2$R Autoantiboides Predicts Response in Membranous Nephropathy, Journal of American Society of Nephrology, vol. 22, pp. 1543-1550, 2011.
International Search Report and Written Opinion, dated Dec. 11, 2017, in International Application No. PCT/US2017/046626.
Kao, L., et al., Identification of the Immunodominant Epitope Region in Phospholipase A$_2$ Receptor Mediating Autoantibody Binding in Idiopathic Membranous Nephropathy, Journal of American Society of Nephrology, vol. 26, No. 2, pp. 291-301, 2015.
Ohyama, B., et al., Epitope Spreading Is Rarely Found in Pemphigus Vulgaris by Large-Scale Longitudinal Study Using Desmoglein 2-Based Swapped Molecules, Journal of Investigative Dermatology, vol. 132, pp. 1158-1168, 2012.

(Continued)

*Primary Examiner* — Kimberly Ballard
*Assistant Examiner* — Stacey N Macfarlane
(74) *Attorney, Agent, or Firm* — Knobbe, Martens, Olson & Bear LLP

(57) ABSTRACT

Compositions, methods, and kits are for the diagnosis, prevention and/or treatment of autoimmune diseases by detecting, targeting, and/or eliminating epitope-specific autoimmune cells. The compositions include a conjugate of an epitope and an agent that allows for detecting, targeting, and/or eliminating epitope-specific autoimmune cells.

23 Claims, 32 Drawing Sheets
Specification includes a Sequence Listing.

(56) References Cited

OTHER PUBLICATIONS

Pape, K.A., et al., The Humoral Immune Response Is Initiated in Lymph Nodes by B Cells that Acquire Soluble Antigen Directly in the Follicles, Immunity, vol. 26, pp. 491-502, 2007.

Roozendaal, R., et al., Conduits Mediate Transport of Low-Molecular-Weight Antigen to Lymph Node Follicles, Immunity, vol. 30, pp. 264-276, 2009.

Klose, D., et al., Novel fusion proteins for the antigenspecific staining and elimination of B cell receptor-positive cell populations demonstrated by a tetanus toxoid fragment C (TTC) model antigen, BMC Biotechnology, 16:18, 2016, 11 pages.

Bauer et al., Hepatitis B Surface Antigen-Specific T And B Cell Memory In Individuals Who Had Lost Protective Antibodies After Hepatitis B Vaccination, Vaccine, vol. 24, pp. 572-577, 2006.

Colucci et al., B Cell Reconstruction after Rituximab Treatment in Idiopathic Nephrotic Syndrome, Journal of the American Society of Nephrology, vol. 27, pp. 1811-1822, 2016.

D'Orsogna et al., Infectious Pathogens May Trigger Specific Allo-HLA Reactivity Via Multiple Mechanisms, Immunogenetics, vol. 69, pp. 631-641, 2017.

Extended European Search Report in European Application No. 17840379.9, dated Jan. 7, 2020.

Fresquet et al., Identification of a Major Epitope Recognized by PLA2R Autoantibodies in Primary Membranous Nephropathy, Journal of the American Society of Nephrology, vol. 26, pp. 302-313, 2015.

Han et al., Peripheral Blood B Cells Producing Donor-Specific HLA Antibodies In Vitro, Human Immunology, vol. 70, pp. 29-34, 2009.

Heidt et al., A Novel ELISPOT Assay To Quantify HLA-specific B cells in HLA-Immunized Individuals, American Journal of Transplantation, vol. 12, pp. 1469-1478, 2012.

Hoffman et al., Clinical Journal of the American Society of Nephrology: CJASN, Clinical Journal of the American Society of Nephrology, vol. 11, No. 1, pp. 137-154, 2016.

International Search Report and Written Opinion dated Dec. 11, 2017 in International Application No. PCT/US2017/46626.

Kanigicherla et al., Anti-PLA2R Antibodies Measured By Elisa Predict Long-Term Outcome In A Prevalent Population Of Patients With Idiopathic Membranous Nephropathy, Kidney International, vol. 83, pp. 940-948, 2013.

Kao et al., Identification of the immunodominant epitope region in phospholipase A2 receptor-mediating autoantibody binding in idiopathic membranous nephropathy, Journal of the American Society of Nephrology, Lippincott Williams & Wilkins, vol. 26, pp. 291-301, 2015.

Kurosaki et al., Memory B cells, Nature Reviews: Nature Reviews Immunology, vol. 15, pp. 149-159 2015.

Lucia et al., Preformed Circulating HLA-Specific Memory B Cells Predict High Risk Of Humoral Rejection In Kidney Transplantation, Kidney International, vol. 88, pp. 874-887, 2015.

Luque et al., Value of Monitoring Circulating Donor-Reactive Memory B Cells To Characterize Antibody-Mediated Rejection After Kidney Transplantation, American Journal of Transplantation, vol. 19, pp. 368-380, 2019.

Ma et al., The Role of Complement in Membranous Nephropathy, Seminars in Nephrology, vol. 33, No. 6, pp. 531-542, 2013.

Ronco et al., Pathophysiological Advances In Membranous Nephropathy: Time For A Shift In Patient's Care, LANCET, vol. 385, pp. 1983-1992, 2015.

Schrezenmeier et al., Targeting B Cells And Plasma Cells In Glomerular Diseases: Translational Perspectives, Journal Of The American Society Of Nephrology, vol. 29, pp. 741-758, 2018.

Macleod, et al., Antigen-based immunotherapy (AIT) for autoimmune and allergic disease, Current Opinion in Pharmacology, vol. 23, pp. 11-16, 2015.

Serra, et al., Antigen-specific therapeutic approaches for autoimmunity, Nature Biotechnology, vol. 37, pp. 238-251, 2019.

Office Action dated Jul. 11, 2021 received in Japanese Patent Application No. 2019-529463.

Office Action dated Sep. 29, 2021 received in Chinese Application No. 201780062647.9.

Goldmacher, Victor S. et al., "Antibody-Drug Conjugates for Targeted Cancer Therapy," Annual Reports in Medicinal Chemistry 47:349-366.

Office Action dated Dec. 15, 2021 in Chinese Patent Application No. 201780062647.9.

Proby, C.M., et al., "Development of Chimeric Molecules for Recognition and Targeting of Antigen-Specific V cells in Pemphigus Vulgaris," British Journal of Dermatology, 142: 321-330, 2000.

Zhai, Zhifang, "Effects of recombinant Dsg3EC1-2 chimeric toxin on peripheral blood T and B lymphocytes of pemphigus vulgaris" Chinese Doctoral and Master's Thesis Full-text Database, Medical and Health Science and Technology Series, Issue 1 E075-14, Mar. 15, 2005.

* cited by examiner

FIG. 6

MLLSPSLLLLLLLGAPRGCAEGVAAALTPERLLEWQDKGIFVIQSESLKKCI
QAGKSVLTLENCKQANKHMLWKWSNHGLFNIGGSGCLGLNFSAPEQP
LSLYECDSTLVSLRWRCNRKMITGPLQYSVQVAHDNTVVASRKYIHKWIS
YGSGGGDICEYLHKDLHTIKGNTHGMPCMFPFQYNHQWHHECTREGRE
DDLLWCATTSRYERDEKWGFCPDPTSAEVGCDTIWEKDLNSHICYQFNL
LSSLSWSEAHSSCQMQGGTLLSITDETEENFIREHMSSKTVEVWMGLNQ
LDEHAGWQWSDGTPLNYLNWSPEVNFEPFVEDHCGTFSSFMPSAWRS
RDCESTLPYICKKYLNHIDHEIVEKDAWKYYATHCEPGWNPYNRNCYKLQ
KEEKTWHEALRSCQADNSALIDITSLAEVEFLVTLLGDENASETWIGLSSN
KIPVSFEWSNDSSVIFTNWHTLEPHIFPNRSQLCVSAEQSEGHWKVKNC
EERLFYICKKAGHVLSDAESGCQEGWERHGGFCYKIDTVLRSFDQASSG
YYCPPALVTITNRFEQAFITSLISSVVKMKDSYFWIALQDQNDTGEYTWKP
VGQKPEPVQYTHWNTHQPRYSGGCVAMRGRHPLGRWEVKHCRHFKA
MSLCKQPVENQEKAEYEER (SEQ ID NO: 1)

FIG. 7

MLLSPSLLLLLLLGAPRGCAEGVAAALTPERLLEWQDKGIFVIQSESLKKCI
QAGKSVLTLENCKQANKHMLWKWVSNHGLFNIGGSGCLGLNFSAPEQP
LSLYECDSTLVSLRWRCNRKMITGPLQYSVQVAHDNTVVASRKYIHKWIS
YGSGGGDICEYLHKDLHTIKGNTHGMPCMFPFQYNHQWHHECTREGRE
DDLLWCATTSRYERDEKWGFCPDPTSAEVGCDTIWEKDLNSHICYQFNL
LSSLSWSEAHSSCQMQGGTLLSITDETEENFIREHMSSKTVEVWMGLNQ
LDEHAGWQWSDGTPLNYLNWSPEVNFEPFVEDHCGTFSSFMPSAWRS
RDCESTLPYICKKYLNHIDHE (SEQ ID NO: 2)

FIG. 8

IVEKDAWKYYATHCEPGWNPYNRNCYKLQKEEKTWHEALRSCQADNSA
LIDITSLAEVEFLVTLLGDENASETWIGLSSNKIPVSFEWSNDSSVIFTNWH
TLEPHIFPNRSQLCVSAEQSEGHWKVKNCEERLFYICKKAGHVLSDAESG
CQEGWERHGGFCYKIDTVLRSFDQASSGYYCPPALVTITNRFEQAFITSLI
SSVVKMKDSYFWIALQDQNDTGEYTWKPVGQKPEPVQYTHWNTHQPR
YSGGCVAMRGRHPLGRWEVKHCRHFKAMSLCKQPVENQEKAEYEER

(SEQ ID NO: 3)

FIG. 9

MLLSPSLLLLLLLGAPRGCAEGVAAALTPERLLEWQDKGIFVIQSESLKKCI
QAGKSVLTLENCKQANKHMLWKWVSNHGLFNIGGSGCLGLNFSAPEQP
LSLYECDSTLVSLRWRCNRKMITGPLQYSVQVAHDNTVVASRKYIHKWIS
YGSGGGDICEYLHKDLHTIKGNTHGMPCMFPFQYNHQWHHECTREGRE
DDLLWCATTSRYERDEKWGFCPDPTSAEVGCDTIWEKDLNSHICYQFNL
LSSLSWSEAHSSCQMQGGTLLSITDETEENFIREHMSSKTVEVWMGLNQ
LDEHAGWQWSDGTPLNYLNWSPEVNFEPFVEDHCGTFSSFMPSAWRS
RDCESTLPYICKKYLNHIDHEIVEKDAWKYYATHCEPGWNPYNRNCYKLQ
KEEKTWHEALRSCQADNSALIDITSLAEVEFLVTLLGDENASETWIGLSSN
KIPVSFEWSNDSSVIFTNWHTLEPHIFPNRSQLCVSAEQSEGHWKVKNC
EERLFYICKKAGHVLSDAESGCQEGWERHGGFCYKIDTVLRSFDQASSG
YYCPPALVTITNRFEQAFITSLISSVVKMKDSYFWIALQDQNDTGEYTWKP
VGQKPEPVQYTHWNTHQPRYSGGCVAMRGRHPLGRWEVKHCRHFKA
MSLCKQPVENQEKAEYEERWPFHPCYLDWESEPGLASCFKVFHSEKVL
MKRTWREAEAFCEEFGAHLASFAHIEEENFVNELLHSKFNWTEERQFWI
GFNKRNPLNAGSWEWSDRTPVVSSFLDNTYFGEDARNCAVYKANKTLL
PLHCGSKREWICKIPRDVKPK (SEQ ID NO: 4)

FIG. 10

MLLSPSLLLLLLLGAPRGCAEGVAAALTPERLLEWQDKGIFVIQSESLKKCI
QAGKSVLTLENCKQANKHMLWKWVSNHGLFNIGGSGCLGLNFSAPEQP
LSLYECDSTLVSLRWRCNRKMITGPLQYSVQVAHDNTVVASRKYIHKWIS
YGSGGGDICEYLHKDLHTIKGNTHGMPCMFPFQYNHQWHHECTREGRE
DDLLWCATTSRYERDEKWGFCPDPTSAEVGCDTIWEKDLNSHICYQFNL
LSSLSWSEAHSSCQMQGGTLLSITDETEENFIREHMSSKTVEVWMGLNQ
LDEHAGWQWSDGTPLNYLNWSPEVNFEPFVEDHCGTFSSFMPSAWRS
RDCESTLPYICKKYLNHIDHEIVE (SEQ ID NO: 5)

FIG. 11

KDAWKYYATHCEPGWNPYNRNCYKLQKEEKTWHEALRSCQADNSALIDI
TSLAEVEFLVTLLGDENASETWIGLSSNKIPVSFEWSNDSSVIFTNWHTLE
PHIFPNRSQLCVSAEQSEGHWKVKNCEERLFYICKKAGHVLSDAESGCQ
EGWERHGGFCYKIDTVLRSFDQASSGYYCPPALVTITNRFEQAFITSLISS
VVKMKDSYFWIALQDQNDTGEYTWKPVGQKPEPVQYTHWNTHQPRYS
GGCVAMRGRHPLGRWEVKHCRHFKAMSLCKQPVENQEKAEYEERWPF
HPCYLDWESEPGLASCFKVFHSEKVLMKRTWREAEAFCEEFGAHLASFA
HIEEENFVNELLHSKFNWTEERQFWIGFNKRNPLNAGSWEWSDRTPVVS
SFLDNTYFGEDARNCAVYKANKTLLPLHCGSKREWICKIPRDVKPK (SEQ ID NO: 6)

FIG. 12

MLLSPSLLLLLLLGAPRGCAEGVAAALTPERLLEWQDKGIFVIQSESLKKCI
QAGKSVLTLENCKQANKHMLWKWVSNHGLFNIGGSGCLGLNFSAPEQP
LSLYECDSTLVSLRWRCNRKMITGPLQYSVQVAHDNTVVASRKYIHKWIS
YGSGGGDICEYLHKDLHTI (SEQ ID NO: 7)

FIG. 13

MLLSPSLLLLLLLGAPRGCAEGVAAALTPERLLEWQDKGIFVIQSESLKKCI
QAGKSVLTLENCKQANKHMLWKWVSNHGLFNIGGSGCLGLNFSAPEQP
LSLYECDSTLVSLRWRCNRKMITGPLQYSVQVAHDNTVVASRKYIHKWIS
YGSGGGDICEYLHKDLHTIKGNTHGMPCMFPFQYNHQWHHECTREGRE
DDLLWCATTSRYERDEKWGFCPDPTSAEVG (SEQ ID NO: 8)

FIG. 14

MLLSPSLLLLLLLGAPRGCAEGVAAALTPERLLEWQDKGIFVIQSESLKKCI
QAGKSVLTLENCKQANKHMLWKWVSNHGLFNIGGSGCLGLNFSAPEQP
LSLYECDSTLVSLRWRCNRKMITGPLQYSVQVAHDNTVVASRKYIHKWIS
YGSGGGDICEYLHKDLHTIKGNTHGMPCMFPFQYNHQWHHECTREGRE
DDLLWCATTSRYERDEKWGFCPDPTSAEVGCDTIWEKDLNSHICYQFNL
LSSLSWSEAHSSCQMQGGTLLSITDETEENFIREHMSSKTVEVWMGLNQ
LDEHAGWQWSDGTPLNYLNWSPEVNFEPFVEDHCGTFSSFMPSAWRS
RDCESTLPYICKKYLNHIDHEIVE (SEQ ID NO: 9)

FIG. 15

MLLSPSLLLLLLLGAPRGCAEGVAAALTPERLLEWQDKGIFVIQSESLKKCI
QAGKSVLTLENCKQANKHMLWKWSNHGLFNIGGSGCLGLNFSAPEQP
LSLYECDSTLVSLRWRCNRKMITGPLQYSVQVAHDNTVVASRKYIHKWIS
YGSGGGDICEYLHKDLHTIKGNTHGMPCMFPFQYNHQWHHECTREGRE
DDLLWCATTSRYERDEKWGFCPDPTSAEVGCDTIWEKDLNSHICYQFNL
LSSLSWSEAHSSCQMQGGTLLSITDETEENFIREHMSSKTVEVWMGLNQ
LDEHAGWQWSDGTPLNYLNWSPEVNFEPFVEDHCGTFSSFMPSAWRS
RDCESTLPYICKKYLNHIDHEIVEKDAWKYYATHCEPGWNPYNRNCYKLQ
KEEKTWHEALRSCQADNSALIDITSLAEVEFLVTLLGDENASETWIGLSSN
KIPVSFEWSNDSSVIFTNWHTLEPHIFPNRSQLCVSAEQSEGHWKVKNC
EERLFYICKKAGHVLSD (SEQ ID NO: 10)

FIG. 16

MLLSPSLLLLLLLGAPRGCAEGVAAALTPERLLEWQDKGIFVIQSESLKKCI
QAGKSVLTLENCKQANKHMLWKWVSNHGLFNIGGSGCLGLNFSAPEQP
LSLYECDSTLVSLRWRCNRKMITGPLQYSVQVAHDNTVVASRKYIHKWIS
YGSGGGDICEYLHKDLHTIKGNTHGMPCMFPFQYNHQWHHECTREGRE
DDLLWCATTSRYERDEKWGFCPDPTSAEVGCDTIWEKDLNSHICYQFNL
LSSLSWSEAHSSCQMQGGTLLSITDETEENFIREHMSSKTVEVWMGLNQ
LDEHAGWQWSDGTPLNYLNWSPEVNFEPFVEDHCGTFSSFMPSAWRS
RDCESTLPYICKKYLNHIDHEIVEKDAWKYYATHCEPGWNPYNRNCYKLQ
KEEKTWHEALRSCQADNSALIDITSLAEVEFLVTLLGDENASETWIGLSSN
KIPVSFEWSNDSSVIFTNWHTLEPHIFPNRSQLCVSAEQSEGHWKVKNC
EERLFYICKKAGHVLSDAESGCQEGWERHGGFCYKIDTVLRSFDQASSG
YYCPPALVTITNRFEQAFITSLISSVVKMKDSYFWIALQDQNDTGEYTWKP
VGQKPEPVQYTHWNTHQPRYSGGCVAMRGRHPLGRWEVKHCRHFKA
MSLCKQPVENQE (SEQ ID NO: 11)

FIG. 17

MLLSPSLLLLLLLGAPRGCAEGVAAALTPERLLEWQDKGIFVIQSESLKKCI
QAGKSVLTLENCKQANKHMLWKWVSNHGLFNIGGSGCLGLNFSAPEQP
LSLYECDSTLVSLRWRCNRKMITGPLQYSVQVAHDNTVVASRKYIHKWIS
YGSGGGDICEYLHKDLHTIKGNTHGMPCMFPFQYNHQWHHECTREGRE
DDLLWCATTSRYERDEKWGFCPDPTSAEVGCDTIWEKDLNSHICYQFNL
LSSLSWSEAHSSCQMQGGTLLSITDETEENFIREHMSSKTVEVWMGLNQ
LDEHAGWQWSDGTPLNYLNWSPEVNFEPFVEDHCGTFSSFMPSAWRS
RDCESTLPYICKKYLNHIDHEIVEKDAWKYYATHCEPGWNPYNRNCYKLQ
KEEKTWHEALRSCQADNSALIDITSLAEVEFLVTLLGDENASETWIGLSSN
KIPVSFEWSNDSSVIFTNWHTLEPHIFPNRSQLCVSAEQSEGHWKVKNC
EERLFYICKKAGHVLSDAESGCQEGWERHGGFCYKIDTVLRSFDQASSG
YYCPPALVTITNRFEQAFITSLISSVVKMKDSYFWIALQDQNDTGEYTWKP
VGQKPEPVQYTHWNTHQPRYSGGCVAMRGRHPLGRWEVKHCRHFKA
MSLCKQPVENQEKAEYEERWPFHPCYLDWESEPGLASCFKVFHSEKVL
MKRTWREAEAFCEEFGAHLASFAHIEEENFVNELLHSKFNWTEERQFWI
GFNKRNPLNAGSWEWSDRTPVVSSFLDNTYFGEDARNCAVYKANKTLL
PLHCGSKREWICKIPRDVKPK (SEQ ID NO: 12)

FIG. 18

CDTIWEKDLNSHICYQFNLLSSLSWSEAHSSCQMQGGTLLSITDETEENFIREHMSSKTVEVWMGLNQLDEHAGWQWSDGTPLNYLNWSPEVNFEPFVEDHCGTFSSFMPSAWRSRDCESTLPYICKKYLNHIDHEIVE (SEQ ID NO: 13)

FIG. 19

MLLSPSLLLLLLLGAPRGCAEGVAAALTPERLLEWQDKGIFVIQSESLKKCI
QAGKSVLTLENCKQANKHMLWKWSNHGLFNIGGSGCLGLNFSAPEQP
LSLYECDSTLVSLRWRCNRKMITGPLQYSVQVAHDNTVVASRKYIHKWIS
YGSGGGDICEYLHKDLHTIKGNTHGMPCMFPFQYNHQWHHECTREGRE
DDLLWCATTSRYERDEKWGFCPDPTSAEVGCDTIWEKDLNSHICYQFNL
SSLSWSEAHSSQMQGGTLLSITDETEENFIREHMSSKTVEVWMGLNQL
DEHAGWQWSDGTPLNYLNWSPEVNFEPFVEDHCGTFSSFMPSAWRSR
DCESTLPYICKKYLNHIDHEIVEKDAWKYYATHCEPGWNPYNRNCYKLQK
EEKTWHEALRSCQADNSALIDITSLAEVEFLVTLLGDENASETWIGLSSNK
IPVSFEWSNDSSVIFTNWHTLEPHIFPNRSQLCVSAEQSEGHWKVKNCE
ERLFYICKKAGHVLSDAESGCQEGWERHGGFCYKIDTVLRSFDQASSGY
YCPPALVTITNRFEQAFITSLISSVVKMKDSYFWIALQDQNDTGEYTWKPV
GQKPEPVQYTHWNTHQPRYSGGCVAMRGRHPLGRWEVKHCRHFKAM
SLCKQPVENQEKAEYEERWPFHPCYLDWESEPGLASCFKVFHSEKVLM
KRTWREAEAFCEEFGAHLASFAHIEEENFVNELLHSKFNWTEERQFWIG
FNKRNPLNAGSWEWSDRTPVVSSFLDNTYFGEDARNCAVYKANKTLLPL
HCGSKREWICKIPRDVKPKIPFWYQYDVPWLFYQDAEYLFHTFASEWLN
FEFVCSWLHSDLLTIHSAHEQEFIHSKIKALSKYGASWWIGLQEERANDEF
RWRDGTPVIYQNWDTGRERTVNNQSQRCGFISSITGLWGSEECSVSMP
SICKRKKVWLIEKKKDTPKQHGTCPKGWLYFNYKCLLLNIPKDPSSWKN
WTHAQHFCAEEGGTLVAIESEVEQAFITMNLFGQTTSVWIGLQNDDYET
WLNGKPVVYSNWSPFDIINIPSHNTTEVQKHIPLCALLSSNPNFHFTGKW
YFEDCGKEGYGFVCEKMQDTSGHGVNTSDMYPMPNTLEYGNRTYKIINA
NMTWYAAIKTCLMHKAQLVSITDQYHQSFLTVVLNRLGYAHWIGLFTTDN
GLNFDWSDGTKSSFTFWKDEESSLLGDCVFADSNGRWHSTACESFLQG
AICHVPPETRQSEHPELCSETSIPWIKFKSNCYSFSTVLDSMSFEAAHEFC
KKEGSNLLTIKDEAENAFLLEELFAFGSSVQMVWLNAQFDGNNETIKWFD
GTPTDQSNWGIRKPDTDYFKPHHCVALRIPEGLWQLSPCQEKKGFICKM
EADIHTAEALPEKGPSHSIIPLAVVLTLIVIVAICTLSFCIYKHNGGFFRRLAG
FRNPYYPATNFSTVYLEENILISDLEKSDQ (SEQ ID NO: 14)

FIG. 20

MDSYLLMWGLLTFIMVPGCQAELCDDDPPEIPHATFKAMAYKEGTMLNC
ECKRGFRRIKSGSLYMLCTGNSSHSSWDNQCQCTSSATRNTTKQVTPQ
PEEQKERKTTEMQSPMQPVDQASLPGHCREPPPWENEATERIYHFVVG
QMVYYQCVQGYRALHRGPAESVCKMTHGKTRWTQPQLICTGEMETSQF
PGEEKPQASPEGRPESETSCLVTTTDFQIQTEMAATMETSIFTTEYQVAV
AGCVFLLISVLLLSGLTWQRRQRKSRRTI (SEQ ID NO: 15)

| Position | Residue | Score | Prediction |
|---|---|---|---|
| 48 | NCE | -0.32701759 | Non-glycosylated |
| 70 | NSS | 0.37511271 | Potential Glycosylated |
| 78 | NQC | -0.35326057 | Non-glycosylated |
| 89 | NTT | 0.24039211 | Potential Glycosylated |
| 133 | NEA | -0.58545335 | Non-glycosylated |

FIG. 23

FIG. 24
Linker
PLA2R epitope  FITC
| | Fluorescent microscope | Light microscope |
|---|---|---|
| Patient 1 | 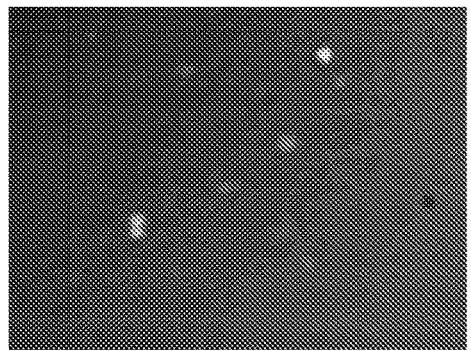 | 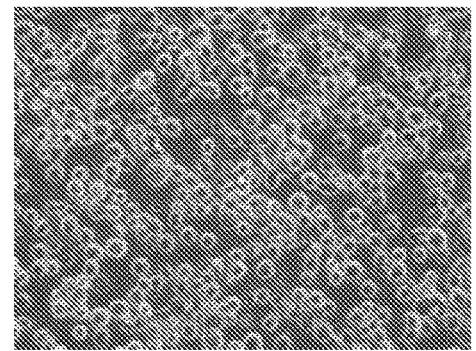 |
| Patient 2 | 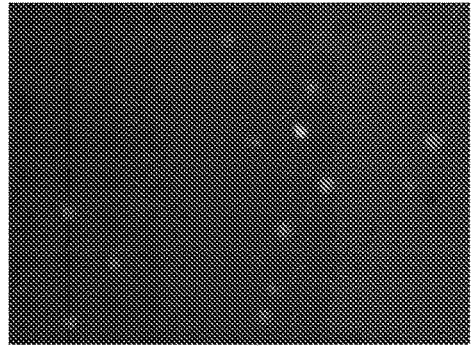 | 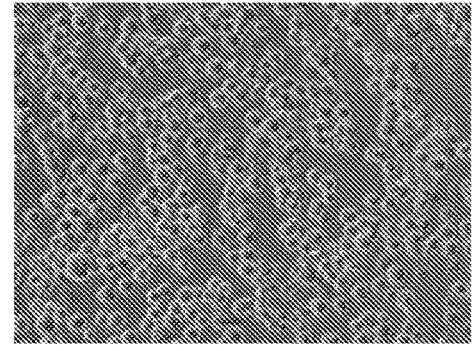 |
| Patient 3 | 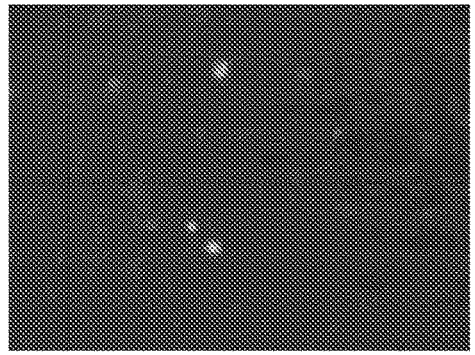 | 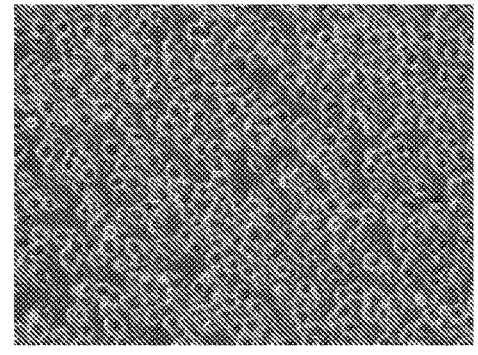 |

FIG. 27

Dsg1

EC1 EC2 EC3 — TEV cleavage site
— His tag
↑
Conjugation site

Dsg3

EC1 EC2 EC3 EC4 — TEV cleavage site
— His tag
↑
Conjugation site

Linker

Dsg epitope ⬢—● Cytotoxic agent

Dsg-Epitope —Linker— MMAE

|  | Fluorescent microscope | | Light microscope |
|---|---|---|---|
|  | − EDC | + EDC | + EDC |
| Patient 1 | | | |
| Patient 2 | | | |

FIG. 31

EWIKFAAACREGEDNSKRNPIAKIHSDCAANQQVTYRISGVGIDQPPYGIF
VINQKTGEINITSIVDREVTPFFIIYCRALNSMGQDLERPLELRVRVLDINDN
PPVFSMATFAGQIEENSNANTLVMILNATDADEPNNLNSKIAFKIIRQEPSD
SPMFIINRNTGEIRTMNNFLDREQYGQYALAVRGSDRDGGADGMSAECE
CNIKILDVNDNIPYMEQSSYTIEIQENTLNSNLLEIRVIDLDEEFSANVMAVI
FFISGNEGNWFEIEMNERTNVGILKVVKPLDYEAMQSLQLSIGVRNKAEF
HHSIMSQYKLKASAISVTVLNVIEGPVF (SEQ ID NO: 16)

FIG. 32

EWVKFAKPCREGEDNSKRNPIAKITSDYQATQKITYRISGVGIDQPPFGIF
VVDKNTGDINITAIVDREETPSFLITCRALNAQGLDVEKPLILTVKILDINDNP
PVFSQQIFMGEIEENSASNSLVMILNATDADEPNHLNSKIAFKIVSQEPAG
TPMFLLSRNTGEVRTLTNSLDREQASSYRLVVSGADKDGEGLSTQCECN
IKVKDVNDNFPMFRDSQYSARIEENILSSELLRFQVTDLDEEYTDNWLAVY
FFTSGNEGNWFEIQTDPRTNEGILKVVKALDYEQLQSVKLSIAVKNKAEFH
QSVISRYRVQSTPVTIQVINVREGIAFRPASKTFTVQKGISSKKLVDYILGT
YQAIDEDTNKAASNVKYVMGRNDGGYLMIDSKTAEIKFVKNMNRDSTFIV
NKTITAEVLAIDEYTGKTSTGTVYVRVPDFNDNCPTAVLEK (SEQ ID NO: 17)

DIAGNOSIS, PREVENTION, AND/OR TREATMENT OF AUTOIMMUNE DISEASES

CROSS REFERENCE TO RELATED APPLICATIONS

This application is the U.S. National Stage Application under 35 U.S.C. § 371 of International Application No. PCT/US2017/046626, filed Aug. 11, 2017, designating the U.S. and published in English as WO 2018/031947 A1 on Feb. 15, 2018, which claims the benefit of U.S. Provisional Application No. 62/374,382, filed Aug. 12, 2016, which is hereby incorporated by reference in its entirety.

SEQUENCE LISTING IN ELECTRONIC FORMAT

The present application is being filed along with an Electronic Sequence Listing as an ASCII text file via EFS-Web. The Electronic Sequence Listing is provided as a file entitled IMWO001WOSEQLIST.txt, created and last saved on Aug. 11, 2017, which is 72,810 bytes in size. The information in the Electronic Sequence Listing is incorporated herein by reference in its entirety in accordance with 35 U.S.C. § 1.52(e).

BACKGROUND

Field

The present disclosure generally relates to compositions, methods, and/or kits for diagnosis, prevention and/or treatment of autoimmune system diseases by detecting, targeting, and/or eliminating epitope-specific autoimmune cells.

Description of the Related Art

Autoimmune diseases can be T cell mediated, B cell mediated, or both and can be associated with organ and/or tissue damage.

SUMMARY

In some embodiments, a method of treating a patient with membranous nephropathy (MN) is provided. In some embodiments, the method of treating a patient with MN comprises identifying a patient with MN, and administering to the patient a complex comprising a PLA2R epitope and a drug, wherein the epitope is comprised within a PLA2R fragment, thereby eliminating or reducing an anti-PLA2R autoantibody producing B cell population in the patient.

In some embodiments of the method of treating a patient with MN, the PLA2R epitope is as provided in SEQ ID NO: 13. In some embodiments of the method, the sequence of the PLA2R fragment is as provided in SEQ ID NO: 1. In some embodiments of the method, the sequence of the PLA2R fragment is as provided in SEQ ID NO: 2. In some embodiments of the method, the PLA2R fragment is as provided in SEQ ID NO: 2 and at least about 5% of the sequence provided in SEQ ID NO: 3. In some embodiments of the method, the PLA2R fragment is as provided in SEQ ID NO: 4. In some embodiments of the method, the PLA2R fragment is as provided in SEQ ID NO: 5. In some embodiments of the method, the PLA2R fragment is as provided in SEQ ID NO: 5 and at least about 5% of the sequence provided in SEQ ID NO: 6. In some embodiments of the method, the drug is selected from the group consisting of antisense RNA, miRNA, siRNA or RNA fragment for RNAi, one or more Duocarmycin analogues, or cytotoxic drug such as adozelesin, bizelesin, carzelesin, Cyclophosphamide, methotrexate, 5-fluorouracil, Doxorubicin, cyclophosphamide, Epirubicin, cisplatin, 5-fluorouracil and capecitabine. In some embodiments of the method, an efficacy of eliminating the anti-PLA2R autoantibody producing B cell population ranges from about 70% to about 100%. In some embodiments of the method, the complex also eliminates a T cell population, wherein the T cell population provides T cell help to the anti-PLA2R autoantibody producing B cell population.

In some embodiments, a complex comprising a PLA2R epitope and a drug is provided. In some embodiments of the complex, the epitope is comprised within a PLA2R fragment. In some embodiments of the complex, the PLA2R epitope is as provided in SEQ ID NO: 13. In some embodiments of the complex, the sequence of the PLA2R fragment is as provided in SEQ ID NO: 1. In some embodiments of the complex, the sequence of the PLA2R fragment is as provided in SEQ ID NO: 2. In some embodiments of the complex, the sequence of the PLA2R fragment is as provided in SEQ ID NO: 2 and at least about 5% of the sequence provided in SEQ ID NO: 3. In some embodiments of the complex, the sequence of the PLA2R fragment is as provided in SEQ ID NO: 4. In some embodiments of the complex, the sequence of the PLA2R fragment is as provided in SEQ ID NO: 5. In some embodiments of the complex, the sequence of the PLA2R fragment is as provided in SEQ ID NO: 5 and at least about 5% of the sequence provided in SEQ ID NO: 6. In some embodiments of the complex, the drug is selected from the group consisting of antisense RNA, miRNA, siRNA or RNA fragment for RNAi, one or more Duocarmycin analogues, or cytotoxic drug such as adozelesin, bizelesin, carzelesin, Cyclophosphamide, methotrexate, 5-fluorouracil, Doxorubicin, cyclophosphamide, Epirubicin, cisplatin, 5-fluorouracil and capecitabine. In some embodiments of the complex, the drug is linked to the PLA2R fragment via a valine-citrulline linker.

In some embodiments, a method of delivering a drug to a subject having autoimmune B cells or T cells is provided. In some embodiments, the method of delivering a drug comprises providing the drug in an epitope-drug conjugate (EDC) comprising an epitope conjugated to the drug via a linker, the epitope being recognized by receptors on the autoimmune B cells or T cells in the subject, the drug having an activity that blocks the B cells from stimulating other cells, and intradermally or subcutaneously administering the EDC to the subject. In some embodiments of the method of delivering a drug, the autoimmune B cells or T cells are circulating in the blood of the subject. In some embodiments of the method of delivering a drug, the autoimmune B cells or T cells are in lymph nodes of the subject. In some embodiments of the method of delivering a drug, the drug kills the B cell or the T cell. In some embodiments of the method of delivering a drug, the drug is selected from the group consisting of Duocarmycin A, Duocarmycin B1, Duocarmycin B2, Duocarmycin C1, Duocarmycin C2, Duocarmycin D, Duocarmycin SA, CC-1065, adozelesin, bizelesin, carzelesin, Cyclophosphamide, methotrexate, 5-fluorouracil, Doxorubicin, cyclophosphamide, Epirubicin, cisplatin, 5-fluorouracil or capecitabine, Monomethyl auristatin E (MMAE), anthracyclines, oxaliplatin, or bortezomib. In some embodiments of the method of delivering a drug, the drug blocks release of cytokines from the B cell or the T cell or block cytokine signaling in the B cell or the T cell. In some embodiments of the method of delivering a drug, the drug is selected from the group consisting of Rapamycin, Ciclosporin, Tacrolimus, Mycophenolate, Fingolimod, Imatinib, Temsirolimus, Sorafenib, Sunitinib, Pirfenidone, Src family tyrosine kinase inhibitors (Dasatinib, Saracatinib, Bosutinib, Bafetinib), MEK kinase inhibitors (Selumetinib, Trametinib, and Refametinib). In some embodiments of the method of delivering a drug, the subject is not in an acute phase of active autoimmune disease. In some embodiments of the method of delivering a drug, the subject has been treated with an immunosuppressant such that the patient is not in the acute phase of active autoimmune disease. In some embodiments of the method of delivering a drug, the EDC has a molecular weight of 14-70 kDa.

In some embodiments, a method of treating a patient with Pemphigus vulgaris (PV) is provided. In some embodiments, the method of treating a patient with PV comprises identifying a patient with PV, and administering to the patient a complex comprising a desmoglein 1 or a desmoglein 3 epitope and a drug, wherein the epitope is comprised within a desmoglein 1 or desmoglein 3 fragment, thereby eliminating or reducing an anti-desmoglein 1 or anti-desmoglein 3 autoantibody producing B cell population in the patient.

In some embodiments of the method of treating a patient with PV, the desmoglein 1 epitope is as provided in SEQ ID NO: 16. In some embodiments of the method of treating a patient with PV, the sequence of the desmoglein 1 fragment is as provided in SEQ ID NO: 16. In some embodiments of the method of treating a patient with PV, the desmoglein 3 epitope is as provided in SEQ ID NO: 17. In some embodiments of the method, the sequence of the desmoglein 3 fragment is as provided in SEQ ID NO: 17. In some embodiments of the method, the drug is selected from the group consisting of antisense RNA, miRNA, siRNA or RNA fragment for RNAi, one or more Duocarmycin analogues, or cytotoxic drug such as adozelesin, bizelesin, carzelesin, Cyclophosphamide, methotrexate, 5-fluorouracil, Doxorubicin, cyclophosphamide, Epirubicin, cisplatin, 5-fluorouracil and capecitabine. In some embodiments of the method, an efficacy of eliminating the anti-desmoglein 1 autoantibody producing B cell population ranges from about 70% to about 100%. In some embodiments of the method, an efficacy of eliminating the anti-desmoglein 3 autoantibody producing B cell population ranges from about 70% to about 100%. In some embodiments of the method, the complex also eliminates a T cell population, wherein the T cell population provides T cell help to the anti-desmoglein 1 autoantibody producing B cell population. In some embodiments of the method, the complex also eliminates a T cell population, wherein the T cell population provides T cell help to the anti-desmoglein 3 autoantibody producing B cell population.

In some embodiments, an epitope drug complex (EDC) is provided. In some embodiments, the EDC comprises a drug and a desmoglein 1 epitope or desmoglein 3 epitope, wherein the desmoglein 1 epitope is comprised within a desmoglein 1 fragment and wherein the desmoglein 3 epitope is comprised within a desmoglein 3 fragment.

In some embodiments of the EDC, the desmoglein 1 epitope is as provided in SEQ ID NO: 16. In some embodiments of the EDC, the sequence of the desmoglein 1 fragment is as provided in SEQ ID NO: 16. In some embodiments of the EDC, the desmoglein 3 epitope is as provided in SEQ ID NO: 17. In some embodiments of the EDC, the sequence of the desmoglein 3 fragment is as provided in SEQ ID NO: 17. In some embodiments of the EDC, the drug is selected from the group consisting of antisense RNA, miRNA, siRNA or RNA fragment for RNAi, one or more Duocarmycin analogues, or cytotoxic drug such as adozelesin, bizelesin, carzelesin, Cyclophosphamide, methotrexate, 5-fluorouracil, Doxorubicin, cyclophosphamide, Epirubicin, cisplatin, 5-fluorouracil and capecitabine.

In some embodiments, a method for diagnosing an autoimmune disease in a subject is provided. In some embodiments, the method of diagnosing comprises detecting a presence of a population of autoimmune B and/or T cells in the subject by collecting a sample from the subject, incubating the sample with an EDC comprising an epitope and a fluorophore, wherein the epitope is specific for one or more B cell receptors expressed by the autoimmune B cells and/or one or more T cell receptors expressed by the autoimmune T cells, detecting a binding of the EDC to the B cells and/or T cells by microscopy, thereby diagnosing an autoimmune disease in the subject.

BRIEF DESCRIPTION OF THE DRAWINGS

FIG. 1 shows an embodiment of the topological folding and structural domains of PLA2R in a cell membrane.

FIG. 2 shows an embodiment of topological folding of PLA2R with the dominant conformational epitope.

FIG. 3 shows a schematic of an embodiment of antigen processing and recruitment of T cell help by B cells.

FIG. 4 shows a schematic of the molecular basis of an embodiment of epitope-drug conjugate (EDC) design.

FIG. 5 shows a schematic illustration of an embodiment of a mechanism of EDC treatment.

FIG. 6 shows the amino acid sequence of an embodiment of PLA2R fragment (SEQ ID NO: 1).

FIG. 7 shows the amino acid sequence of an embodiment of PLA2R fragment (SEQ ID NO: 2).

FIG. 8 shows the amino acid sequence of an embodiment of PLA2R fragment (SEQ ID NO: 3).

FIG. 9 shows the amino acid sequence of an embodiment of PLA2R fragment (SEQ ID NO: 4).

FIG. 10 shows the amino acid sequence of an embodiment of PLA2R fragment (SEQ ID NO: 5).

FIG. 11 shows the amino acid sequence of an embodiment of PLA2R fragment (SEQ ID NO: 6).

FIG. 12 shows the amino acid sequence of an embodiment of CysR domain (SEQ ID NO: 7) of PLA2R.

FIG. 13 shows the amino acid sequence of an embodiment of CysR and FNII domains (SEQ ID NO: 8) of PLA2R.

FIG. 14 shows the amino acid sequence of an embodiment of CysR, FNII and CTLD1 domains (SEQ ID NO: 9) of PLA2R.

FIG. 15 shows the amino acid sequence of an embodiment of CysR, FNII, and CTLD1, 2 domains (SEQ ID NO: 10) of PLA2R.

FIG. 16 shows the amino acid sequence of an embodiment of CysR, FNII and CTLD1, 2, 3 domains (PLA2R-1-5 domains) (SEQ ID NO: 11) of PLA2R.

FIG. 17 shows the amino acid sequence of an embodiment of CysR, FNII and CTLD1, 2, 3, 4 domains (SEQ ID NO: 12) of PLA2R.

FIG. 18 shows the amino acid sequence of an embodiment of the epitope (SEQ ID NO: 13) of PLA2R against which autoantibodies are present in MN patients.

FIG. 19 shows the amino acid sequence of an embodiment of full-length PLA2R (SEQ ID NO: 14). Shaded region indicates an embodiment the epitope (SEQ ID NO: 13) of PLA2R against which autoantibodies are present in MN patients. Underlined region indicates an embodiment of CysR, FNII and CTLD1 domains (SEQ ID NO: 9) of PLA2R.

FIG. 20 shows potential N-Linked glycosylation sites in the N-terminal 272 amino acids of PLA2R (SEQ ID NO: 15).

FIG. 21 shows a schematic of a drug development platform for autoimmune disease treatment. Top panel shows design of epitope drug conjugate (EDC). Middle panel shows EDC binds to the antigen-specific receptors on the surface of the B cells and T cells. Bottom panel shows the effect of EDC on the targeted immune cells (e.g., cell death).

FIG. 23 shows design of an embodiment of a PLA2R epitope drug conjugate (EDC).

FIG. 24 shows detection of PLA2R epitope specific memory B cells in total B cells isolated from PLA2R-Ab positive PMN patient blood samples.

FIG. 27 shows design of an embodiment of an epitope drug conjugate (EDC) for mucocutaneous PV treatment.

Figure 28:
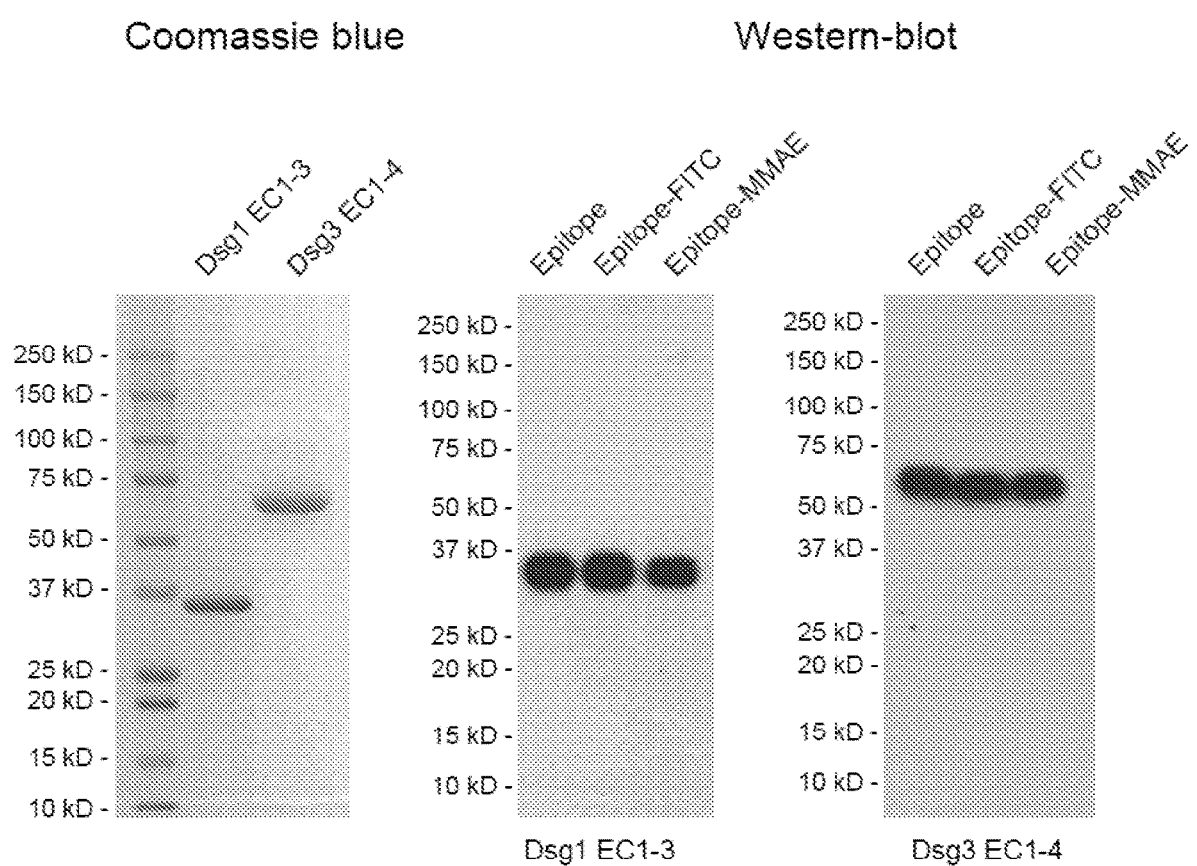

FIG. 28 Purification and autoantibody binding to the drug conjugated epitopes.

Figure 29:
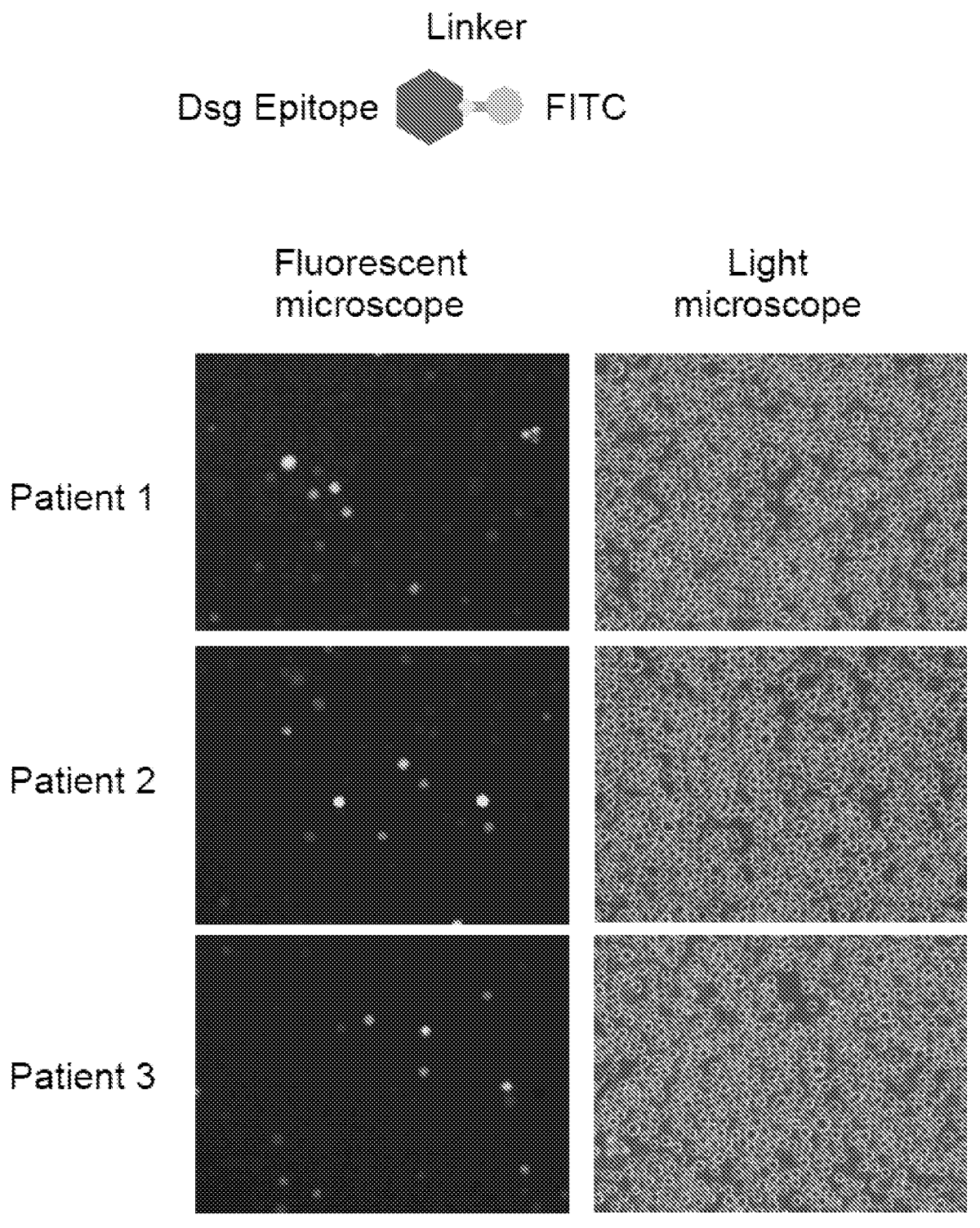

FIG. 29 shows detection of Dsg1 and Dsg3 epitope specific memory B cells in total B cells isolated from mucocutaneous PV patient blood samples.

FIG. 30 shows the effect of Dsg1-epitope-MMAE and Dsg3-epitope-MMAE conjugate on B cells isolated from mucocutaneous PV patients.

FIG. 31 shows the amino acid sequence of an embodiment of an epitope sequence of Dsg1 (SEQ ID NO: 16) for developing EDC.

FIG. 32 shows the amino acid sequence of an embodiment of an epitope sequence of Dsg3 (SEQ ID NO: 17) for developing EDC.

DETAILED DESCRIPTION

Currently, there are no effective treatments for autoimmune diseases except to use high doses of steroid hormones and immunosuppressive agents. These treatments are non-specific, have significant side-effects and often cannot stop the disease from progressing. The major challenge of these treatments is the frequent disease relapse when the dose of the reagents is reduced (e.g., after the disease is in clinical remission), which severely impair the function of the affected organ(s).

Figure 3:
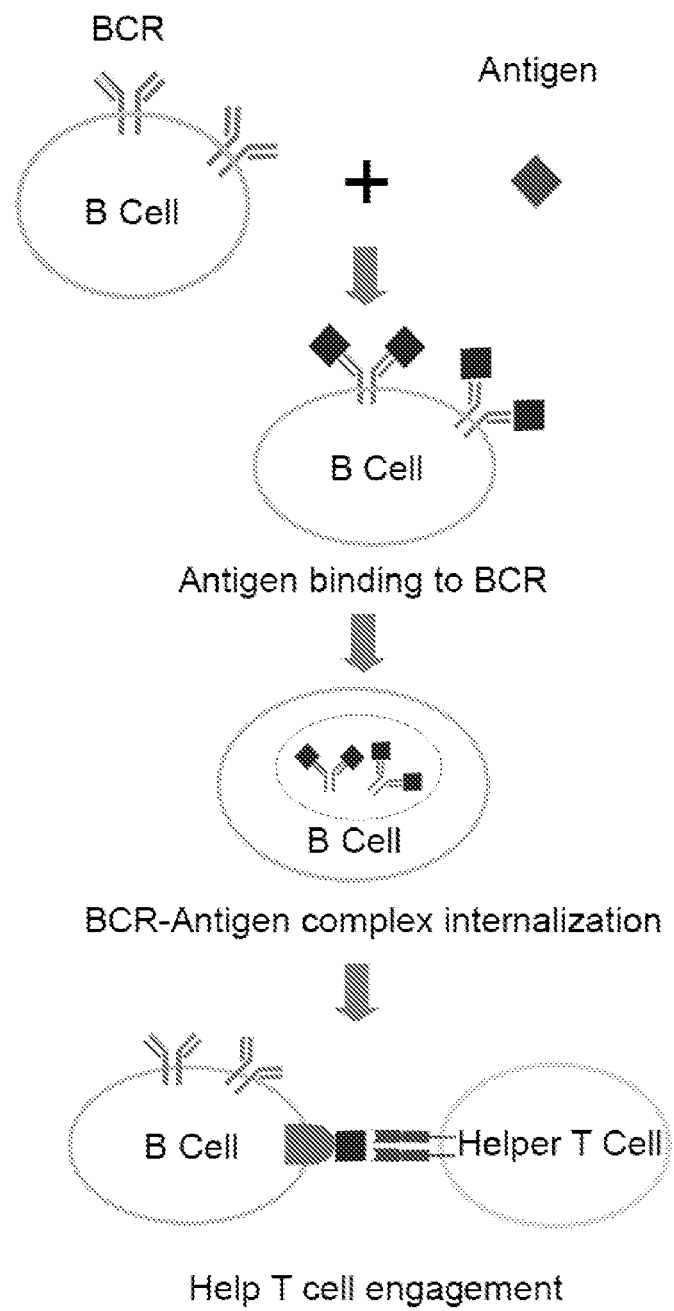

A New Drug Development Platform for Autoimmune Disease Diagnosis, Prevention and/or Treatment Antibody production in B cells is initiated by antigen binding to the cell-surface B cell receptors (BCRs). The initial binding of antigen to the BCR induces a cascade of intracellular signaling events that results in B cell activation. Antigen binding to BCR triggers rapid internalization of the BCR-antigen complex. After internalization, the BCR-antigen complex is sorted into early endosomes and subsequently into major histocompatibility complex class II (MHCII)-containing late endosomes. Upon fusion with lysosomes, these compartments degrade the antigens into peptides that are loaded onto MHCII for presentation to helper T cells (FIG. 3). The engagement of specific helper T cells stimulates antibody production by the activated B cells. (FIG. 3)

An autoimmune disease occurs due to an immune response (e.g., antibody production by B cells) against to a normal body tissue and/or organ. About 80 types of autoimmune diseases are known in humans and almost any tissue and/or organ can be affected.

Clinically, the frequent autoimmune disease relapse in patients is due to the presence of a specific group of memory B cells that are present in a quiescent state in the patient's body and are circulating between the peripheral blood and peripheral lymph tissues and/or organs (e.g., lymph nodes). Upon re-encounter with an antigen for which they are specific, these memory B cells are quickly activated and subsequently differentiate into plasma cells that produce massive amounts of disease-causing antibodies (pathogenic antibodies) in a short period of time. In addition, these memory B cells serve as antigen presenting cells (APCs) that present the processed antigen to antigen-specific helper T cells thus triggering and/or enhancing T cell mediated organ and/or tissue damage. These memory B cells and antigen-specific T cells possess unique and antigen-specific BCRs and T cell receptors (TCRs), respectively, both of which bind specifically to the antigen. Currently, there is no treatment that can specifically target this group of disease-causing memory B cells and antigen specific-T cells (autoimmune memory B cells and T cells). In particular, there is no treatment that can specifically target this group of autoimmune memory B cells and autoimmune T cells circulating between the peripheral blood and peripheral lymph tissues and/or organs (e.g., lymph nodes).

In some embodiments, the present disclosure is related to a new drug development platform that specifically targets this repertoire of autoimmune cells in the peripheral blood and the peripheral lymph organs of a subject/patient. In some embodiments, targets this repertoire of autoimmune cells in the peripheral blood and the peripheral lymph organs will result in a life-long treatment effect.

The part of an antigen responsible for the autoimmune antibody binding is a specific region called an epitope. As used herein "epitope" can be a natural peptide, a synthetic peptide, an artificial peptide, a biosimilar, an aptamer, a protein domain, or a combination thereof. In some embodiments, an epitope is conformational. In some embodiments, an epitope is non-conformational. In some embodiments, an epitope is both conformational and non-conformational. A peptide/protein epitope can be recombinantly expressed as well as obtained in large quantities using one or more techniques that well-known in the art of epitope synthesis and purification. An epitope has a high affinity for the disease-causing autoantibodies, as well as for the antigen-specific BCRs expressed on memory B cells, TCRs expressed on helper T cells, or both. In some embodiments, the epitope can be a non-peptide/protein epitope. Non-limiting examples include DNA, RNA, small molecules, and organic chemicals.

Figure 21:
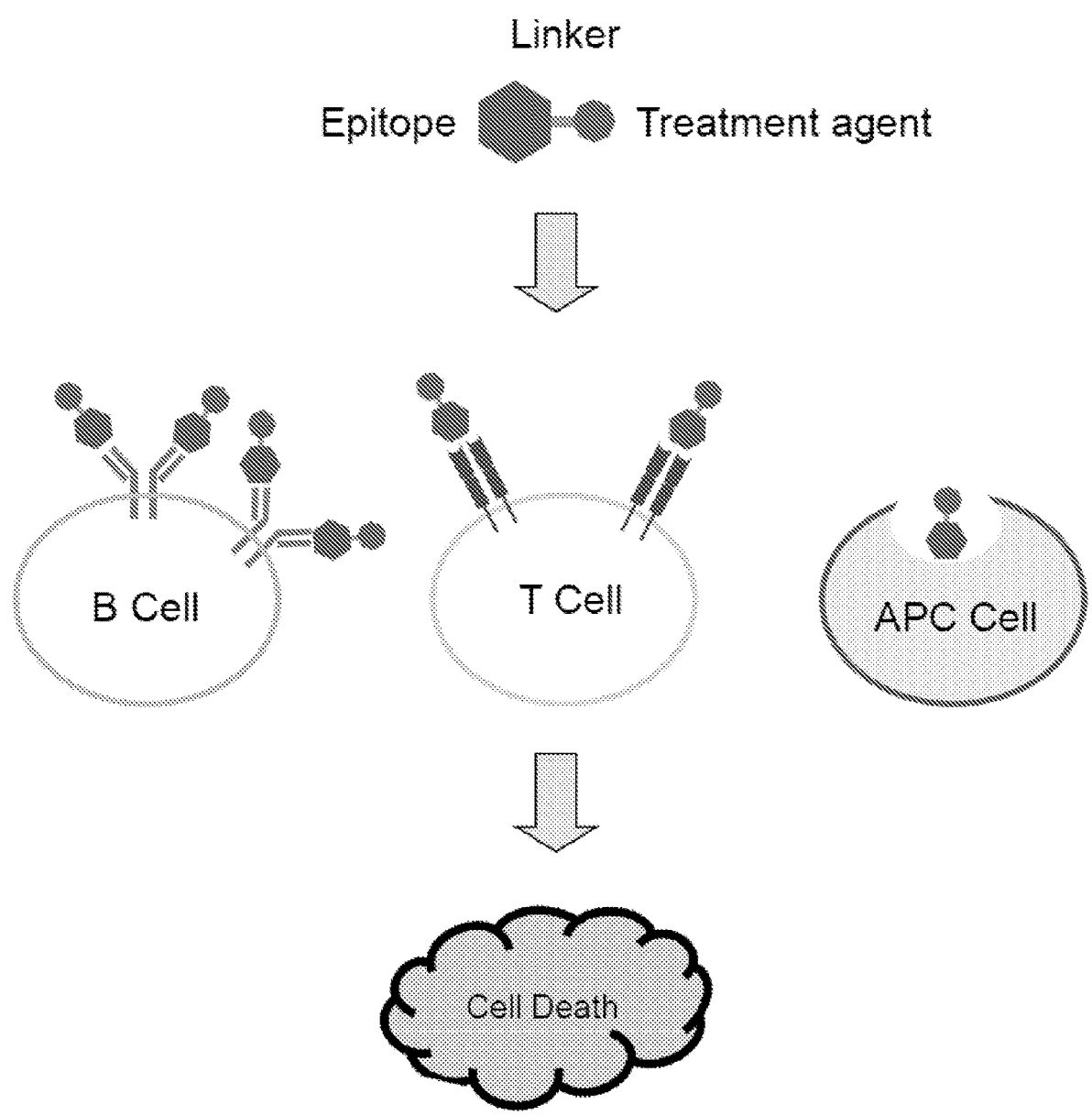

The present disclosure is related epitope-drug conjugates (EDCs), and compositions, methods and/or kits comprising EDCs. In some embodiments, the present disclosure is related to an EDC comprising a peptide epitope that targets antigen-specific BCRs expressed on memory B cells, TCRs expressed on helper T cells, or both (FIG. 21). In some embodiments, the EDC also targets APCs that phagocytose and/or endocytose the EDC (FIG. 21). As the platform is based on an epitope(s) that are specifically recognized by immune cells, the platform according to the present disclosure can be adapted for any autoimmune disease. FIG. 21 shows a schematic of a drug development platform for autoimmune disease treatment. FIG. 21 (top panel) shows design of EDC. FIG. 21 (middle panel) shows EDC binds to the antigen-specific receptors on the surface of the B cells and T cells. EDC can be internalized into the cells via BCR-mediated endocytosis.

In some embodiments, the EDC according to the present disclosure comprises an epitope, a linker, and a drug. In some embodiments, the linker is stable (i.e., not hydrolyzed or degraded) in the patient body and/or circulation outside a cell. In some embodiments, the linker is cleavable allowing separation of the epitope and drug. In some embodiments, the linker is cleaved inside a cell. In some embodiments, the linker is cleaved outside a cell. In some embodiments, the linker is cleaved both inside and outside a cell. In some embodiments, the linker is partially cleaved outside a cell and partially cleaved inside a cell. In some embodiments, the linker is partially cleaved outside a cell and completely cleaved inside a cell. In some embodiments, initial cleavage of the linker occurs outside a cell and final cleavage occurs inside a cell. Non-limiting examples of cleavable linkers include hydrazone linkers, disulfide-based linkers and peptide linkers. In some embodiments, disulfide-based linkers are selectively broken down inside a cell. In some embodiments, disulfide-based linkers are selectively broken down inside a cell because of higher intracellular concentration of thiols. In some embodiments, peptide linkers are selectively broken down inside a cell by intracellular enzymes.

In some embodiments, the linker is non-cleavable. Non-limiting examples of non-cleavable linkers include thioether linkers. PEG4Mal linker, and the like. In some embodiments, the linker is attached to one or more amino acids on the epitope. In some embodiments, the linker is attached to a cysteine residue on the epitope. In some embodiments, the linker is attached to a residue other than cysteine (e.g., lysine) on the epitope. In some embodiments, one or more sites on the epitope for linker attachment can be one or more solvent-accessible cysteine or lysine or both.

Other types of linkers, conjugation chemistries, and conjugation sites on epitopes for generation of EDCs are included within the scope of this disclosure. Non-limiting examples are disclosed in U.S. Pat. Nos. 9,156,854 and 9,388,408, which are hereby incorporated by reference in their entireties. Other non-limiting examples of linkers include Imidoesters, Maleimides, Carbodiimide, Pyridyldithiol, Isocyanate, Isopeptag, SpyTag, SnoopTag and SNAP-tag.

In some embodiments, the linker comprises attachment sites for both the epitope and drug to join the two components. In some embodiments, the linker is cleavable. In some embodiments, the linker is cleavable from one or both of the epitope and the drug. In some embodiments, the linker is non-cleavable. In some embodiments, the linker is non-cleavable from one or both of the epitope and the drug.

In some embodiments, a free cysteine residue is introduced at the C-terminus of the epitope. The thio group of the free cysteine is then conjugated with a cleavable linker. In some embodiments, the cleavable linker is a valine-citrulline linker. In some embodiments, the valine-citrulline linker is pre-conjugated with a drug (e.g., duocarmycin analog). In some embodiments, a free cysteine residue is introduced at the C-terminus of the epitope and the thio group of the free cysteine is conjugated with a cleavable valine-citrulline linker pre-conjugated with a durg (e.g., duocarmycin analog).

In some embodiments, a short sequence of CXPXR is introduced to the C-terminus of the epitope. In some embodiments, the cysteine residue is converted to a formylglycine aldehyde tag. In some embodiments, the cysteine residue is converted to a formylglycine aldehyde tag using a formylglycine-generating enzyme. In some embodiments, the formylglycine aldehyde tag is then conjugated to a drug-linker by a non-cleavable linkage. In some embodiments, the formylglycine aldehyde tag is conjugated to the drug-linker by a non-cleavable linkage via oxime chemistry. In some embodiments, the formylglycine aldehyde tag is conjugated to the drug-linker by a non-cleavable linkage via Pictet-Spengler reaction. In some embodiments, the drug in the drug-linker is a cytotoxic reagent.

In some embodiments, a drug is conjugated to the epitope in a region outside of the BCR/TCR interaction site. In some embodiments, a drug is conjugated to the epitope in a region outside of the BCR/TCR interaction site to one or more lysine residues. In some embodiments, a drug is conjugated to the epitope in a region outside of the BCR/TCR interaction site to one or more lysine residues via amide bonds to an N-hydroxysuccinimide (NHS) ester appended to a drug-linker.

In some embodiments, epitopes can be engineered as described in Example 4 and Example 7. In some embodiments, one or more chemical conjugation sites are introduced into an epitope. In some embodiments, one or more chemical conjugation sites are non-natural amino acids. In some embodiments, one or more chemical conjugation sites include one or more cysteine residues.

In some embodiments, the epitope can be in its native amino acid sequence. In some embodiments, the native amino acid sequence of epitope may be modified. For example, glycosylation sites in an epitope (e.g., the extracellular portion of PLA2R is glycosylated) can add to the size, bulk, and conformational complexity of the epitope. Potential N-linked glycosylation sites (underlined Asn residues) in the first 272 amino acids of PLA2R (SEQ ID NO: 15) are shown in FIG. 20, in Dsg1 epitope (SEQ ID NO: 16) are shown in FIG. 31, and in Dsg3 epitope (SEQ ID NO: 17) are shown in FIG. 32. In some embodiments, the size, bulk, conformational complexity of the epitope can be reduced by substituting potential glycosylation sites (e.g., at Asn70 and Asn89 in FIG. 20) with Gln or any other non-glycosylated amino acids that will not affect protein structure and/or conformation for autoantibody recognition.

In some embodiments, residues that are potentially glycosylated can be substituted using, for example, site directed mutagenesis. In some embodiments, residues that are potentially glycosylated can be substituted using, for example, site directed mutagenesis when using an expression vector to express an epitope. In some embodiments, an epitope can be directly synthesized. In some embodiments, when an epitope is directly synthesized, the peptide and/or protein synthesis can be customized such that the potentially glycosylated residues are replaced with non-glycosylated residues that will not affect protein structure and/or conformation for autoantibody recognition.

In some embodiments, additional modifications may be made to the epitope, for example, to attach a reagent (e.g., a drug) to the epitope, improve accessibility of the epitope to receptors on the cell surface, and/or improve protein expression and yield. For example, the epitope may be modified by inserting small (about 2 to 10 amino acids) N- or C-terminal peptide or both, making conservative and/or non-conservative substitutions, and/or adding one or more heterologous sequences to achieve a desired objective.

In some embodiments, one or more of epitopes provided herein are encoded by nucleic acids. In some embodiments, the epitope-encoding nucleic acid is a cDNA or an mRNA. In some embodiments, the epitope-encoding nucleic acid can be comprised within a protein expression vector. In some embodiments, the protein expression vector is a DNA vector or an RNA vector. In some embodiments, the protein expression vector is an adeno-associated viral (AAV) vector. In some embodiments, the protein expression vector is a mammalian cell expression vector. In some embodiments, the protein expression vector is an insect cell expression vector. In some embodiments, the epitope-encoding nucleic acid comprised within a protein expression vector is operably linked to regulatory elements to regulate the expression of the epitope.

Regulatory elements can include promoters, terminators, enhancers, etc. As used herein, "operably linked" refers to a regulatory element positively or negatively controlling the expression of a protein from a nucleic acid.

One or more of the proteins expression vectors provided herein as well as other protein expression vectors known to one of ordinary skill in the art can be used to obtain large quantities of one or more of the epitopes disclosed herein and fragments and variants thereof for incorporation into one or more of the compositions, methods, and/or kits provided herein. In some embodiments, a variant of an epitope can have about 70% to about 99.99% identity to the epitope. In some embodiments, a variant of an epitope can have about 65, 70, 57, 80, 85, 90, 95, 96, 97, 98, 99, 99.25, 99.5, 99.75, 99.99% identity to the epitope, or a value with a range defined by any two of the aforementioned values.

In some embodiments, the protein expression vector introduces a tag on the encoded epitope. In some embodiments, one or more tags enable purification of the epitope. In some embodiments, the tag is on the N-terminal end. In some embodiments, the tag is on the C-terminal end. In some embodiments, the tag is on both N- and C-terminal ends. Non-limiting examples of tags include chitin binding protein, maltose binding protein, glutathione-S-transferase, thioredoxin, poly(NANP), FLAG, V5, Myc, HA, NE, biotin, biotin carboxyl carrier protein, GFP, Halo, Nus, Fc, AviTag, calmodulin, poly-Glu, E, S, SBP, Softag 1, Softag 3, Strep, TC, VSV, Ty and Xpress. In some embodiments, the tag is a poly-histidine (poly-His) tag.

In some embodiments, the protein expression vector additionally introduces a cleavage site between the epitope and the tag to allow for separation of the epitope from the tag. In some embodiments, the cleavage site is a proteolytic site. In some embodiments, the cleavage site is a non-proteolytic site. Non-limiting examples of proteolytic sites include sites for TEV protease, Factor Xa or enteropeptidase. In some embodiments, the proteolytic site is a thrombin cleavage site. Non-limiting examples of other protease and non-protease cleavage sites that are contemplated include foot-and-mouth disease virus (FMDV) protease, Arg-C proteinase, Asp-N endopeptidase, BNPS-Skatole, Caspases, Chymotrypsin-high specificity, Chymotrypsin-low specificity, Clostripain (Clostridiopeptidase B), CNBr, Enterokinase, Factor Xa, Formic acid, Glutamyl endopeptidase, GranzymeB, Hydroxylamine, Iodosobenzoic acid, LysC, LysN, NTCB (2-nitro-5-thiocyanobenzoic acid), Neutrophil elastase, Pepsin, Proline-endopeptidase, Proteinase K, Staphylococcal peptidase I, Thermolysin, Thrombin, Trypsin, and other site specific enzymes known to one of ordinary skill in the art.

Figure 23:
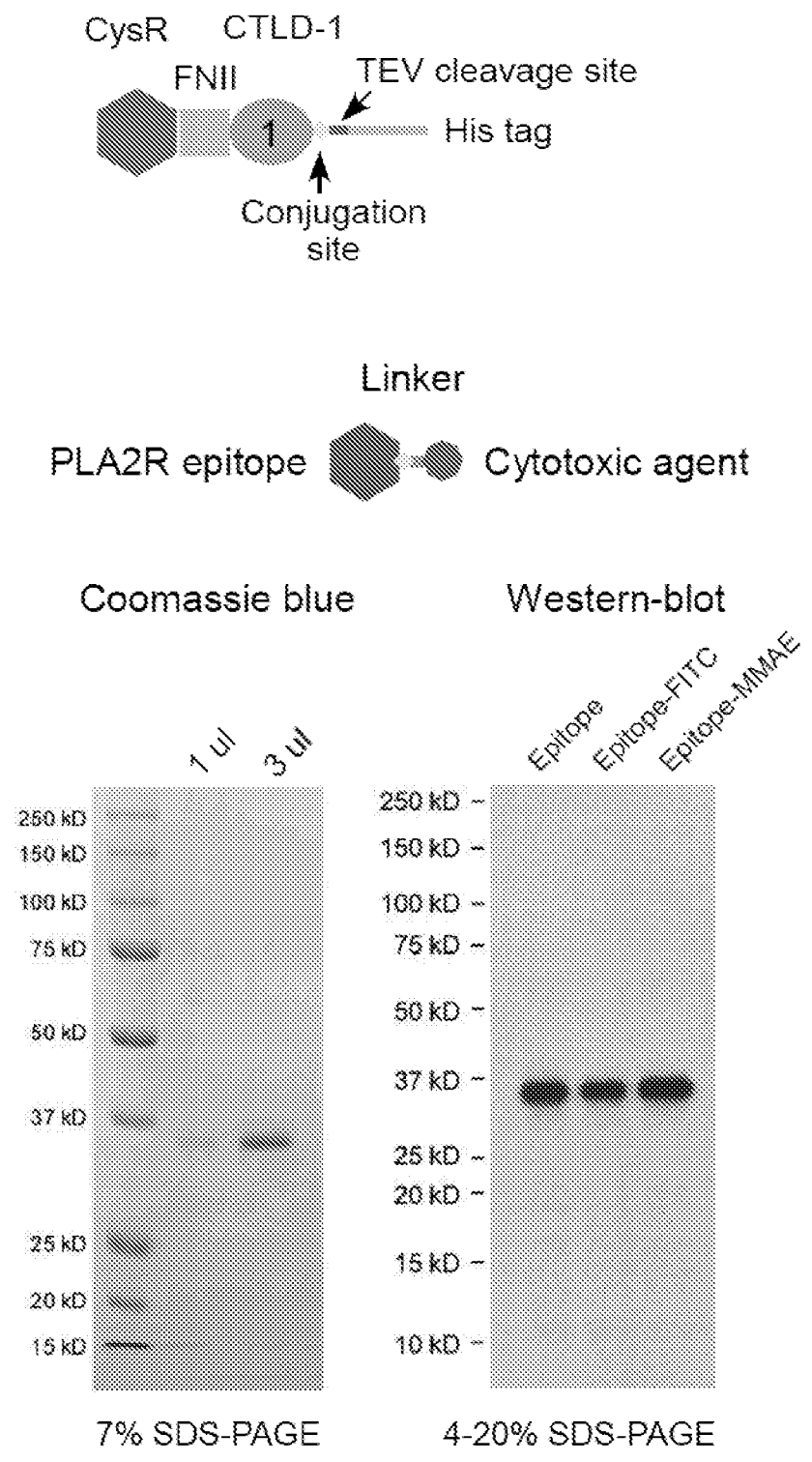

One or more commercially available cell lines can be used to express the epitope. For example, in some embodiments, a poly-His-tagged epitope can be expressed in mammalian cells (e.g., HEK 293 cells) and purified from the cell culture medium using Ni-affinity purification and gel filtration columns. The poly-His tag can then be removed by proteolytic digestion (e.g., using thrombin), and the epitope further purified to homogeneity using gel filtration chromatography to remove the thrombin enzyme as well as the released poly-His tag. Epitope expression and purification can be tested on protein extracts using sodium dodecyl sulfate polyacrylamide gel electrophoresis (SDS-PAGE) (FIG. 23 and FIG. 28). Epitope expression can also be tested using Western blotting (FIG. 23 and FIG. 28) using one or more antibodies and/or patient plasma and/or serum. The SDS-PAGE gel can be stained with one or more of Coomassie dye stains (FIG. 23 and FIG. 28), silver stains, Zinc stains, fluorescent dye stains, and functional group-specific stains.

As used herein, the "drug" in the EDC can also be referred to as a "treatment agent" (FIG. 21; top panel) or "agent." A drug includes agents that specifically used for the prevention and/or treatment of one or more diseases. The drug can be cytostatic, cytotoxic, immunosuppressive, or any agent that can be used for treatment purpose. For example, binding of EDC to TCR may result in the induction of immunotolerance by the drug or internalization of EDC into APCs may result in APC death (FIG. 21; bottom panel). In some embodiments, immune tolerance occurs by one or more known mechanisms. For example, the drug prevents release of one or more cytokines by the autoimmune B cells, T cells or both, or inhibits cytokine signaling in the autoimmune B cells, T cells or both. Non-limiting examples include clonal deletion, receptor editing, follicular exclusion, and anergy. In some embodiments, the drug inhibits antigen presentation by autoimmune B cells to T cells. In some embodiments, the drug inhibits one or more signaling pathways. Non-limiting examples include of IL-6 receptor signaling, NF-κB signaling, Toll-like receptor signaling, B cell receptor signaling, T cell receptor signaling, and inflammasome signaling. In some embodiments, one or more targets in the one or more signaling pathways may be targeted by the drug. Non-limiting examples include COX, CCR, histamine receptor, interleukin receptor, gp120/CD4, CXCR, PD-1/PD-L1, MALT, LTR, ROS, NOS, TLR, NADPH-oxidase, and Nrf2.

Non-limiting examples of drugs include Duocarmycin A, Duocarmycin B1, Duocarmycin B2, Duocarmycin C1, Duocarmycin C2, Duocarmycin D, Duocarmycin SA, CC-1065, adozelesin, bizelesin, carzelesin, Cyclophosphamide, Rapamycin, methotrexate, 5-fluorouracil, Doxorubicin, cyclophosphamide, Epirubicin, cisplatin, 5-fluorouracil or capecitabine, Monomethyl auristatin E (MMAE), anthracyclines, oxaliplatin, or bortezomib.

In some embodiments, the EDC can be based on an immunotoxin, which is an antibody-based targeting domain fused to a bacterial toxin for cell killing (Alewine, C., et al, The Oncologist, Vol. 20, pp. 176-185, 2015, which is hereby incorporated by reference in its entirety). Immunotoxin-based EDCs can kill cells by inhibiting protein synthesis and can target both dividing and non-dividing cells.

A drug can be a detection reagent, for example, fluorophores. Non-limiting examples include FITC, Hydroxycoumarin, Aminocoumarin, Methoxycoumarin, Cascade Blue, Pacific Blue, Pacific Orange, Lucifer yellow, NBD, NBD-X, R-Phycoerythrin (PE), PE-Cy5 conjugates, PE-Cy7 conjugates, Red 613 (PE-Texas Red), Peridinin chlorophyll protein (PerCP), TruRed (PerCP-Cy5.5 conjugate), FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), and APC-Cy7 conjugates.

In some embodiments, FACS and/or microscopy-based assays can be designed for screening and identifying small molecules that can be used as the drug in the EDC. In some embodiments, a FACS-based assay (based on Example 1) can be used to screen one or more commercially available libraries of small molecules and identify small molecules that can be used as the drug in the EDC. In some embodiments, a microscopy-based assay (based on Example 2) can be used to screen one or more commercially available libraries of small molecules and identify small molecules that can be used as the drug in the EDC.

In some embodiments, the drug can be one or more of a chemical, a reagent, a protein or a peptide that can induce autoimmune cell death. In some embodiments, the drug can be one of more of antisense RNA, miRNA, siRNA or RNA fragment for RNAi that can interfere with antibody mRNA stability, turnover, and/or translation in the B cells. In some embodiments, the drug is a cytotoxic drug and has a cytotoxic effect on the B and T cells that result in cell death. In some embodiments, cell death occurs by one or more of programmed cell death, apoptosis, macroautophagy, autophagy, necrosis, necroptosis, mitotic catastrophe, activation-induced cell death, anoikis, cornification, excitotoxicity, ferroptosis, Wallerian degeneration, and immunogenic apoptosis.

Once the EDC binds to the antigen-specific receptor on the memory B cell surface, the protein complex is internalized via endocytosis, and subsequently the conjugated drug is released that triggers cellular effects. When the EDC binds to the antigen-specific receptor on the helper T cell surface, it induces cellular effects. Non-limiting examples of cellular effects include, cell growth arrest, cell death, apoptosis, autophagy, immune tolerance, etc. In come embodiments, the EDC is internalized by an APC. In some embodiments, an EDC internalized by an APC prevents the APC from presenting the antigens to T cells.

The interaction between EDC and BCR/TCR can be expressed in terms of "affinity," which can be defined as the strength of binding of a single EDC to its receptor. Affinity is expressed as the equilibrium dissociation constant ($K_D$), which is the concentration at which equilibrium exists between the rate of binding of the EDC to its receptor and the rate of dissociation of the EDC from the receptor. A smaller $K_D$ value means a higher affinity and vice versa.

In some embodiments, affinity of EDC for BCRs and TCRs can range from about $10^{-7}$ to about $10^{-13}$. In some embodiments, the affinity can range from about $10^{-4}$ to about $10^{-10}$. In some embodiments, the affinity can range from about $10^{-9}$ to about $10^{-15}$. In some embodiments, affinity can range from about $10^4$ to about $10^{-10}$. In some embodiments, affinity is about $10^{-3}$, $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, $10^{-15}$, $10^{-16}$, $10^{-17}$, or $10^{-18}$, or a value within a range defined by any two of the aforementioned values.

In some embodiments, more than one EDC can be used in combination. In some embodiments, more than one EDC can be used, in which case a potentiated effect on autoimmune cells is observed. The potentiation can be additive or synergistic. A synergistic effect is greater than an additive effect. An additive effect is observed when the potentiation is equal to the sum of the individual effects of the different EDCs. A synergistic effect is observed when the potentiation is greater than the sum of the individual effects of the different EDCs. Synergistic effect, additive effect or both can be occur human patients, non-human patients, non-patient human volunteers, in vivo models, ex vivo models, in vitro models, etc. Potentiation can range from about <1 to about 100 fold. In some embodiments, the synergistic effect is about 3 to about 30 fold. In some embodiments, the potentiation ranges from <1, 1, >1, 2, 3, 4, 5, 6, 7, 8, 9, 10, 20, 30, 40, 50, 60, 70, 80, 90, or 100 fold, or within a range defined by any two of the aforementioned values.

Owing to the specificity of the epitope for BCRs and TCRs, EDCs specifically target only the disease-causing autoimmune cells (e.g., antigen-specific B and T cells) without affecting the function of the normal immune cells. Thus, the platform according to the present disclosure only targets the specific repertoire of the disease-causing autoimmune cells with no/minimal side effects or without significant side effects. Thus, disease progression and relapses are mitigated resulting in long-lasting protective effects.

The EDC can be of any molecular size range. For example, in some embodiments, the size can range from about 2.5 kDa to about 75 kDa. In some embodiments, the size can range from about 50 kDa to about 500 kDa. In some embodiments, the size can range from about 250 kDa to about 2500 kDa. In some embodiments, the size can be about 2.5, 5, 10, 25, 50, 100, 250, 500, 750, 1000, 1250, 1500, 1750, 2000, 2250, or 2500 kDa, or a value within a range defined by any two of the aforementioned values.

Figure 22:
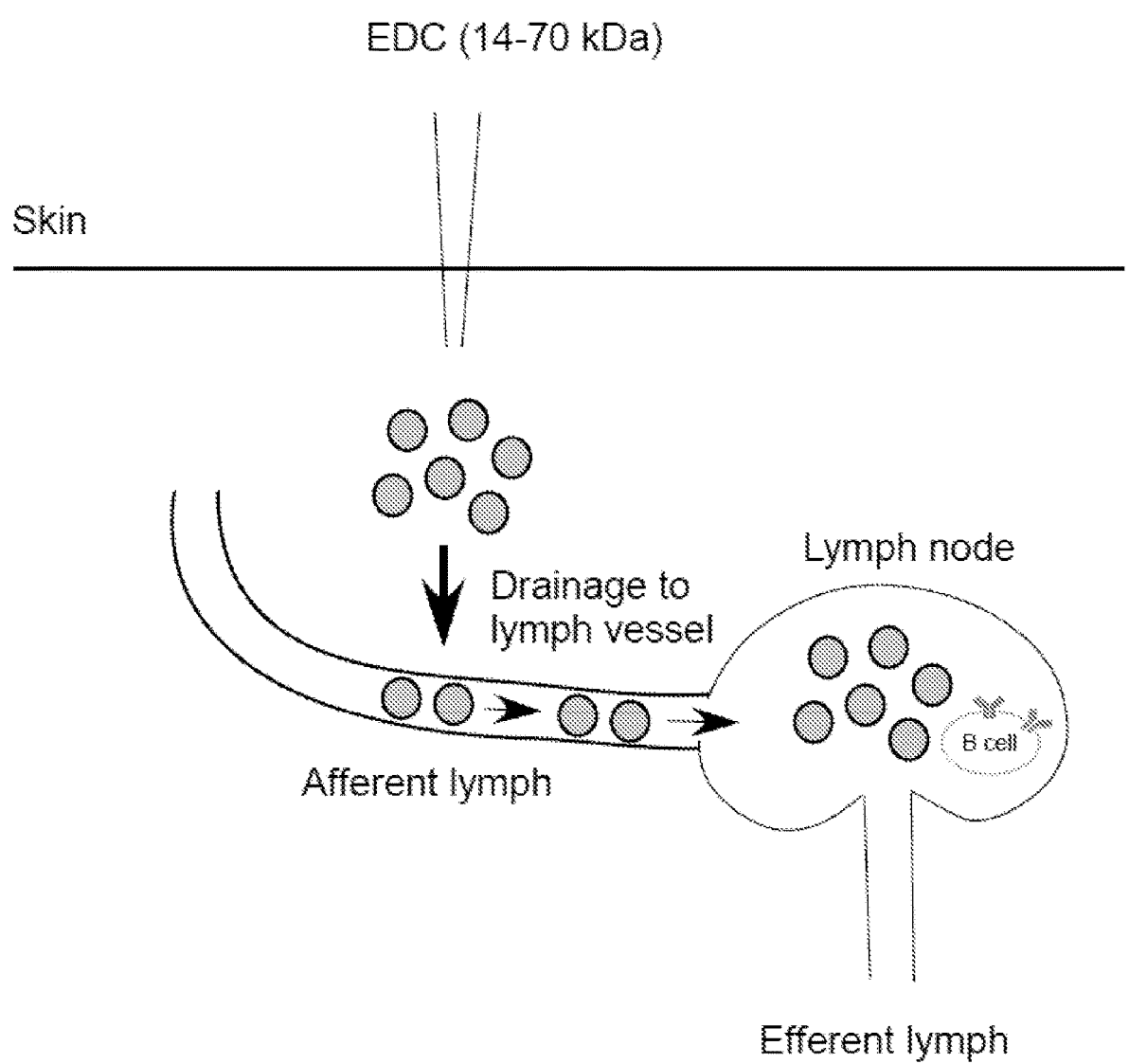
FIG. 22 shows a schematic of delivery of EDC to memory B cells residing in the peripheral lymph nodes.

FIG. 22 shows a schematic of delivery of EDC to memory B cells residing in the peripheral lymph nodes. In order to efficiently deliver EDC to patients and to achieve maximal access of EDC to the memory B cells, EDCs according to the present disclosure are designed in the molecular range of about 14 kDa to about 70 kDa. When the molecular size of EDC is within a range of about 14 kDa to about 70 kDa, the EDC can be drained directly to the afferent lymph when administrated via subcutaneous and/or intradermal routes (Pape, K. A., et al; Roozendaal, R., et al). Thus, in some preferred embodiments, the size of EDC ranges from about 14 kDa to about 70 kDa. In some preferred embodiments, the size of EDC is about 10, 15, 20, 25, 30, 35, 40, 45, 50, 55, 60, 65, 70, 75 kDa, or a value within a range defined by any two of the aforementioned values.

When delivered via the subcutaneous and/or intradermal routes, EDC in the size range of about 14 kDa to about 70 kDa drains directly to the afferent lymph (FIG. 22). Thus, in some more preferred embodiments, the route of administration of EDC in the size range of about 14 kDa to about 70 kDa is subcutaneous, intradermal or both to deliver them directly to the afferent lymph.

When delivered via the subcutaneous and/or intradermal routes, EDC in the size range of about 14 kDa to about 70 kDa drains directly to the afferent lymph, and encounters and binds to memory B cells in the lymph nodes directly without the help of antigen presenting cells (FIG. 22). Therefore, in some more preferred embodiments, the route of administration of EDC in the size range of about 14 kDa to about 70 kDa is subcutaneous, intradermal or both to deliver them directly to the afferent lymph and deliver them to directly to memory B cells in the lymph nodes without the help of antigen presenting cells.

In some preferred embodiments, EDCs within a molecular weight range of about 14 kDa to about 70 kDa can be quickly drained to the lymph nodes to target the antigen-specific memory B cells (and T cells) when delivered via the subcutaneous and/or intradermal routes. However, EDCs can be delivered to patients via all possible delivery routes depending on need. For example, in some embodiments, EDC administration via one or more of topical, parenteral, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intramuscular, intrapleural, intraprostatic, intrapulmonary, intrarectal, intrarenal, intraretinal, intraspinal, intrasynovial, intrathecal, intrathoracic, intrauterine, intravesical, intralesional, bolus, vaginal, rectal, buccal, sublingual, intranasal, or transdermal routes is contemplated.

In some patients, the levels of circulating autoantibodies are high, for example, patients with active autoimmune disease. During active disease, autoantibodies are present in the patient's circulation and the patient is experiencing the effects of the disease. The circulating autoantibodies can neutralize the effects of an EDC, especially when administered intravenously, by binding to the epitope in the EDC. In addition, the autoantibodies may form immune complexes with EDCs resulting in unwanted side-effects. Thus, in some embodiments, especially during active disease state and/or when high levels of autoantibodies are present in the subject's circulation, the preferred route of administration is one or more of subcutaneous, intradermal, or oral. In such patients, the subcutaneous and/or intradermal routes of delivery minimize the chance of EDC neutralization by the autoantibodies and maximize the chance of EDC reaching the memory B cells (and T cells) in the lymphoid tissues and/or organs (FIG. 22). Once the active disease stage has passed and the patient is in a state of remission with low levels of circulating antibodies, the patient can be given EDC via the intravenous route to target the autoimmune cells that are circulating the peripheral in addition to administering of the EDC via the intradermal and/or subcutaneous routes.

However, in some patients, it may be necessary to administer EDC via a combination of routes (e.g., Pemphigus vulgaris). In such patients, the EDC is delivered after the titers of autoantibodies in patient circulation are decreased. For example, after the titers of autoantibodies in patient circulation are decreased, the EDC can be delivered in a combined approach of intradermal, subcutaneous and intravenous routes.

In some embodiments, a patient's active disease is managed via alternative therapies until circulating autoantibody levels naturally reduce based on antibody half-life due to recycling, degradation, or both, following which the EDC is administered. In situations where the patient's active disease has been managed by alternative therapies, the EDC may be administered via a one or more of intradermal, subcutaneous, oral, or intravenous routes.

In some embodiments, EDC can be delivered to patients who were administered alternative therapies and are in remission. In such situations, EDC can be administered to eliminate any lingering populations of disease-causing memory B cells and T cells and thus prevent potential future disease relapses.

In some embodiments, the drug development platform according to the present disclosure can be used to diagnose, prevent and/or effectively treat any T cell and B cell-mediated autoimmune disease. In some embodiments, the drug development platform according to the present disclosure can be used to diagnose, prevent and/or effectively treat any antigen-specific autoimmune disease, including but not limited to, Addison's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss, Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multiple sclerosis, Myasthenia gravis, Myositis, Narcolepsy, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, *Polyarteritis nodosa*, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, Wegener's granulomatosis (or Granulomatosis with Polyangiitis (GPA)).

In some embodiments, diagnosis, prevention and/or treatment of other immune diseases are contemplated including those in which the function of one or more immune cells is skewed resulting in immune system disease that is not necessarily an autoimmune disease. Thus, the drug development platform herein can also be used to diagnose, prevent, and/or effectively treat diseases that are not autoimmune diseases. In preferred embodiments, human autoimmune diseases are targeted by the platform. In some embodiments, autoimmune diseases of non-humans are targeted. Non-limiting examples of non-humans include dogs, cats, rabbit, mouse, guinea pig, monkey, cow, sheep goat, and zebra. In some embodiments, immune system diseases that are non-autoimmune diseases in human and non-humans are targeted by the platform of the present disclosure.

In some embodiments, the patient has had an autoimmune disease for about 1 month to about 5 years. In some embodiments, the patient has had an autoimmune disease for about 1, 2, 3 or 4 weeks, or within a range defined by any two of the aforementioned values, or 2, 3, 4, 5, 6, 7, 8, 9, 10, 11, 12 months, or within a range defined by any two of the aforementioned values, or 2, 3, 4, 5, 6, 7, 8, 9 or 10 years, or within a range defined by any two of the aforementioned values.

In some embodiments, the patient has previously not received any treatment for an autoimmune disease. In some embodiments, the patient has previously received treatment (either immunosuppressive drugs or steroid hormones or both) for an autoimmune disease. In some embodiments, the patient has previously been successfully treated with either immunosuppressive drugs or steroid hormones or both for an autoimmune disease. In some embodiments, the patient has previously been successfully treated with either immunosuppressive drugs or steroid hormones or both for an autoimmune disease, however, the autoimmune disease has relapsed. In some embodiments, the patient has previously been unsuccessfully treated with either immunosuppressive drugs or steroid hormones or both for an autoimmune disease.

The age of the patient may range from about 20 years to about 95 years. In some embodiments, the age of the patient ranges from about 5 years to about 70 years. In some embodiments, the age of the patient is less than 5 years. In some embodiments, the age of the patient is more than 70 years. In some embodiments, the age of the patient is about 15, 20, 25, 30, 35, 40, 45, 50, 55, 60, 65, 70, 75, 80, 85, 90 or 95 years, or within a range defined by any two of the aforementioned values. In some embodiments, the patient is a male. In some embodiments, the patient is a female.

In some embodiments, the EDC is provided in the form of a composition. In some embodiments, the EDC composition can be formulated for delivery via one or more routes of administration herein. Compositions can be without limitations aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Compositions can be presented in unit-dose or multi-dose sealed containers, such as ampules and vials. Injection solutions and suspensions can be prepared from one or more of sterile powders, granules, capsules and tablets. Other non-limiting compositions such as for aerosol- or nebulizer-based and delivery skin patch-based delivery are also contemplated. In some embodiments, the efficacy of the compositions may be tested in non-patient human volunteers, in vivo models, ex vivo models, in vitro models, before being administered to human patients, non-human patients, or both.

In some embodiments, an EDC is administered daily, weekly, biweekly or monthly. In some embodiments, the EDC is administered 1, 2, 3, 4, 5, 6, 7 or 8 times a day.

In some embodiments, the duration of treatment with an EDC ranges from about 2 weeks to about 4 months. In some embodiments, depending on the severity of the disease, the duration of treatment with an EDC is about 1, 2, 3, 4, 5, 6, 7, 8, 9, 10, 11, 12, 13, 14, 15, 16, 17, 18, 19, 20, 21, 22, 23 or 24 weeks, or within a range defined by any two of the aforementioned values.

In some embodiments, the treatment efficacy of treatment ranges from about 80% to about 95% as determined by the level of circulating autoantibodies and/or the number of epitope-specific immune cells (e.g., B and T cells) in the patient. In some embodiments, the treatment efficacy is about 70, 75, 80, 85, 90, 91, 92, 93, 94, 95, 96, 97, 98, 99 or 100%, or within a range defined by any two of the aforementioned values as determined by the level of circulating autoantibodies and/or the number of epitope-specific immune cells (e.g., B and T cells) in the patient.

In some embodiments, the volume of the EDC composition ranges from about 0.1 ml to about 10 ml. In some embodiments, the volume of the EDC composition ranges from about 0.05 ml to about 100 ml. In some embodiments, the volume the EDC composition is about 0.005, 0.0075, 0.01, 0.025, 0.05, 0.075, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 20, 50, 100, or 150 ml, or within a range defined by any two of the aforementioned values.

Owing to the very high affinity and specificity of EDCs, for example, for BCRs and TCRs, and accessibility to relatively inaccessible locations in the body, in some embodiments, effective treatment of an autoimmune disease is achieved at much lower dose of the drug in the EDC as compared to when the drug in the EDC is administered alone. Additionally, in some embodiments, the duration of treatment required with an EDC is much shorter as compared to when the drug in the EDC is administered alone. For example, in some embodiments, when the drug in the EDC is an anti-cancer/anti-tumor drug, the starting dose of EDC is about $1/10^{th}$ of the dose at which the drug in the EDC is used for solid tumor treatment.

As EDCs have much better access to BCR in peripheral circulation and peripheral lymphoid tissues/organs, the starting dose of the drug in the form of EDC can be much lower than what the dose for the drug would be on its own (e.g., for tumors/cancers in relatively inaccessible locations in the body). For example, the starting dose of the drug in the form of EDC can be about $1/5^{th}$, $1/10^{th}$, $1/15^{th}$, $1/20^{th}$, $1/25^{th}$, $1/30^{th}$, $1/35^{th}$, $1/40^{th}$, $1/45^{th}$, $1/50^{th}$, $1/55^{th}$, $1/60^{th}$, $1/65^{th}$, $1/70^{th}$, $1/75^{th}$, $1/80^{th}$, $1/85^{th}$, $1/90^{th}$, $1/95^{th}$, $1/100^{th}$, $1/200^{th}$, $1/250^{th}$, $1/500^{th}$, $1/1000^{th}$, $1/2000^{th}$ or $1/5000^{th}$, or within a range defined by any two of the aforementioned values, of the dose at which the drug in the EDC would be is used for treatment of the disease.

In some embodiments, the one or more EDC-based treatment options provided herein are rapidly effective, require a much lower dose and cause minimal adverse effects as compared to treatment with immunosuppressive drugs and/or steroids.

In some embodiments, a unit dose of EDC can range from about 0.001 mg/kg to about 5 mg/kg. In some embodiments, a unit dose of EDC can range from about 0.01 mg/kg to about 50 mg/kg. In some embodiments, a unit dose of EDC for targeting B cells can range from about 0.001 mg/kg to about 50 mg/kg. In some embodiments, a unit dose of EDC for targeting T cells can range from about 0.001 mg/kg to about 50 mg/kg. In some embodiments, a unit dose of EDC can is about 0.001, 0.01, 0.1, 0.5, 1, 2.5, 5, 7.5, 10, 15, 20, 25, 30, 35, 40, 45, or 50 mg/kg, or a value within a range defined by any two of the aforementioned values.

In some embodiments, the EDC is administered as a single daily dose. In some embodiments, the EDC is administered as more than one dose per day. In some embodiments, the number of doses per day ranges from one to six. In some embodiments, the number of doses per day is 1, 2, 3, 4, 5, 6, 7, or 8.

In some embodiments, the EDCs herein can be used to remove and/or eliminate circulating autoimmune cells during plasmapheresis, apheresis, and leukoreduction.

Diagnosis and Post-Treatment Patient Monitoring

Disease diagnosis and monitoring post-treatment disease progression are critical to ascertaining patient treatment options, patient response to treatment, and patient disease management.

In some instances, diagnosis and post-treatment patient monitoring of disease progression are performed using painful and invasive methods. For example, diagnosis and post-treatment patient monitoring of membranous nephropathy (MN) progression relies entirely on kidney biopsies, which are invasive and may cause severe kidney bleeding and many other side effects.

In some embodiments, provided herein are EDCs for non-invasive and/or minimally invasive diagnosis and post-treatment monitoring autoimmune diseases.

In some embodiments, the EDCs for non-invasive and/or minimally invasive diagnosis and post-treatment monitoring of autoimmune disease comprise one or more epitopes provided herein. The epitope can be in solution or immobilized on a substrate, or both. The substrate can be any of a variety of substrates such as columns, beads, microspheres, test strips or multi-well plates known to be useful for assays for diagnosis and post-treatment monitoring. In some embodiments, the diagnosis and post-treatment monitoring of autoimmune disease is based on one or more assays. In some embodiments, the assay can be one or more of an immunoassay such as an enzyme-linked immunosorbent assay (ELISA), FACS, Enzyme-Linked ImmunoSpot (ELISPOT), radioimmunoassay, magnetic immunoassay.

In some embodiments, one or more epitopes provided herein can be attached to a substrate (e.g., an ELISA plate) using standard procedures. A patient sample (e.g., blood, serum and/or plasma) can be collected during a visit to a clinic using standard clinical procedures. The patient samples can be added to the ELISA plate at different dilutions (e.g., $1/10^{th}$, $1/100^{th}$, $1/1000^{th}$, etc.) with appropriate control samples. After standard incubation, the ELISA plate can be read using a standard plate reader.

In some embodiments, there is a detectable increase in anti-epitope autoantibodies in the patient sample relative the control sample. In some embodiments, a detectable increase in anti-epitope autoantibodies by at least 10% relative to the control sample indicates the presence of an autoimmune disease in the patient. In some embodiments, the detectable increase in anti-epitope autoantibodies in the patient sample is greater than 10% relative to the control sample. In some embodiments, the detectable increase in anti-epitope autoantibodies in the patient sample ranges from about 5% to about 15% relative to the control sample. In some embodiments, the detectable increase in anti-epitope autoantibodies in the patient sample is about 1, 2.5, 5, 7.5, 10, 15, 20, 25, 30, 35, 40, 45, 50, 55, 60, 65, 70, 75, 80, 85, 90, 95, or 100% relative to the control sample, or within a range defined by any two of the aforementioned values.

In some embodiments, there is a detectable increase in anti-epitope autoantibodies in the patient sample relative to a control sample. The increase in anti-epitope autoantibodies in a patient sample is detectable using one or more of the composition, methods and/or kits for diagnosis provided herein. As used herein, "control sample" refers to a sample that is either representative of normal levels of anti-epitope autoantibodies, or obtained from a subject known to be free of the autoimmune disease.

In some embodiments, the patient sample can be, for example, a bodily fluid (e.g., one or more of blood, plasma, serum, urine, cerebrospinal fluid, and lymph), a biopsy sample of a tissue and/or an organ affected by an autoimmune disease. For example, in some embodiments, a kidney biopsy may be performed in a patient with MN. In some embodiments, a biopsy of a mucocutaneous lesion may be performed in a patient with Pemphigus vulgaris.

A microscopy-based assay for diagnosis and post-treatment monitoring of an autoimmune disease can comprise obtaining patient blood samples. Using one or more EDCs herein, the blood sample can be analyzed as is or one or more specific populations of cells (e.g., total B cells or total T cells) may be isolated using one or more cell purification techniques (e.g., FACS) known in the art prior to analysis for the presence of autoimmune cells in the patient. For example, one or more EDCs herein can be used to detect the presence of autoantibody-producing B cells in the patient sample (Example 5; FIG. 24, and Example 8; FIG. 29). One or more EDCs herein can also be used for detecting the levels of autoantibodies in a patient.

In some embodiments, the assay can also be adapted for monitoring the status of an autoimmune disease in a patient and/or responsiveness to one or more of the treatment options provided herein. For example, a blood, serum and/or plasma sample can be collected from a patient at a first time point. The first time point can be a patient's, first visit to the clinic and the patient has not been diagnosed with an autoimmune disease and has never been previously treated for the autoimmune disease.

In some embodiments, the first time point can be before the initiation of one or more treatment options provided herein with the patient having previously undergone other forms of treatment. In some embodiments, after the initiation of one or more treatment options provided herein, a blood, serum and/or plasma sample can then be collected from a patient at a second time point as well as at additional subsequent time points.

In some embodiments, the amount of anti-epitope autoantibody-producing B cells in the patient sample can be compared at the various time points. In some embodiments, a decrease in the amount of autoantibody-producing B cells in the patient sample at the second and/or subsequent time points relative to the first time point is indicative of amelioration of disease. In some embodiments, a decrease in the amount of autoantibody-producing B cells in the patient sample at the second and/or subsequent time points relative to the first time point is indicative of elimination of autoantibody-producing B cells and 100% treatment of the disease. In some embodiments, elimination of autoimmune cells and amelioration of disease can range from about 50% to 100%. In some embodiments, elimination of autoimmune cells and amelioration of disease is about 25, 30, 35, 40, 45, 50, 55, 60, 65, 70, 75, 80, 85, 90, 95, or 100%. In some embodiments, the elimination of autoimmune cells is 100% after just one round of treatment. In some embodiments, when the elimination of autoimmune cells is low after one round of treatment (e.g., below 50%), one or more additional rounds of treatment may be provided to eliminate the autoimmune cells and/or the patient may be administered one or more additional therapies.

In some embodiments, the efficacy of an EDC may be tested in vitro using patient samples prior to administering the EDC to patients. For example, the efficacy of an EDC is tested on isolated B cells from patient peripheral blood mononuclear cells (PBMCs) (FIG. 25; Example 6, and FIG. 30; Example 9). An EDC comprising a fluorophore (e.g., FITC) is used detect the presence of autoantibody-producing B cells in patient samples (left panels in FIG. 25 (MN patient samples) and FIG. 30 (Pemphigus vulgaris patient samples) prior to exposing the samples to an EDC comprising a cytotoxic drug. The patient samples are then treated with an EDC comprising a cytotoxic drug (e.g., MMAE). The EDC comprising the fluorophore is then used determine the efficacy of the EDC comprising a cytotoxic drug of autoantibody-producing B cells in patient samples (middle panels in FIG. 25 (MN patient samples) and FIG. 30 (Pemphigus vulgaris patient samples)).

Figure 25:
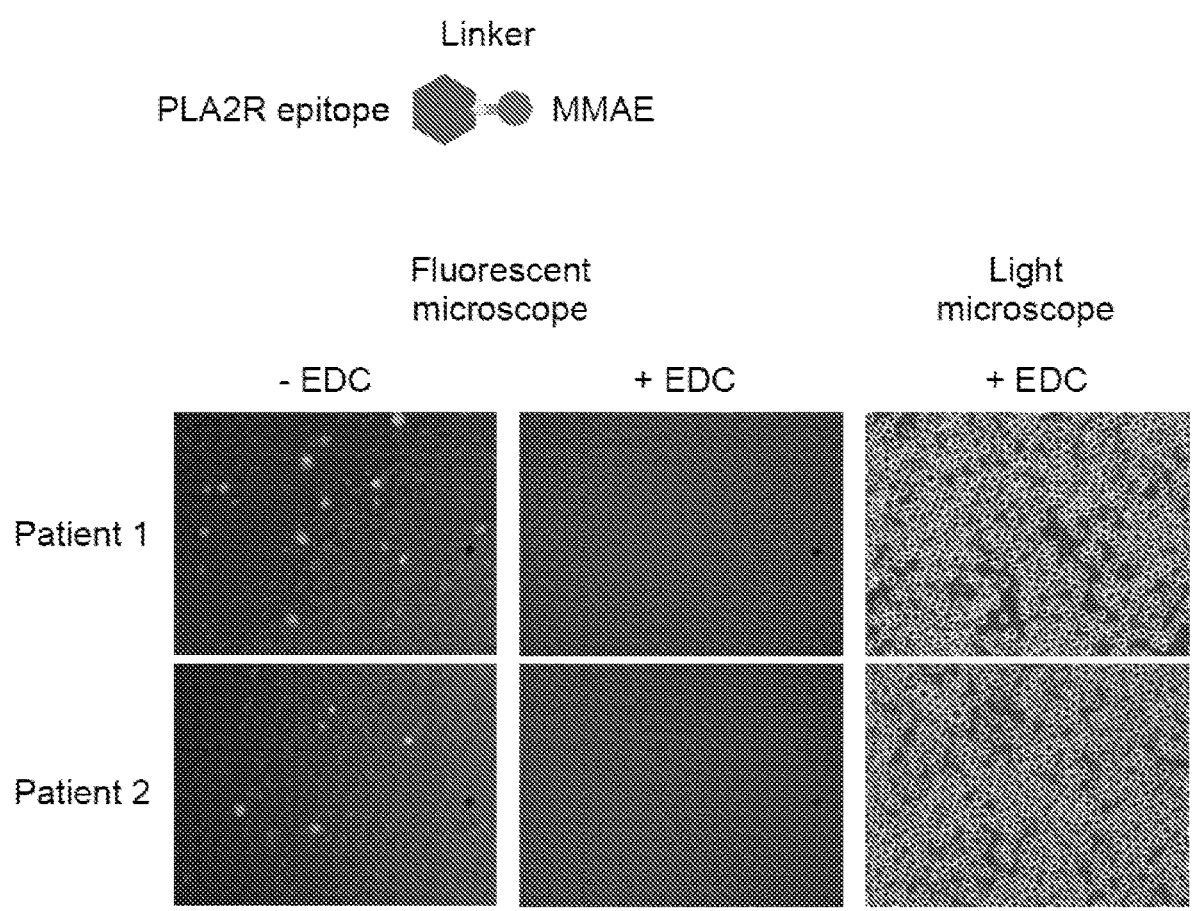
FIG. 25 shows the effect of PLA2R-epitope-MMAE conjugate on B cells isolated from PLA2RAb positive PMN patients.

In some embodiments, the efficacy of the EDC comprising a cytotoxic drug in eliminating patient autoantibody-producing B cells is 100% (middle panels in FIG. 25 (MN patient samples) and FIG. 30 (Pemphigus vulgaris patient samples)). In some embodiments, the efficacy ranges from about 50% to 100%. In some embodiments, the efficacy is about 25, 30, 35, 40, 45, 50, 55, 60, 65, 70, 75, 80, 85, 90, 95, or 100%. In some embodiments, when the efficacy after a first round of treatment is not 100%, one or more additional rounds of treatment can be performed and a reassessment of efficacy can be performed after each round of treatment.

In some embodiments, the one or more EDCs comprising a fluorophore are used as diagnostic tools to determine the number of epitope specific cells in a patient. For example, FIG. 24 shows the use of an EDC based on PLA2R epitope and FITC as a diagnostic tool for determine the presence of autoimmune B cells in the peripheral circulation of patients with MN. FIG. 29 shows the use of an EDC based on Dsg epitope and FITC as a diagnostic tool for determine the presence of autoimmune B cells in the peripheral circulation of patients with PV.

In some embodiments, the one or more EDCs comprising a fluorophore are used as diagnostic tools to determine the number of epitope specific autoimmune cells in a patient at a first time point. If the number of epitope specific autoimmune cells in the patient at a first time point is above a predetermined threshold (indicating that the patient requires one or more therapies for the disease), the patient is administer one or more EDCs comprising a drug either by itself or in combination with one or more adjunct therapies. The number of epitope specific autoimmune cells is reassessed at a second time using the one or more EDCs comprising a fluorophore. If the number of epitope specific autoimmune cells at the second time point is below the predetermined threshold, the treatment is discontinued. If the number of epitope specific autoimmune cells at the second time point is above the predetermined threshold, the treatment is continued and a subsequent assessment performed.

The presence of autoimmune cells in a patient can be detected in blood, other biological fluids, and tissue and organ biopsies (e.g., collected during surgery). The EDCs can be used to detect any cell population that can bind an epitope (e.g., B cells, T cells, other cells in PBMCs, and cells in other biological fluids).

In some embodiments, the platform herein can be adapted to any peptide, protein domain, small molecules, and other ligands (e.g., ligand domains or peptide ligands that bid specific receptors).

In some embodiments, the level/numbers of autoantibody-producing B cells in the patients can be calculated using standard automated computer programs. In some embodiments, the level of autoantibody-producing B cells can be compared before and after treatment with one or more treatment options provided herein. In some embodiments, one or more epitopes provided herein can be produced and purified in large quantities, and standard commercial grade ELISA plates can be manufactured and used as a routine procedure for diagnosing and post-treatment patient monitoring in a clinical laboratory.

In some embodiments, the assay is non-invasive and/or minimally invasive, simple, time efficient, cost effective and can be performed routinely in a clinical laboratory. For example in some embodiments, the assay can be performed without the need for an invasive kidney biopsy as used for MN patients.

In some embodiments, a PLA2R epitope-specific ELISA assay can be designed for screening and identifying small molecules for MN treatment. For examples, in some embodiments, small molecules can be identified that specifically block the binding of PLA2R autoantibodies to PLA2R. For example, an embodiment of the ELISA plate provided herein can be used to screen one or more commercially available libraries of small molecules.

In some embodiments, the one or more commercially available libraries of small molecules can comprise without limitation metabolites (e.g., of alkaloids, glycosides and lipids), peptides, natural phenols (e.g., flavonoids), polyketides, terpenes, steroids and tetrapyrroles.

In some embodiments, any of the composition and/or methods described herein is provided as one or more kits. The kit can comprise one or more polypeptides, antibodies, probes and or other assay reagents described herein. The kit can include the solid support to which assay reagents may be bound or immobilized. The reagents can optionally be labelled with a detectable marker. The kit can further comprise one or more containers for containing, storing and/or transporting the polypeptides, antibodies, probes and other reagents described herein.

In some embodiments, the compositions, methods, and/or kits that specifically target and eliminate epitope-specific immune cells (e.g., B and T cells) are provided. In some embodiments, one or more patients are selected and treated using the compositions, methods, and/or kits provided herein to specifically target and eliminate epitope recognizing immune cells (e.g., B and T cells) from the patient.

Membranous Nephropathy (MN)

Membranous Nephropathy (MN) (also referred to as primary MN or idiopathic MN) is a common glomerular disease. Incidence of MN is high in patients over the age of 40. Frequent disease relapse is the major challenge of clinical treatment. There are no effective treatments except to use high dose of steroid hormones and immunosuppressant and patients progress to kidney failure in 5-10 years under current management. There are 4,000-6,000 new cases/year in US, 10,000 new cases/year in Europe, and 80,000 new cases/year worldwide.

MN is an autoimmune glomerular disease. The disease causing mechanism of MN was recently determined to be due to binding to a membrane receptor, phospholipase A2 receptor (PLA2R) on the surface of the kidney podocytes of circulating autoimmune antibodies (autoantibodies) generated by autoantibody-producing B cells. Over 70% patients are caused by anti-PLA2R autoantibodies. MN often relapses leading to kidney failure in 5-10 years.

Current clinical treatments for MN use either immunosuppressive drugs (e.g., Cyclosporine, Rituximab, Chlorambucil, Tacrolimus, Cyclophosphamide, Mycophenolate mofetil) or steroid hormones (e.g., corticosteroids). However, both of these treatment options are non-specific and produce significant side effects. Often disease relapse occurs when the dose of these treatments are reduced. Moreover, in many patients these treatments are not effective. Therefore, there remains a strong need for a specific treatment for the MN without harmful side effects.

The disease causing mechanism of MN was recently determined to be due to circulating autoantibodies binding to PLA2R on the surface of the kidney podocytes. Additionally, polymorphisms M292V and H300D in C-type lectin-like domain 1 (CTLD1) and G1106S in the linker region between CTLD6 and CTLD7 may correlate to the occurrence of MN in patients (Kao, L., et al.).

The level of the antibody in the plasma of patients with MN is directly correlated with the severity of the disease and a patient's response to the medical treatment. Thus, there is a need to remove autoantibody-producing B cells from the patient to treat the disease while simultaneously avoiding harmful side effects.

Figure 1:
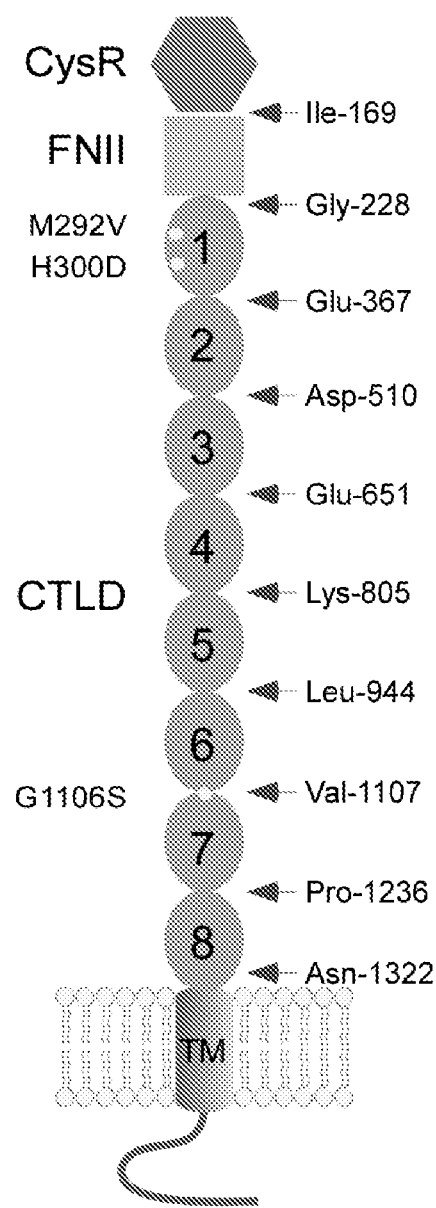

PLA2R is a large integral membrane protein with a molecular weight of about 180-185 kDa (SEQ ID NO: 14). A proposed topology of PLA2R based on the mannose receptor is provided in FIG. 1. PLA2R contains a large glycosylated extracellular portion that interacts with ligand, a single transmembrane domain and a short cytoplasmic tail (FIG. 1). The large extracellular portion can be further divided into 10 domains: a cysteine rich domain (CysR), a fibronectin-like type II domain (FnII), and 8 repeated C-type lectin-like domains (CTLD) in tandem (FIG. 1).

FIG. 1 indicates the position of amino acids demarcating the various domains (indicated by arrows) of PLA2R. The amino acids sequences of some of the domains are provided in SEQ ID NO: 7—SEQ ID NO: 12 (FIG. 12-FIG. 17). The PLA2R epitope (SEQ ID NO: 13), which is recognized by autoantibodies in MN patients, is located in the extracellular portion of the receptor, is conformational and sensitive to reduction, and has a very high affinity for the autoantibodies.

However, the PLA2R epitope (FIG. 18; SEQ ID NO: 13) when expressed on its own does not fold properly into the correct conformation. Inclusion of the first two domains allows for proper conformational folding of the antigen. The full-length PLA2R protein (FIG. 19; SEQ ID NO: 14) also cannot be expressed and purified in large scale as it is not biochemically stable. However, domains 1-3 domain and up to domains 1-6 are suitable for expressing and obtaining large amounts of protein. Domains 1-5 provide for optimal protein expression. For example, properly folded conformation can be obtained by using the sequence provided in SEQ ID NO: 9.

The production of anti-PLA2R autoantibodies in MN patients is due to activation and expansion of a specific B cell population that carries specific BCRs that recognize an epitope in PLA2R. The specific B cell population is activated when engaged by a specific helper T cell population that carries a T cell receptor specific for the same PLA2R epitope. These specific B and T cells represent only a small fraction of the total repertoire of B and T cells.

Treating MN by Targeting B and T Cells

Removing the anti-PLA2R autoantibodies from patients may alleviate the pathological effects of the autoantibodies. However, removing autoantibodies from a patient still leaves the patient vulnerable to disease relapse. This is because the PLA2R autoantibody-producing B cells continue to produce the autoantibodies despite removal of disease-causing autoantibodies from the patient blood. Therefore, specifically targeting PLA2R-epitope recognizing immune cells (e.g., B and T cells) can eliminate the pathogenic autoantibody production without affecting the normal function of other immune cells.

In some embodiments, the compositions, methods, and/or kits specifically target and eliminate PLA2R-epitope recognizing immune cells. In some embodiments, the compositions, methods, and/or kits specifically target and eliminate PLA2R-epitope recognizing B cells. In some embodiments, the compositions, methods, and/or kits specifically target and eliminate PLA2R-epitope recognizing T cells. In some embodiments, the compositions, methods, and/or kits specifically target and eliminate PLA2R-epitope recognizing B and T cells. In some embodiments, the EDC comprises one or more PLA2R fragments provided herein, a linker and a drug.

Current treatments for MN are non-specific with significant side-effects and frequent disease relapse. The EDCs herein for MN are specific with minimum/no side-effects, and eliminate disease relapse.

The patient presents at least one clinical symptom of MN. The symptoms of MN include one or more of nephrotic syndrome, edema (swelling in any area of the body), proteinuria, foamy appearance of urine (due to large amounts of protein), urination (excessive at night), fatigue, poor appetite and weight gain.

In some embodiments, the patient has had MN for about 1 month to about 5 years. In some embodiments, the patient has had MN for about 1, 2, 3 or 4 weeks, or 2, 3, 4, 5, 6, 7, 8, 9, 10, 11, 12 months, or 2, 3, 4, 5, 6, 7, 8, 9 or 10 years, or within a range defined by any two of the aforementioned values.

In some embodiments, the patient has previously not received any treatment for MN. In some embodiments, the patient has previously received treatment (either immunosuppressive drugs or steroid hormones or both) for MN. In some embodiments, the patient has previously been successfully treated with either immunosuppressive drugs or steroid hormones or both for MN. In some embodiments, the patient has previously been unsuccessfully treated with either immunosuppressive drugs or steroid hormones or both for MN.

In some embodiments, the patient may be subject to a kidney biopsy to confirm that the patient has MN. In some embodiments, the patient is subject to a kidney biopsy even if there is a detectable increase in anti-PLA2R autoantibodies in the patient sample relative to the control sample. In some embodiments, the patient is not subject to a kidney biopsy if there is a detectable increase in anti-PLA2R in the patient sample relative to the control sample.

Figure 2:
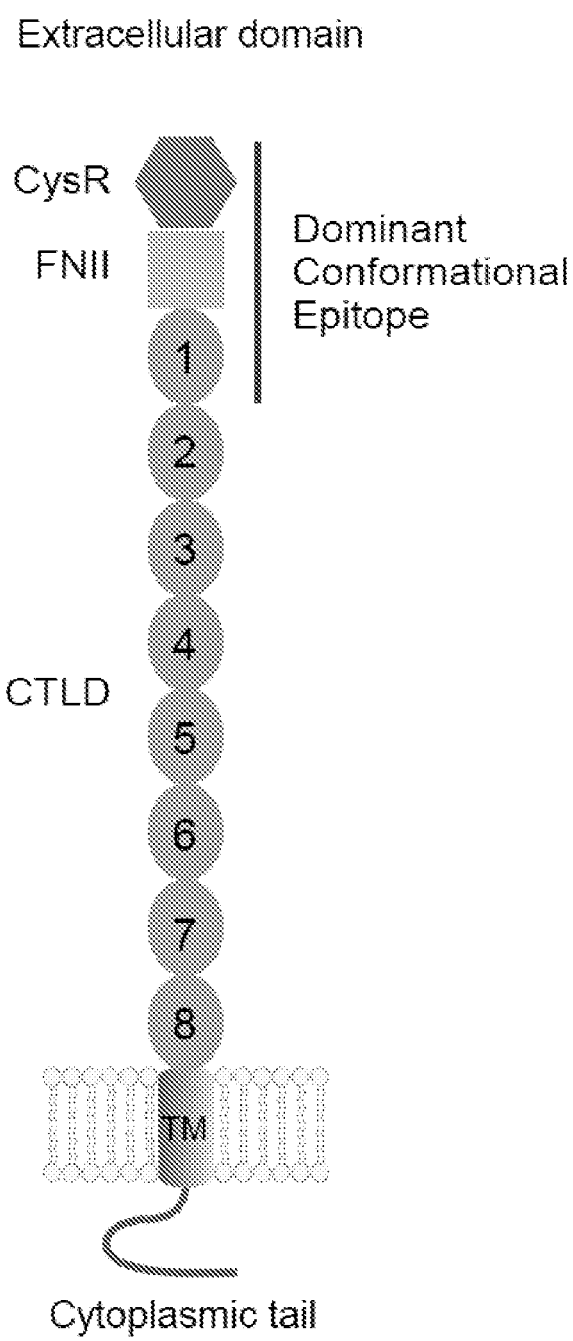

Full-length PLA2R (FIG. 19; SEQ ID NO: 14) is difficult to purify and therefore has limited application in clinical settings. Thus, in some embodiments, the compositions, methods, and/or kits for removing autoantibody-producing B cells from a patient sample comprise a purified fragment of full-length PLA2R. In some embodiments, the fragment comprises CysR, FnII and one or more CTLDs (FIG. 2).

In some embodiments, the fragment comprises at least domains 1-5 of PLA2R. In some embodiments, the sequence of the fragment is as provided in SEQ ID NO: 1 (about 658 amino acids in length) (FIG. 6). In some embodiments, the sequence of the fragment is as provided in SEQ ID NO: 2.

In some embodiments, the sequence of the fragment is as provided in SEQ ID NO: 2 (FIG. 7) and about 5% to about 95% of the sequence provided in SEQ ID NO: 3 (FIG. 8). In some embodiments, the sequence of the fragment is as provided in SEQ ID NO: 2 (FIG. 7) and about 5, 10, 15, 20, 25, 30, 35, 40, 45, 50, 55, 60, 65, 70, 75, 80, 85, 90 or 95% of the sequence provided in SEQ ID NO: 3 (FIG. 8).

In some embodiments, the sequence of the fragment is as provided in SEQ ID NO: 4 (about 805 amino acids in length) (FIG. 9). In some embodiments, the sequence of the fragment is as provided in SEQ ID NO: 5 (FIG. 10). In some embodiments, the sequence of the fragment is as provided in SEQ ID NO: 5 (FIG. 10) and about 5% to about 95% of the sequence provided in SEQ ID NO: 6 (FIG. 11). In some embodiments, the sequence of the fragment is as provided in SEQ ID NO: 5 and about 5, 10, 15, 20, 25, 30, 35, 40, 45, 50, 55, 60, 65, 70, 75, 80, 85, 90 or 95% of the sequence provided in SEQ ID NO: 6 (FIG. 11).

Figure 4:
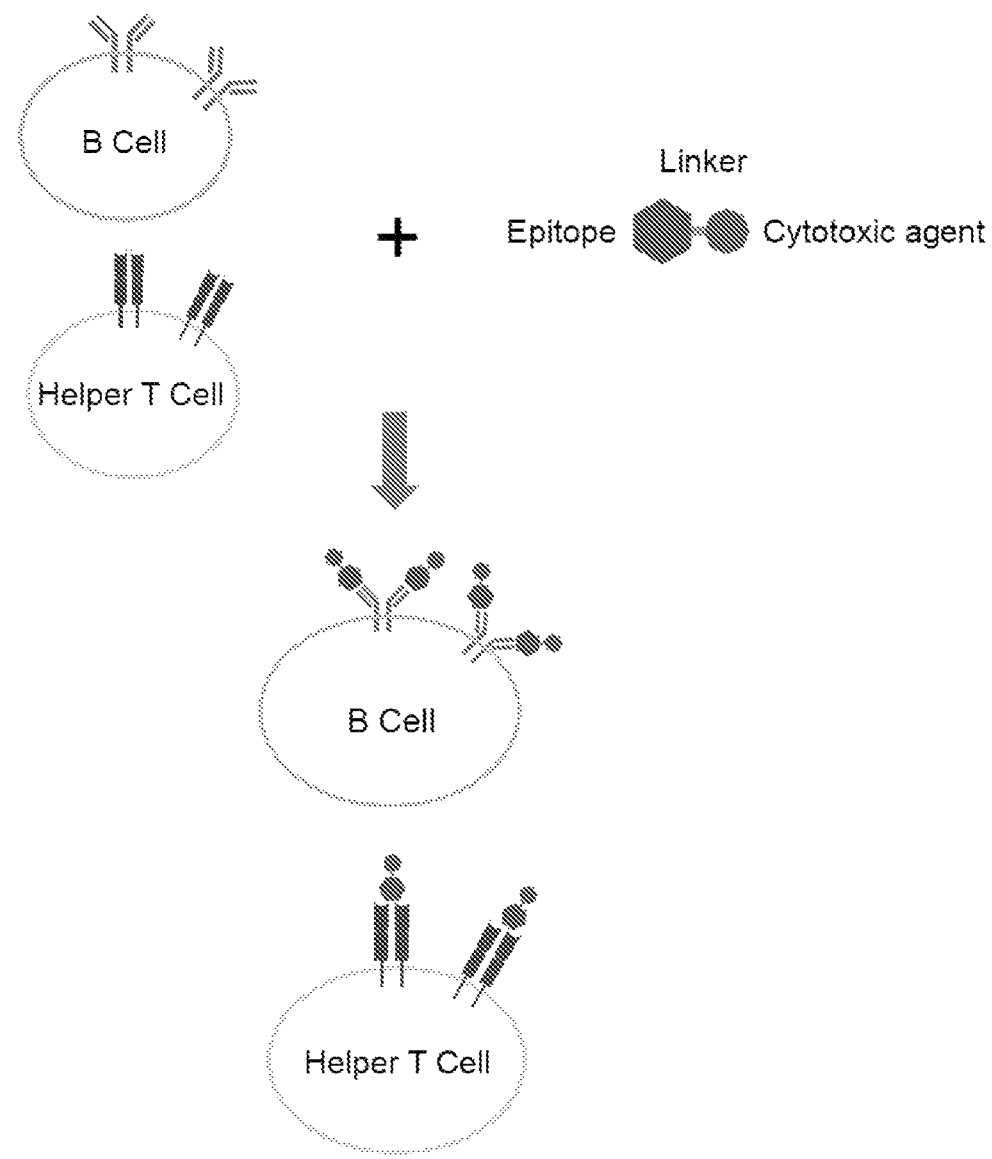

In some embodiments, the compositions, methods, and/or kits specifically target and eliminate PLA2R-epitope recognizing immune cells comprise one or more fragments of PLA2R provided herein as a carrier for one or more drugs (EDC) (FIG. 4). The PLA2R fragments would specifically target the drug to the specific B cells and the corresponding helper T cells that are responsible for anti-PLA2R autoantibody production in patients. The EDC can bind to the specific receptors on the surface B and T cells and enter the cells via endocytosis.

In some embodiments, a free cysteine residue is introduced at the C-terminus of the PLA2R fragment. The thio group of the free cysteine is then conjugated with a cleavable linker. In some embodiments, the cleavable linker is a valine-citrulline linker. In some embodiments, the valine-citrulline linker is pre-conjugated with a drug. In some embodiments, the drug is a duocarmycin analog. In some embodiments, a free cysteine residue is introduced at the C-terminus of the PLA2R fragment and the thio group of the free cysteine is conjugated with a cleavable valine-citrulline linker pre-conjugated with a duocarmycin analog.

In some embodiments, a short sequence of CXPXR is introduced to the C-terminus of the PLA2R fragment. In some embodiments, the cysteine residue is converted to a formylglycine aldehyde tag. In some embodiments, the cysteine residue is converted to a formylglycine aldehyde tag using a formylglycine-generating enzyme. In some embodiments, the formylglycine aldehyde tag is then conjugated to a drug-linker by a non-cleavable linkage. In some embodiments, the formylglycine aldehyde tag is conjugated to the drug-linker by a non-cleavable linkage via oxime chemistry. In some embodiments, the formylglycine aldehyde tag is conjugated to the drug-linker by a non-cleavable linkage via Pictet-Spengler reaction. In some embodiments, the drug in the drug-linker is a cytotoxic reagent.

In some embodiments, a drug is conjugated to the PLA2R fragment in a region outside of the BCR interaction site. In some embodiments, a drug is conjugated to the PLA2R fragment in a region outside of the BCR interaction site to one or more lysine residues. In some embodiments, a drug is conjugated to the PLA2R fragment in a region outside of the BCR interaction site to one or more lysine residues via amide bonds to an N-hydroxysuccinimide (NHS) ester appended to a drug-linker.

Figure 5:
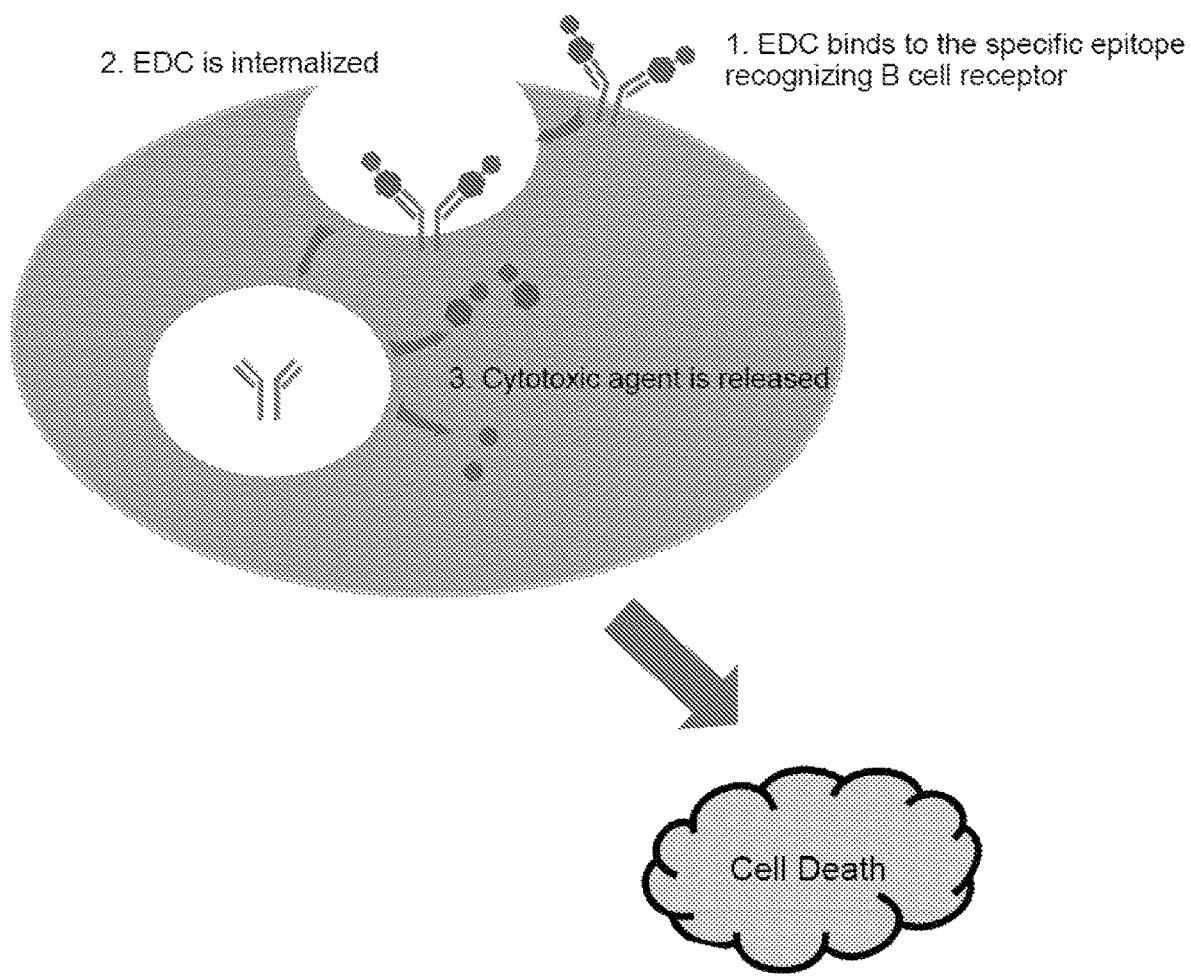

For example, in some embodiments, the EDC is administered into the patient circulation via the intravenous route. In some embodiments, binding of the EDC to the PLA2R-recognizing autoantibody-producing B cells triggers rapid internalization of the receptor-EDC complex via endocytosis (FIG. 5). In some embodiments, binding of the EDC to the PLA2R-recognizing T cells triggers rapid internalization of the receptor-EDC complex via endocytosis. In the endosome, the internalized receptor-EDC complex is digested causing release of the conjugated drug. In some embodiments, the released drug then causes death of the PLA2R-recognizing autoantibody-producing B cells (FIG. 5). In some embodiments, the released drug then causes death of the PLA2R-recognizing T cells. In some embodiments, the drug causes death of the B and T cells by apoptosis. In some embodiments, the drug causes death of the B and T cells by non-apoptotic mechanisms.

Pemphigus Vulgaris

Pemphigus vulgaris (PV) is a potential life-threatening-autoimmune blistering disease characterized by intraepithelial blister formation caused by loss of cell-cell adhesion. PV affects both of the skin and mucous membranes and is mediated by circulating pathogenic autoantibodies directed against keratinocyte cell surface molecules desmoglein 1 (Dsg1) and desmoglein 3 (Dsg3).

The binding of autoantibodies to desmoglein impairs the integrity of desmosome that results in a loss of cell-to-cell adhesion causing blistering, and in addition, triggers a cellular process that results in acantholysis. Patients with the mucocutaneous form of PV have pathogenic anti-Dsg1 and anti-Dsg3 autoantibodies. Patients with the mucosal form of PV have only anti-Dsg3 autoantibodies.

Figure 26:
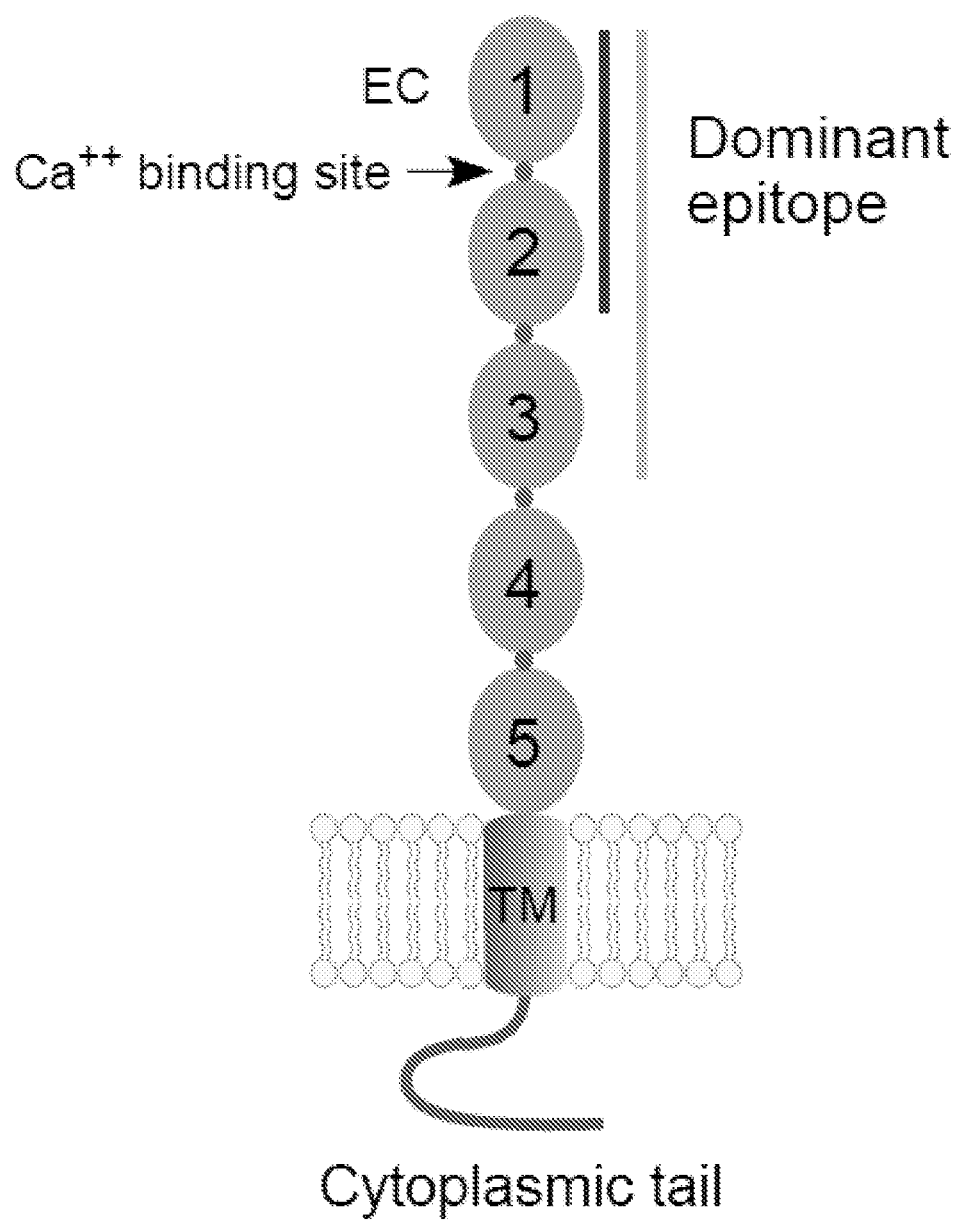
FIG. 26 shows topological folding of desmoglein in the cell membrane. The shorter vertical line indicates the immunodominant epitope region in Dsg1 for autoantibody binding (EC1-2), and the longer vertical line indicates the immunodominant region in Dsg3 for autoantibody binding (EC1-3).

Dsg3 and Dsg1 are both transmembrane proteins with a similar molecular structure, of which each comprises 5 extracellular cadherin (EC) domains, a single-pass transmembrane region, and an intracellular tail (FIG. 26). The dominant epitope in Dsg3 is located in the EC1-3 domains (FIG. 26) that bind to all anti-Dsg3 pathogenic autoantibodies. The Dsg3 EC1-3 domains contain 334 amino acids. The dominant epitope in Dsg1 is located in the EC1-2 domains (FIG. 26) that bind to all anti-Dsg1 pathogenic autoantibodies. and the Dsg1 EC1-2 contains 221 amino acids respectively. The calcium binding sites in the epitopes are critical for autoantibody binding (FIG. 26) (Ohyama, B., et al.).

In some embodiments, EDCs based on epitopes in Dsg1 are provided. FIG. 31 shows the amino acid sequence of an embodiment of an epitope of Dsg1 (SEQ ID NO: 16; 336 amino acids) used for developing Dsg1 epitope-based EDC according to the present disclosure. In some embodiments, EDCs based on epitopes in Dsg3 are provided. FIG. 32 shows the amino acid sequence of an embodiment of an epitope of Dsg3 (SEQ ID NO: 17; 450 amino acids) used for developing Dsg3 epitope-based EDC according to the present disclosure. In some embodiments, EDCs based on epitopes in Dsg1 and Dsg3 are provided.

Schematics of embodiments of EDCs based on epitopes in Dsg1 and Dsg3 are shown in FIG. 27. Development of EDCs based on epitopes in Dsg1 and Dsg3 for treatment of PV is described in Example 7.

In some embodiments, residues that are potentially glycosylated can be substituted using, for example, site directed mutagenesis when using an expression vector to express a Dsg1 fragment or Dsg3 fragment. In some embodiments, when a Dsg1 or Dsg3 protein fragment is directly synthesized, the protein synthesis can be customized such that the potentially glycosylated residues are replaced with non-glycosylated residues that will not affect protein structure and/or conformation for autoantibody recognition.

In some embodiments, additional modifications may be made to the Dsg1 or Dsg3 fragment, for example, to attach a reagent (e.g., a drug) to the Dsg1 or Dsg3 fragment, improve accessibility of the Dsg1 or Dsg3 epitope to receptors on the cell surface, and/or improve protein expression and yield. For example, a Dsg1 or Dsg3 fragment may be modified by inserting small (about 2 to 10 amino acids) N- or C-terminal peptide or both, making conservative and/or non-conservative substitutions, and/or adding one or more heterologous sequences to achieve a desired objective.

In some embodiments, one or more of the Dsg1 or Dsg3 fragments provided herein are encoded by nucleic acids. In some embodiments, the Dsg1 or Dsg3 encoding nucleic acid is a cDNA or an mRNA. In some embodiments, the Dsg1 or Dsg3 encoding nucleic acid can be comprised within a protein expression vector. In some embodiments, the protein expression vector is a DNA vector or an RNA vector. In some embodiments, the protein expression vector is an adeno-associated viral (AAV) vector. In some embodiments, the protein expression vector is a mammalian cell expression vector. In some embodiments, the protein expression vector is an insect cell expression vector. In some embodiments, the Dsg1 or Dsg3 fragment encoding nucleic acid comprised within a protein expression vector is operably linked to regulatory elements to regulate the expression of the PLA2R fragment.

Regulatory elements can include promoters, terminators, enhancers, etc. As used herein, "operably linked" refers to a regulatory element positively or negatively controlling the expression of a protein from a nucleic acid.

One or more of the proteins expression vectors provided herein and others known to one of ordinary skill in the art can be used to obtain large quantities of one or more of the Dsg1 or Dsg3 fragments provided herein for incorporation into one or more of the compositions, methods, and/or kits provided herein.

In some embodiments, the protein expression vector introduces a tag on the encoded Dsg1 or Dsg3 fragment. In some embodiments, the tag is on the N-terminal end. In some embodiments, the tag is on the C-terminal end. In some embodiments, the tag is on both ends. Non-limiting examples of tags include chitin binding protein, maltose binding protein, glutathione-S-transferase, thioredoxin, poly (NANP), FLAG, V5, Myc, HA, NE, biotin, biotin carboxyl carrier protein, GFP, Halo, Nus, Fc, AviTag, calmodulin, poly-Glu, E, S, SBP, Softag 1, Softag 3, Strep, TC, VSV, Ty and Xpress. In some embodiments, the tag is a poly-histidine (poly-His) tag.

In some embodiments, the protein expression vector additionally introduces a cleavage site between the Dsg1 or Dsg3 fragment and the tag. In some embodiments, the cleavage site is a proteolytic site. Non-limiting examples of proteolytic sites include sites for TEV protease, Factor Xa or enteropeptidase. In some embodiments, the proteolytic site is a thrombin cleavage site. Other cleavage sites For example, in some embodiments, a poly-His-tagged Dsg1 or Dsg3 fragment can be expressed in mammalian cells (e.g., HEK 293 cells) and purified from the cell culture medium using Ni-affinity purification. The poly-His tag can then be removed by proteolytic digestion (e.g., using thrombin), and the Dsg1 or Dsg3 fragment further purified using gel filtration chromatography to remove the thrombin enzyme and the released poly-His tag.

In some embodiments, autoantibodies can accumulate in the dermal (the targeting cell junctions in the dermal compartment) and/or subcutaneous compartments, for example, in a patient with PV. In such situations, if EDC is delivered subcutaneously, the EDC may be neutralized right at the injection site and not make it to the lymph nodes. Therefore, owing the potential neutralization of one or more EDC herein by the autoantibodies in the dermal and/or subcutaneous compartments, the PV patient is initially treated with one or more immunosuppressive agents (e.g. Rituxan) in order to lower and/or eliminate the autoantibodies. Although the immunosuppressive agents do not specifically target the autoantibodies in the dermal and/or subcutaneous compartments, the immunosuppressive agents suppress the immune system, and therefore, suppress the production of autoantibodies. This results in inhibition of production of new antibodies and elimination of the circulating autoantibodies (the circulating autoantibodies are recycled and/or degraded based on their half-lives). The PV patient can then be administered one or more EDCs herein via the intravenous, subcutaneous and/or intradermal routes to target the autoimmune memory B cells in the lymph nodes to prevent disease relapse. Thus, in some embodiments, the one or more EDCs provided herein can be used in conjunction with one or more immunosuppressive therapies to prevent disease relapse. For example, PV has a high frequency of relapse and repeated Rituxan treatment causes fatal infections. Thus, administration of one or more EDCs herein following administration of Rituxan can prevent fatal infections in PV patients. Additionally, Rituxan cannot reach the autoimmune memory B cells in the lymph nodes. In contrast, the EDCs can reach the autoimmune memory B cells in the lymph nodes. Therefore, in addition to preventing relapse, the EDCs can cure the patient of PV by eliminating the autoimmune memory B cells in the lymph nodes.

EXAMPLES

The following examples are non-limiting and presented merely to illustrate the present invention and to assist one of ordinary skill in the art in making and using the invention. The examples are not intended in any way to otherwise limit the scope of the invention.

Example 1

Blood from a patient with MN is collected. Total B cells are isolated from the blood. FACS is used to identify and separate cells that express the receptor for PLA2R epitope. EDC is added to the cells that carry the receptor for PLA2R epitope. Cells that do not express the receptor for PLA2R epitope are used as control. The EDC is added to each cell population at a dose $\frac{1}{1000}^{th}$ the ordinary dose of the drug in the EDC. The cells populations are incubated overnight with the EDC. Cells that express PLA2R epitope receptor are killed by the EDC whereas cells that do not express the receptor are unaffected and survive. Cells can be stained with trypan blue to assess the effectiveness of the EDC in killing cells that express the receptor for PLA2R epitope.

Example 2

Blood from a patient with MN is collected. Cells that express the receptor for PLA2R epitope are labeled with a fluorescently-tagged PLA2R epitope. Labeled and unlabeled cells are separated using microscopy. Unlabeled cells are used as control. The EDC is added to each cell population at a dose $\frac{1}{1000}^{th}$ the ordinary dose of the drug in the EDC. The cells populations are incubated overnight with the EDC. Cells that express PLA2R epitope receptor are killed by the EDC whereas cells that do not express the receptor are unaffected and survive. Cells can be stained with trypan blue to assess the effectiveness of the EDC in killing cells that express the receptor for PLA2R epitope.

Example 3

In one example, following treatment with one or more treatment options provided herein, a patient with MN recovered in about 1 month as compared to about 6 months with previous treatment regimens. Patient recovery was measured by protein levels in urine.

Example 4—Engineering of a Modified PLA2R-Epitope for Site-Specific Chemical Conjugation PLA2R-epitope contains at minimum 3 domains, namely, the N-terminal cysteine rich domain (CysR), the fibronectin-like type II domain (FnII), and the C-type lectin-like domain 1 (CTLD1) (FIG. 1, FIG. 2, and FIG. 23). The nature of interaction(s) of the epitope with autoantibodies and/or B cell receptor (BCR) has remained unclear. It is critical that conjugation of a chemical to the epitope does not interfere with the antibody-antigen interaction.

To achieve this, a specific site in PLA2R-epitope for conjugation was developed. Specifically, a free cysteine was engineered into the C-terminal tail of the epitope to develop a specific site for chemical conjugation. A TEV cleavage site and a His-tag (6 Histidine residues) were also engineered into the epitope protein C-terminal to the introduced cysteine for protein purification. FIG. 23 (top) shows a schematic of the design of a modified PLA2R-epitope construct for protein purification and drug conjugation. FIG. 23 (middle) shows a schematic of how a drug (cytotoxic agent) is conjugated to the purified PLA2R epitope.

Assessment of protein expression showed that modified PLA2R-epitope was well-expressed and strongly reacted to the anti-PLA2R autoantibodies, indicating the introduced cysteine had no effect on the epitope folding. The construct was then expressed in the HEK293 cells and the epitope protein was purified using nickel and gel filtration columns followed with TEV cleavage to remove the His-tag. The protein was then coupled with a fluorescent agent (eg. FITC) or a cytotoxic reagent (eg. Monomethyl auristatin E (MMAE)).

FIG. 23 (top) shows the design of a modified PLA2R-epitope construct for protein purification and drug conjugation. A site-specific conjugation site was introduced into PLA2R epitope followed with a TEV cleavage site and a His-tag in the design of PLA2R EDC. FIG. 23 (middle) shows how a drug is conjugated to the purified PLA2R-epitope. The purified epitope protein was conjugated with a cytotoxic agent in a site-specific manner. FIG. 23 (bottom) shows the purity of PLA2R-epitope protein after purification. The conjugated PLA2R epitope proteins were purified and resolved on SDS-PAGE. The epitope was analyzed on a 7% SDS-PAGE which showed a single protein band at the correct molecular weight (about 37 kDa) (FIG. 23; bottom left).

In a separate experiment (FIG. 23; bottom right), equal amount of epitope, FITC conjugated epitope and MMAE conjugated epitope proteins were resolved on a SDS-PAGE under the non-reducing condition, transferred to a membrane, and probed by a patient serum containing anti-PLA2R autoantibodies. The unconjugated and the conjugated PLA2R-epitope proteins were resolved on a 4-20% SDS-PAGE under the non-reducing condition and probed with a patient serum containing anti-PLA2R autoantibodies (FIG. 23, bottom right). Results showed that the drug conjugated PLA2R-epitope bound strongly to the autoantibodies as strongly as the unconjugated PLA2R-epitope (FIG. 23; bottom right).

Western blotting with anti-PLA2R autoantibodies showed that the PLA2R epitope strongly reacted with anti-PLA2R autoantibodies indicating that the introduced cysteine had not affected the epitope's folding (FIG. 23 (bottom right; Western blot)). The construct was then expressed in the HEK293 cells and the epitope protein was purified using nickel and gel filtration columns followed with TEV cleavage to remove the His-tag. The protein was then coupled with a fluorescent agent (eg. FITC) or a cytotoxic reagent (eg. Monomethyl auristatin E (MMAE)) (FIG. 23).

Example 5—Assessment of PLA2R-Epitope-FITC Binding to the Memory B Cells Isolated from PMN Patients PMN is a B cell-mediated autoimmune disease. The pathogenic autoantibodies are secreted by the plasma cells derived from a group of memory B cells that possess unique B cell receptors (BCR) specifically bind to the PLA2R-epitope. To distinguish this group of memory B cells and to assess if the PLA2R epitope drug conjugate could effectively bind to the BCRs on the surface of this group of memory B cells, a binding assay was performed using PLA2R-epitope-FITC analysis on the total B cells isolated from PMN patients' blood samples. Total B cells isolated from patient peripheral blood were cultured overnight in the RPMI media supplemented with fetal bovine serum and antibiotics at 37° C., 5% $CO_2$. Cells were then dispersed by pipetting up and down, collected and washed twice with ice-cold PBS. Cells were subsequently incubated with PLA2R-epitope-FITC in PBS for 1 h at 4° C. Cells were washed 3 times with ice-cold PBS and imaged under a fluorescent microscope at the excitation wave length 488 nm and emission wavelength 520 nm. FIG. 24 shows a population of B cells that were labeled with PLA2R-epitope-FITC, indicating the presence of a specific population of PLA2R epitope-binding memory B cells in PMN patients, and the strong binding of PLA2R-epitope-FITC to the BCRs on the surface of these memory B cells.

Example 6—Assessment of the Efficacy of PLA2R-Epitope-MMAE on the Memory B Cells Isolated from PMN Patients The efficacy of the PLA2R-epitope-MMAE on eliminating the PLA2R-epitope specific memory B cells isolated from PMN patients was assessed. MMAE is a potent cytotoxic agent that blocks tubulin polymerization causing cell death. MMAE has been used to develop an antibody-drug conjugate, Brentuximab vedotin (trade name Adcetris) for lymphoma treatment, and was approved by FDA in 2011. Total B cells isolated from patient peripheral blood were cultured overnight in RPMI medium and then split equally into two wells on a 12 well cell culture plate (2 ml/per well). One well of cells was incubated with MMAE, and the other was incubated with PLA2R-epitope-MMAE for 24 h in a cell culture incubator. Cells from both of the wells were then collected, washed with ice cold PBS, and incubated with PLA2R-epitope-FITC for 1 h at 4° C. Cells were washed 3 times with ice-cold PBS and imaged under a fluorescent microscope at the excitation wave length 488 nm and emission wavelength 520 nm.

Preincubation with MMAE alone resulted in a number of B cells being stained by the PLA2R-epitope-FITC (FIG. 25).

In contrast, preincubation with PLA2R-epitope-MMAE showed no staining with PLA2R-epitope-FITC indicating the specific targeting and eliminating of the PLA2R-epitope specific memory B cells by PLA2R-epitope-MMAE (FIG. 25). Light microscope images of PLA2R-epitope-MMAE treated B cells also indicated that EDC produced little effect on most of the B cells (FIG. 25).

Example 7—Development of an EDC Treatment for Pemphigus Vulgaris

In order to preserve the calcium binding sites in Dsg3 epitope, which are critical for autoantibody binding, Dsg3 EC1-4 domains (450 amino acids; FIG. 32; SEQ ID NO: 17) were selected as the epitope for drug conjugation. In order to develop a specific conjugation site in Dsg3 EC1-4, all the endogenous cysteines (underlined in FIG. 32) were replaced with a structural similar amino acid, serine. In addition, 2 endogenous N-glycosylation sites (Asn61 and Asn131; underlined in FIG. 32) were replaced with a structural similar amino acid, glutamine. The same approach was adopted for designing the Dsg1 epitope for drug conjugation, with the modified Dsg1 EC1-3 domains (336 amino acids) were selected (FIG. 31; SEQ ID NO: 16). The epitopes generated were named Dsg1 EC1-3 and Dsg3 EC1-4. The molecular weight of the Dsg1 EC1-3 epitope was about 35 kDa and the molecular weight of the Dsg3 EC1-4 epitope was about 60 kDa.

A free cysteine was then engineered into the C-terminal tail of each of the epitopes to develop a specific site for chemical conjugation. A TEV cleavage site and a His-tag (6 His) were also engineered into the epitope protein after the introduced cysteine for protein purification (FIG. 27).

The engineered epitopes were expressed in the HEK 293 cells and purified from the culture media using nickel affinity and gel filtration columns followed with TEV cleavage to remove the His-tag (FIG. 28, left panel; Coomassie Blue). The epitopes were then coupled with either a fluorescent agent (e.g., FITC) or a cytotoxic reagent (e.g., MMAE)

Because autoantibodies to Dsg1 and Dsg3 preferentially bind the non-denatured Dsg 1 or Dsg3 proteins, the purified FITC or MMAE conjugated forms of the two epitopes prior to TEV treatment were mixed with a mucocutaneous PV patient serum in PBS buffer to form immune complexes and then immunoprecipitated with the protein G beads. Equal amounts of the purified conjugated forms of Dsg1 and Dsg3 epitopes (prior to TEV cleavage) were mixed with a mucocutaneous PV patient serum in PBS buffer for 2 h at 4° C. and immunoprecipitated with protein G beads. The beads were extensively washed and the bound epitopes were eluted with SDS-sample buffer, resolved on a SDS-PAGE, transferred to a membrane, and probed by an anti-His tag antibody (FIG. 28, middle and right panels; Western blot). Western blot results showed that the engineered and the chemical conjugated epitopes of Dsg1 and Dsg3 reacted strongly with the autoantibodies and were immunoprecipitated well by the protein G beads, indicating that engineering and chemical conjugation of the epitope proteins had no interference with the autoantibody-antigen interactions.

Example 8—Assessment of Dsg-Epitope-FITC Binding to the Memory B Cells Isolated from Mucocutaneous PV Patients The ability of Dsg-epitope-FITC binding to the specific BCRs in the memory B cells isolated from mucocutaneous PV patients' blood samples was assessed. Peripheral blood mononuclear cells were first isolated from the whole blood using density centrifugation (Histopaque-1077), followed with total B cell isolation using a B cell negative isolation kit. The isolated total B cells were then cultured overnight in the RPMI media supplemented with fetal bovine serum and antibiotics at 37° C., 5% $CO_2$. Cells were then processed, stained with Dsg-epitope-FITC in PBS for 1 h at 4° C. and imaged under a fluorescent microscope at the excitation wave length 488 nm and emission wavelength 520 nm. FIG. 29 shows, Dsg-epitope-FITC strongly stained a group of B cells, indicating the strong binding of Dsg-epitope-FITC to the BCRs on the surface of these memory B cells.

Example 9—Assessment of the Efficacy of Dsg-Epitope-MMAE on the Memory B Cells Isolated from Mucocutaneous PV Patients The efficacy of the Dsg1 and Dsg3 epitope conjugated to MMAE to eliminate Dsg1 and Dsg3-epitope specific memory B cells, respectively, isolated from the mucocutaneous PV patients was assessed. Total B cells isolated from patient peripheral blood were cultured overnight in RPMI medium and then split equally into two wells on a 12 well cell culture plate (2 ml/per well). One well of cells was incubated with MMAE, and the other was incubated with Dsg1 and Dsg3-epitope-MMAE for 24 h in a cell culture incubator. Cells from both of the wells were then collected, washed with ice cold PBS, and incubated with Dsg1 and Dsg3-epitope-FITC for 1 h at 4° C. Cells were washed 3 times with ice-cold PBS and imaged under a fluorescent microscope at the excitation wave length 488 nm and emission wavelength 520 nm.

Preincubation with MMAE alone resulted in a number of B cells being stained by Dsg1 and Dsg3-epitope-FITC (FIG. 30). In contrast, preincubation with Dsg1 and Dsg3-epitope-MMAE showed no staining with Dsg1 and Dsg3-epitope-FITC indicating the specific targeting and eliminating of the Dsg1 and Dsg3-epitope specific memory B cells by Dsg1 and Dsg3-epitope-MMAE (FIG. 30). Light microscope images of Dsg 1 and Dsg3-epitope-MMAE treated B cells also indicated that EDC produced little effect on most of the B cells (FIG. 30).

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein.

In this application, the use of the singular includes the plural unless specifically stated otherwise. Also, the use of "comprise", "comprises", "comprising", "contain", "contains", "containing", "include", "includes", and "including" are not intended to be limiting.

As used in this specification and claims, the singular forms "a," "an" and "the" include plural references unless the content clearly dictates otherwise.

As used herein, "about" means a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

Although this invention has been disclosed in the context of certain embodiments and examples, those skilled in the art will understand that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes or embodiments of the disclosed invention. Thus, it is intended that the scope of the present invention herein disclosed should not be limited by the particular disclosed embodiments described above.

It should be understood, however, that this detailed description, while indicating preferred embodiments of the invention, is given by way of illustration only, since various changes and modifications within the spirit and scope of the invention will become apparent to those skilled in the art.

The terminology used in the description presented herein is not intended to be interpreted in any limited or restrictive manner. Rather, the terminology is simply being utilized in conjunction with a detailed description of embodiments of the systems, methods and related components. Furthermore, embodiments may comprise several novel features, no single one of which is solely responsible for its desirable attributes or is believed to be essential to practicing the inventions herein described.

Those skilled in the art will appreciate that the conceptions and specific embodiments disclosed in the foregoing description may be readily utilized as a basis for modifying or designing other embodiments for carrying out the same purposes of the present invention.

All scientific and technical terms used in this application have meanings commonly used in the art unless otherwise specified. As used in this application, the following words or phrases have the meanings specified.

As used herein, a "detectable marker" or "label" is a molecule attached to, or synthesized as part of a reagent. This molecule should be uniquely detectable and will allow the reagent to be detected as a result. These detectable moieties are often radioisotopes, chemiluminescent molecules, enzymes, haptens, or even unique oligonucleotide sequences.

As used herein, "polypeptide" includes proteins, fragments of proteins, and peptides, whether isolated from natural sources, produced by recombinant techniques or chemically synthesized. Polypeptides typically comprise at least about 6 amino acids. Shorter polypeptides, e.g., those less than about 50 amino acids in length, are typically referred to as "peptides".

A polypeptide of the invention can, in some embodiments, comprise a variant of a native protein. A polypeptide "variant," as used herein, is a polypeptide that differs from a native protein in one or more substitutions, deletions, additions and/or insertions, such that the therapeutic efficacy of the polypeptide is not substantially diminished. In other words, the efficacy may be enhanced or unchanged, relative to the native protein, or may be diminished by less than 50%, and preferably less than 20%, relative to the native protein. Preferred variants include those in which one or more portions, such as an N-terminal leader sequence, have been removed. Other preferred variants include variants in which a small portion (e.g., 1-30 amino acids, preferably 5-15 amino acids) has been removed from the N- and/or C-terminal of the mature protein. Polypeptide variants preferably exhibit at least about 70%, more preferably at least about 90% and most preferably at least about 95% identity (determined as described above) to the identified polypeptides. As is known in the art, variants can also be selected to optimize affinity of the polypeptide for a binding partner.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; And (5) Phe, Tyr, Trp, His. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

The terminology used in the description presented herein is not intended to be interpreted in any limited or restrictive manner. Rather, the terminology is simply being utilized in conjunction with a detailed description of embodiments of the systems, methods and related components. Furthermore, embodiments may comprise several novel features, no single one of which is solely responsible for its desirable attributes or is believed to be essential to practicing the inventions herein described.

It should be understood, however, that this detailed description, while indicating preferred embodiments of the invention, is given by way of illustration only, since various changes and modifications within the spirit and scope of the invention will become apparent to those ordinary skill in the art.

REFERENCES

All references cited in this disclosure are incorporated herein by reference in their entireties.

U.S. Pat. No. 8,507,215 B2

Beck, L. H., et al., N Engl J Med, Vol. 361, pp. 11-21, 2009.

Beck, L. H., et al., J Am Soc Nephrol, Vol. 22, pp. 1543-1550, 2011.

Kao, L., et al., J Am Soc Nephrol, Vol. 26, No. 2, pp. 291-301, 2015.

Ohyama, B., et al., J Invest Dermatol, Vol. 132, pp. 1158-1168, 2012.

Alewine, C., et al, The Oncologist, Vol. 20, pp. 176-185, 2015.

Pape, K. A., et al, Immunity, Vol. 26, pp. 491-502, 2007.

Roozendaal, R., et al, Immunity, Vol. 30, pp. 264-276, 2009.

What is claimed is:

1. A method of identifying and treating membranous nephropathy (MN) in a patient, comprising:
   obtaining a sample from the patient, said sample suspected of containing an anti-PLA2R autoantibody producing B cell population;
   contacting said sample with a first PLA2R epitope bound to a label, wherein the first PLA2R epitope comprises SEQ ID NO:13;
   determining the amount of binding of the labeled first PLA2R epitope to cells of the anti-PLA2R autoantibody producing B cell population within the sample;
   comparing the amount of binding of the labeled first PLA2R epitope in the sample to the amount of binding expected in a control sample from a subject not having MN;
   identifying an increase in the amount of binding of the labeled first PLA2R epitope in the sample relative to the amount of binding expected in the control sample thereby identifying the patient as needing treatment for MN; and
   administering to the patient a complex comprising a second PLA2R epitope linked to a drug that reduces or eliminates anti-PLA2R autoantibody producing B cell population in the patient, wherein the second PLA2R epitope comprises SEQ ID NO:13, thereby reducing or eliminating the anti-PLA2R autoantibody producing B cell population in the patient, wherein the complex that reduces or eliminates anti-PLA2R autoantibody producing B cell population in the patient has a molecular weight of 14-80 kDa.

2. The method of claim 1, wherein the sequence of the first or second PLA2R epitope comprises a sequence selected from the group consisting of a sequence as provided in SEQ ID NO: 1, SEQ ID NO: 2, SEQ ID NO: 2 plus at least about 5% of the sequence provided in SEQ ID NO: 3, SEQ ID NO: 4, SEQ ID NO: 5, and SEQ ID NO: 5 plus at least about 5% of the sequence provided in SEQ ID NO: 6.

3. The method of claim 1, wherein the increase in binding in the sample relative to binding in the control sample is at least 10%.

4. The method of claim 1, wherein the sample is a bodily fluid containing cells.

5. The method of claim 4, wherein the bodily fluid is selected from the group consisting of blood, plasma, serum, urine, cerebrospinal fluid, and lymph.

6. The method of claim 1, wherein the method is performed at multiple time points, wherein a decrease in the amount of binding in subsequent time points indicates an amelioration of MN, and wherein an increase in the amount of binding indicates a likelihood of disease progression or relapse.

7. The method of claim 6, wherein a first time point is before treatment of MN in the patient has begun and a subsequent time point is after initiation of the treatment.

8. The method of claim 1, wherein the first labeled PLA2R epitope detects B cells or T cells in the sample, and wherein the binding is detected by detecting binding to the B cells or T cells.

9. The method of claim 1, wherein the label is a fluorophore.

10. The method of claim 9, wherein the binding is detected using fluorescence activated cell sorting (FACS) or fluorescence microscopy.

11. The method of claim 1, wherein the label is a radiolabel or a magnetic label.

12. The method of claim 11, wherein the binding is detected by enzyme-linked assay.

13. The method of claim 12, wherein the enzyme-linked assay is Enzyme-Linked ImmunoSpot (ELISPOT).

14. The method of claim 11, wherein the binding is detected by radioimmunoassay or magnetic immunoassay.

15. The method of claim 1, wherein the drug is selected from the group consisting of one or more Duocarmycin analogues, or cytotoxic drug.

16. The method of claim 1, wherein an efficacy of reducing or eliminating the anti-PLA2R autoantibody producing B cell population ranges from about 70% to about 100%.

17. The method of claim 1, wherein the complex also eliminates a T cell population, wherein the T cell population provides T cell help to the anti-PLA2R autoantibody producing B cell population, and wherein an efficacy of reducing or eliminating the T cell population ranges from about 70% to about 100%.

18. The method of claim 1, wherein the drug is linked to the PLA2R fragment via a valine-citrulline linker.

19. The method of claim 1, wherein the drug is a cytotoxic drug selected from the group consisting of auristatin, ado-zelesin, bizelesin, carzelesin, methotrexate, 5-fluorouracil, Doxorubicin, cyclophosphamide, duocarmycin, Epirubicin, cisplatin, 5-fluorouracil and capecitabine.

20. The method of claim 1, wherein the sample is a biopsy sample of a tissue or organ.

21. The method of claim 1, wherein the drug is monomethyl auristatin E (MMAE).

22. The method of claim 11, wherein the complex that reduces or eliminates anti-PLA2R autoantibody producing B cell population in the patient comprises an additional modification.

23. The method of claim 22, wherein the additional modification is selected from the group consisting of insertion of a 2 to 10 amino acid N-terminal peptide, insertion of a 2 to 10 amino acid C-terminal peptide, attaching a reagent, and adding one or more heterologous sequences.

* * * * *

SEQUENCE LISTING

<160> NUMBER OF SEQ ID NOS: 17

<210> SEQ ID NO 1
<211> LENGTH: 658
<212> TYPE: PRT
<213> ORGANISM: Artificial
<220> FEATURE:
<223> OTHER INFORMATION: Synthetic

<400> SEQUENCE: 1

```
Met Leu Leu Ser Pro Ser Leu Leu Leu Leu Leu Gly Ala Pro
1               5                   10                  15

Arg Gly Cys Ala Glu Gly Val Ala Ala Ala Leu Thr Pro Glu Arg Leu
                20                  25                  30

Leu Glu Trp Gln Asp Lys Gly Ile Phe Val Ile Gln Ser Glu Ser Leu
            35                  40                  45

Lys Lys Cys Ile Gln Ala Gly Lys Ser Val Leu Thr Leu Glu Asn Cys
        50                  55                  60

Lys Gln Ala Asn Lys His Met Leu Trp Lys Trp Val Ser Asn His Gly
65                  70                  75                  80

Leu Phe Asn Ile Gly Gly Ser Gly Cys Leu Gly Leu Asn Phe Ser Ala
                85                  90                  95

Pro Glu Gln Pro Leu Ser Leu Tyr Glu Cys Asp Ser Thr Leu Val Ser
                100                 105                 110

Leu Arg Trp Arg Cys Asn Arg Lys Met Ile Thr Gly Pro Leu Gln Tyr
            115                 120                 125

Ser Val Gln Val Ala His Asp Asn Thr Val Val Ala Ser Arg Lys Tyr
        130                 135                 140

Ile His Lys Trp Ile Ser Tyr Gly Ser Gly Gly Gly Asp Ile Cys Glu
145                 150                 155                 160

Tyr Leu His Lys Asp Leu His Thr Ile Lys Gly Asn Thr His Gly Met
                165                 170                 175

Pro Cys Met Phe Pro Phe Gln Tyr Asn His Gln Trp His His Glu Cys
                180                 185                 190

Thr Arg Glu Gly Arg Glu Asp Asp Leu Leu Trp Cys Ala Thr Thr Ser
            195                 200                 205

Arg Tyr Glu Arg Asp Glu Lys Trp Gly Phe Cys Pro Asp Pro Thr Ser
        210                 215                 220

Ala Glu Val Gly Cys Asp Thr Ile Trp Glu Lys Asp Leu Asn Ser His
225                 230                 235                 240

Ile Cys Tyr Gln Phe Asn Leu Leu Ser Ser Leu Ser Trp Ser Glu Ala
                245                 250                 255

His Ser Ser Cys Gln Met Gln Gly Gly Thr Leu Leu Ser Ile Thr Asp
                260                 265                 270

Glu Thr Glu Glu Asn Phe Ile Arg Glu His Met Ser Ser Lys Thr Val
            275                 280                 285

Glu Val Trp Met Gly Leu Asn Gln Leu Asp Glu His Ala Gly Trp Gln
        290                 295                 300

Trp Ser Asp Gly Thr Pro Leu Asn Tyr Leu Asn Trp Ser Pro Glu Val
305                 310                 315                 320

Asn Phe Glu Pro Phe Val Glu Asp His Cys Gly Thr Phe Ser Ser Phe
                325                 330                 335

Met Pro Ser Ala Trp Arg Ser Arg Asp Cys Glu Ser Thr Leu Pro Tyr
                340                 345                 350

Ile Cys Lys Lys Tyr Leu Asn His Ile Asp His Glu Ile Val Glu Lys
```

```
                355                 360                 365
Asp Ala Trp Lys Tyr Tyr Ala Thr His Cys Glu Pro Gly Trp Asn Pro
    370                 375                 380

Tyr Asn Arg Asn Cys Tyr Lys Leu Gln Lys Glu Glu Lys Thr Trp His
385                 390                 395                 400

Glu Ala Leu Arg Ser Cys Gln Ala Asp Asn Ser Ala Leu Ile Asp Ile
                405                 410                 415

Thr Ser Leu Ala Glu Val Glu Phe Leu Val Thr Leu Leu Gly Asp Glu
            420                 425                 430

Asn Ala Ser Glu Thr Trp Ile Gly Leu Ser Ser Asn Lys Ile Pro Val
        435                 440                 445

Ser Phe Glu Trp Ser Asn Asp Ser Ser Val Ile Phe Thr Asn Trp His
    450                 455                 460

Thr Leu Glu Pro His Ile Phe Pro Asn Arg Ser Gln Leu Cys Val Ser
465                 470                 475                 480

Ala Glu Gln Ser Glu Gly His Trp Lys Val Lys Asn Cys Glu Glu Arg
                485                 490                 495

Leu Phe Tyr Ile Cys Lys Lys Ala Gly His Val Leu Ser Asp Ala Glu
            500                 505                 510

Ser Gly Cys Gln Glu Gly Trp Glu Arg His Gly Gly Phe Cys Tyr Lys
        515                 520                 525

Ile Asp Thr Val Leu Arg Ser Phe Asp Gln Ala Ser Ser Gly Tyr Tyr
    530                 535                 540

Cys Pro Pro Ala Leu Val Thr Ile Thr Asn Arg Phe Glu Gln Ala Phe
545                 550                 555                 560

Ile Thr Ser Leu Ile Ser Ser Val Val Lys Met Lys Asp Ser Tyr Phe
                565                 570                 575

Trp Ile Ala Leu Gln Asp Gln Asn Asp Thr Gly Glu Tyr Thr Trp Lys
            580                 585                 590

Pro Val Gly Gln Lys Pro Glu Pro Val Gln Tyr Thr His Trp Asn Thr
        595                 600                 605

His Gln Pro Arg Tyr Ser Gly Gly Cys Val Ala Met Arg Gly Arg His
    610                 615                 620

Pro Leu Gly Arg Trp Glu Val Lys His Cys Arg His Phe Lys Ala Met
625                 630                 635                 640

Ser Leu Cys Lys Gln Pro Val Glu Asn Gln Glu Lys Ala Glu Tyr Glu
                645                 650                 655

Glu Arg

<210> SEQ ID NO 2
<211> LENGTH: 364
<212> TYPE: PRT
<213> ORGANISM: Artificial
<220> FEATURE:
<223> OTHER INFORMATION: Synthetic

<400> SEQUENCE: 2

Met Leu Leu Ser Pro Ser Leu Leu Leu Leu Leu Leu Leu Gly Ala Pro
1               5                   10                  15

Arg Gly Cys Ala Glu Gly Val Ala Ala Ala Leu Thr Pro Glu Arg Leu
            20                  25                  30

Leu Glu Trp Gln Asp Lys Gly Ile Phe Val Ile Gln Ser Glu Ser Leu
        35                  40                  45

Lys Lys Cys Ile Gln Ala Gly Lys Ser Val Leu Thr Leu Glu Asn Cys
    50                  55                  60
```

```
Lys Gln Ala Asn Lys His Met Leu Trp Lys Trp Val Ser Asn His Gly
 65                  70                  75                  80

Leu Phe Asn Ile Gly Gly Ser Gly Cys Leu Gly Leu Asn Phe Ser Ala
             85                  90                  95

Pro Glu Gln Pro Leu Ser Leu Tyr Glu Cys Asp Ser Thr Leu Val Ser
            100                 105                 110

Leu Arg Trp Arg Cys Asn Arg Lys Met Ile Thr Gly Pro Leu Gln Tyr
        115                 120                 125

Ser Val Gln Val Ala His Asp Asn Thr Val Val Ala Ser Arg Lys Tyr
    130                 135                 140

Ile His Lys Trp Ile Ser Tyr Gly Ser Gly Gly Asp Ile Cys Glu
145                 150                 155                 160

Tyr Leu His Lys Asp Leu His Thr Ile Lys Gly Asn Thr His Gly Met
                165                 170                 175

Pro Cys Met Phe Pro Phe Gln Tyr Asn His Gln Trp His His Glu Cys
            180                 185                 190

Thr Arg Glu Gly Arg Glu Asp Asp Leu Leu Trp Cys Ala Thr Thr Ser
        195                 200                 205

Arg Tyr Glu Arg Asp Glu Lys Trp Gly Phe Cys Pro Asp Pro Thr Ser
210                 215                 220

Ala Glu Val Gly Cys Asp Thr Ile Trp Glu Lys Asp Leu Asn Ser His
225                 230                 235                 240

Ile Cys Tyr Gln Phe Asn Leu Leu Ser Ser Leu Ser Trp Ser Glu Ala
                245                 250                 255

His Ser Ser Cys Gln Met Gln Gly Gly Thr Leu Leu Ser Ile Thr Asp
            260                 265                 270

Glu Thr Glu Glu Asn Phe Ile Arg Glu His Met Ser Ser Lys Thr Val
        275                 280                 285

Glu Val Trp Met Gly Leu Asn Gln Leu Asp Glu His Ala Gly Trp Gln
290                 295                 300

Trp Ser Asp Gly Thr Pro Leu Asn Tyr Leu Asn Trp Ser Pro Glu Val
305                 310                 315                 320

Asn Phe Glu Pro Phe Val Glu Asp His Cys Gly Thr Phe Ser Ser Phe
                325                 330                 335

Met Pro Ser Ala Trp Arg Ser Arg Asp Cys Glu Ser Thr Leu Pro Tyr
            340                 345                 350

Ile Cys Lys Lys Tyr Leu Asn His Ile Asp His Glu
        355                 360

<210> SEQ ID NO 3
<211> LENGTH: 294
<212> TYPE: PRT
<213> ORGANISM: Artificial
<220> FEATURE:
<223> OTHER INFORMATION: Synthetic

<400> SEQUENCE: 3

Ile Val Glu Lys Asp Ala Trp Lys Tyr Tyr Ala Thr His Cys Glu Pro
 1               5                  10                  15

Gly Trp Asn Pro Tyr Asn Arg Asn Cys Tyr Lys Leu Gln Lys Glu Glu
             20                  25                  30

Lys Thr Trp His Glu Ala Leu Arg Ser Cys Gln Ala Asp Asn Ser Ala
         35                  40                  45

Leu Ile Asp Ile Thr Ser Leu Ala Glu Val Glu Phe Leu Val Thr Leu
     50                  55                  60
```

Leu Gly Asp Glu Asn Ala Ser Glu Thr Trp Ile Gly Leu Ser Ser Asn
65                  70                  75                  80

Lys Ile Pro Val Ser Phe Glu Trp Ser Asn Asp Ser Val Ile Phe
            85                  90                  95

Thr Asn Trp His Thr Leu Glu Pro His Ile Phe Pro Asn Arg Ser Gln
                100                 105                 110

Leu Cys Val Ser Ala Glu Gln Ser Glu Gly His Trp Lys Val Lys Asn
            115                 120                 125

Cys Glu Glu Arg Leu Phe Tyr Ile Cys Lys Lys Ala Gly His Val Leu
130                 135                 140

Ser Asp Ala Glu Ser Gly Cys Gln Glu Gly Trp Glu Arg His Gly Gly
145                 150                 155                 160

Phe Cys Tyr Lys Ile Asp Thr Val Leu Arg Ser Phe Asp Gln Ala Ser
                165                 170                 175

Ser Gly Tyr Tyr Cys Pro Pro Ala Leu Val Thr Ile Thr Asn Arg Phe
            180                 185                 190

Glu Gln Ala Phe Ile Thr Ser Leu Ile Ser Ser Val Val Lys Met Lys
                195                 200                 205

Asp Ser Tyr Phe Trp Ile Ala Leu Gln Asp Gln Asn Asp Thr Gly Glu
210                 215                 220

Tyr Thr Trp Lys Pro Val Gly Gln Lys Pro Glu Pro Val Gln Tyr Thr
225                 230                 235                 240

His Trp Asn Thr His Gln Pro Arg Tyr Ser Gly Gly Cys Val Ala Met
                245                 250                 255

Arg Gly Arg His Pro Leu Gly Arg Trp Glu Val Lys His Cys Arg His
            260                 265                 270

Phe Lys Ala Met Ser Leu Cys Lys Gln Pro Val Glu Asn Gln Glu Lys
            275                 280                 285

Ala Glu Tyr Glu Glu Arg
    290

<210> SEQ ID NO 4
<211> LENGTH: 805
<212> TYPE: PRT
<213> ORGANISM: Artificial
<220> FEATURE:
<223> OTHER INFORMATION: Synthetic

<400> SEQUENCE: 4

Met Leu Leu Ser Pro Ser Leu Leu Leu Leu Leu Leu Leu Gly Ala Pro
1               5                   10                  15

Arg Gly Cys Ala Glu Gly Val Ala Ala Ala Leu Thr Pro Glu Arg Leu
            20                  25                  30

Leu Glu Trp Gln Asp Lys Gly Ile Phe Val Ile Gln Ser Glu Ser Leu
        35                  40                  45

Lys Lys Cys Ile Gln Ala Gly Lys Ser Val Leu Thr Leu Glu Asn Cys
50                  55                  60

Lys Gln Ala Asn Lys His Met Leu Trp Lys Trp Val Ser Asn His Gly
65                  70                  75                  80

Leu Phe Asn Ile Gly Gly Ser Gly Cys Leu Gly Leu Asn Phe Ser Ala
                85                  90                  95

Pro Glu Gln Pro Leu Ser Leu Tyr Glu Cys Asp Ser Thr Leu Val Ser
            100                 105                 110

Leu Arg Trp Arg Cys Asn Arg Lys Met Ile Thr Gly Pro Leu Gln Tyr
        115                 120                 125

```
Ser Val Gln Val Ala His Asp Asn Thr Val Val Ala Ser Arg Lys Tyr
130                 135                 140

Ile His Lys Trp Ile Ser Tyr Gly Ser Gly Gly Asp Ile Cys Glu
145                 150                 155                 160

Tyr Leu His Lys Asp Leu His Thr Ile Lys Gly Asn Thr His Gly Met
                165                 170                 175

Pro Cys Met Phe Pro Phe Gln Tyr Asn His Gln Trp His His Glu Cys
                180                 185                 190

Thr Arg Glu Gly Arg Glu Asp Leu Leu Trp Cys Ala Thr Thr Ser
                195                 200                 205

Arg Tyr Glu Arg Asp Glu Lys Trp Gly Phe Cys Pro Asp Pro Thr Ser
210                 215                 220

Ala Glu Val Gly Cys Asp Thr Ile Trp Glu Lys Asp Leu Asn Ser His
225                 230                 235                 240

Ile Cys Tyr Gln Phe Asn Leu Leu Ser Ser Leu Ser Trp Ser Glu Ala
                245                 250                 255

His Ser Ser Cys Gln Met Gln Gly Gly Thr Leu Leu Ser Ile Thr Asp
                260                 265                 270

Glu Thr Glu Glu Asn Phe Ile Arg Glu His Met Ser Ser Lys Thr Val
                275                 280                 285

Glu Val Trp Met Gly Leu Asn Gln Leu Asp Glu His Ala Gly Trp Gln
290                 295                 300

Trp Ser Asp Gly Thr Pro Leu Asn Tyr Leu Asn Trp Ser Pro Glu Val
305                 310                 315                 320

Asn Phe Glu Pro Phe Val Glu Asp His Cys Gly Thr Phe Ser Ser Phe
                325                 330                 335

Met Pro Ser Ala Trp Arg Ser Arg Asp Cys Glu Ser Thr Leu Pro Tyr
                340                 345                 350

Ile Cys Lys Lys Tyr Leu Asn His Ile Asp His Glu Ile Val Glu Lys
                355                 360                 365

Asp Ala Trp Lys Tyr Tyr Ala Thr His Cys Glu Pro Gly Trp Asn Pro
370                 375                 380

Tyr Asn Arg Asn Cys Tyr Lys Leu Gln Lys Glu Glu Lys Thr Trp His
385                 390                 395                 400

Glu Ala Leu Arg Ser Cys Gln Ala Asp Asn Ser Ala Leu Ile Asp Ile
                405                 410                 415

Thr Ser Leu Ala Glu Val Glu Phe Leu Val Thr Leu Leu Gly Asp Glu
                420                 425                 430

Asn Ala Ser Glu Thr Trp Ile Gly Leu Ser Ser Asn Lys Ile Pro Val
                435                 440                 445

Ser Phe Glu Trp Ser Asn Asp Ser Ser Val Ile Phe Thr Asn Trp His
450                 455                 460

Thr Leu Glu Pro His Ile Phe Pro Asn Arg Ser Gln Leu Cys Val Ser
465                 470                 475                 480

Ala Glu Gln Ser Glu Gly His Trp Lys Val Lys Asn Cys Glu Glu Arg
                485                 490                 495

Leu Phe Tyr Ile Cys Lys Lys Ala Gly His Val Leu Ser Asp Ala Glu
                500                 505                 510

Ser Gly Cys Gln Glu Gly Trp Glu Arg His Gly Gly Phe Cys Tyr Lys
                515                 520                 525

Ile Asp Thr Val Leu Arg Ser Phe Asp Gln Ala Ser Ser Gly Tyr Tyr
530                 535                 540
```

Cys Pro Pro Ala Leu Val Thr Ile Thr Asn Arg Phe Glu Gln Ala Phe
545                 550                 555                 560

Ile Thr Ser Leu Ile Ser Ser Val Val Lys Met Lys Asp Ser Tyr Phe
            565                 570                 575

Trp Ile Ala Leu Gln Asp Gln Asn Asp Thr Gly Glu Tyr Thr Trp Lys
        580                 585                 590

Pro Val Gly Gln Lys Pro Glu Pro Val Gln Tyr Thr His Trp Asn Thr
            595                 600                 605

His Gln Pro Arg Tyr Ser Gly Gly Cys Val Ala Met Arg Gly Arg His
        610                 615                 620

Pro Leu Gly Arg Trp Glu Val Lys His Cys Arg His Phe Lys Ala Met
625                 630                 635                 640

Ser Leu Cys Lys Gln Pro Val Glu Asn Gln Glu Lys Ala Glu Tyr Glu
            645                 650                 655

Glu Arg Trp Pro Phe His Pro Cys Tyr Leu Asp Trp Glu Ser Glu Pro
        660                 665                 670

Gly Leu Ala Ser Cys Phe Lys Val Phe His Ser Glu Lys Val Leu Met
        675                 680                 685

Lys Arg Thr Trp Arg Glu Ala Glu Ala Phe Cys Glu Glu Phe Gly Ala
690                 695                 700

His Leu Ala Ser Phe Ala His Ile Glu Glu Glu Asn Phe Val Asn Glu
705                 710                 715                 720

Leu Leu His Ser Lys Phe Asn Trp Thr Glu Arg Gln Phe Trp Ile
            725                 730                 735

Gly Phe Asn Lys Arg Asn Pro Leu Asn Ala Gly Ser Trp Glu Trp Ser
            740                 745                 750

Asp Arg Thr Pro Val Val Ser Ser Phe Leu Asp Asn Thr Tyr Phe Gly
            755                 760                 765

Glu Asp Ala Arg Asn Cys Ala Val Tyr Lys Ala Asn Lys Thr Leu Leu
        770                 775                 780

Pro Leu His Cys Gly Ser Lys Arg Glu Trp Ile Cys Lys Ile Pro Arg
785                 790                 795                 800

Asp Val Lys Pro Lys
            805

<210> SEQ ID NO 5
<211> LENGTH: 367
<212> TYPE: PRT
<213> ORGANISM: Artificial
<220> FEATURE:
<223> OTHER INFORMATION: Synthetic

<400> SEQUENCE: 5

Met Leu Leu Ser Pro Ser Leu Leu Leu Leu Leu Leu Gly Ala Pro
1               5                   10                  15

Arg Gly Cys Ala Glu Gly Val Ala Ala Ala Leu Thr Pro Glu Arg Leu
            20                  25                  30

Leu Glu Trp Gln Asp Lys Gly Ile Phe Val Ile Gln Ser Glu Ser Leu
        35                  40                  45

Lys Lys Cys Ile Gln Ala Gly Lys Ser Val Leu Thr Leu Glu Asn Cys
50                  55                  60

Lys Gln Ala Asn Lys His Met Leu Trp Lys Trp Val Ser Asn His Gly
65                  70                  75                  80

Leu Phe Asn Ile Gly Gly Ser Gly Cys Leu Gly Leu Asn Phe Ser Ala
            85                  90                  95

```
Pro Glu Gln Pro Leu Ser Leu Tyr Glu Cys Asp Ser Thr Leu Val Ser
                100                 105                 110

Leu Arg Trp Arg Cys Asn Arg Lys Met Ile Thr Gly Pro Leu Gln Tyr
            115                 120                 125

Ser Val Gln Val Ala His Asp Asn Thr Val Val Ala Ser Arg Lys Tyr
        130                 135                 140

Ile His Lys Trp Ile Ser Tyr Gly Ser Gly Gly Asp Ile Cys Glu
145                 150                 155                 160

Tyr Leu His Lys Asp Leu His Thr Ile Lys Gly Asn Thr His Gly Met
                165                 170                 175

Pro Cys Met Phe Pro Phe Gln Tyr Asn His Gln Trp His His Glu Cys
            180                 185                 190

Thr Arg Glu Gly Arg Glu Asp Asp Leu Leu Trp Cys Ala Thr Thr Ser
        195                 200                 205

Arg Tyr Glu Arg Asp Glu Lys Trp Gly Phe Cys Pro Asp Pro Thr Ser
        210                 215                 220

Ala Glu Val Gly Cys Asp Thr Ile Trp Glu Lys Asp Leu Asn Ser His
225                 230                 235                 240

Ile Cys Tyr Gln Phe Asn Leu Leu Ser Ser Leu Ser Trp Ser Glu Ala
            245                 250                 255

His Ser Ser Cys Gln Met Gln Gly Gly Thr Leu Leu Ser Ile Thr Asp
            260                 265                 270

Glu Thr Glu Glu Asn Phe Ile Arg Glu His Met Ser Ser Lys Thr Val
            275                 280                 285

Glu Val Trp Met Gly Leu Asn Gln Leu Asp Glu His Ala Gly Trp Gln
        290                 295                 300

Trp Ser Asp Gly Thr Pro Leu Asn Tyr Leu Asn Trp Ser Pro Glu Val
305                 310                 315                 320

Asn Phe Glu Pro Phe Val Asp His Cys Gly Thr Phe Ser Ser Phe
            325                 330                 335

Met Pro Ser Ala Trp Arg Ser Arg Asp Cys Glu Ser Thr Leu Pro Tyr
            340                 345                 350

Ile Cys Lys Lys Tyr Leu Asn His Ile Asp His Glu Ile Val Glu
        355                 360                 365

<210> SEQ ID NO 6
<211> LENGTH: 438
<212> TYPE: PRT
<213> ORGANISM: Artificial
<220> FEATURE:
<223> OTHER INFORMATION: Synthetic

<400> SEQUENCE: 6

Lys Asp Ala Trp Lys Tyr Tyr Ala Thr His Cys Glu Pro Gly Trp Asn
1               5                   10                  15

Pro Tyr Asn Arg Asn Cys Tyr Lys Leu Gln Lys Glu Lys Thr Trp
            20                  25                  30

His Glu Ala Leu Arg Ser Cys Gln Ala Asp Asn Ser Ala Leu Ile Asp
        35                  40                  45

Ile Thr Ser Leu Ala Glu Val Glu Phe Leu Val Thr Leu Leu Gly Asp
    50                  55                  60

Glu Asn Ala Ser Glu Thr Trp Ile Gly Leu Ser Ser Asn Lys Ile Pro
65                  70                  75                  80

Val Ser Phe Glu Trp Ser Asn Asp Ser Ser Val Ile Phe Thr Asn Trp
                85                  90                  95
```

His Thr Leu Glu Pro His Ile Phe Pro Asn Arg Ser Gln Leu Cys Val
            100                 105                 110

Ser Ala Glu Gln Ser Glu Gly His Trp Lys Val Lys Asn Cys Glu Glu
        115                 120                 125

Arg Leu Phe Tyr Ile Cys Lys Lys Ala Gly His Val Leu Ser Asp Ala
    130                 135                 140

Glu Ser Gly Cys Gln Glu Gly Trp Glu Arg His Gly Gly Phe Cys Tyr
145                 150                 155                 160

Lys Ile Asp Thr Val Leu Arg Ser Phe Asp Gln Ala Ser Ser Gly Tyr
                165                 170                 175

Tyr Cys Pro Pro Ala Leu Val Thr Ile Thr Asn Arg Phe Glu Gln Ala
            180                 185                 190

Phe Ile Thr Ser Leu Ile Ser Ser Val Val Lys Met Lys Asp Ser Tyr
        195                 200                 205

Phe Trp Ile Ala Leu Gln Asp Gln Asn Asp Thr Gly Glu Tyr Thr Trp
    210                 215                 220

Lys Pro Val Gly Gln Lys Pro Glu Pro Val Gln Tyr Thr His Trp Asn
225                 230                 235                 240

Thr His Gln Pro Arg Tyr Ser Gly Gly Cys Val Ala Met Arg Gly Arg
                245                 250                 255

His Pro Leu Gly Arg Trp Glu Val Lys His Cys Arg His Phe Lys Ala
            260                 265                 270

Met Ser Leu Cys Lys Gln Pro Val Glu Asn Gln Glu Lys Ala Glu Tyr
        275                 280                 285

Glu Glu Arg Trp Pro Phe His Pro Cys Tyr Leu Asp Trp Glu Ser Glu
    290                 295                 300

Pro Gly Leu Ala Ser Cys Phe Lys Val Phe His Ser Glu Lys Val Leu
305                 310                 315                 320

Met Lys Arg Thr Trp Arg Glu Ala Glu Ala Phe Cys Glu Glu Phe Gly
                325                 330                 335

Ala His Leu Ala Ser Phe Ala His Ile Glu Glu Glu Asn Phe Val Asn
            340                 345                 350

Glu Leu Leu His Ser Lys Phe Asn Trp Thr Glu Glu Arg Gln Phe Trp
        355                 360                 365

Ile Gly Phe Asn Lys Arg Asn Pro Leu Asn Ala Gly Ser Trp Glu Trp
    370                 375                 380

Ser Asp Arg Thr Pro Val Val Ser Ser Phe Leu Asp Asn Thr Tyr Phe
385                 390                 395                 400

Gly Glu Asp Ala Arg Asn Cys Ala Val Tyr Lys Ala Asn Lys Thr Leu
                405                 410                 415

Leu Pro Leu His Cys Gly Ser Lys Arg Glu Trp Ile Cys Lys Ile Pro
            420                 425                 430

Arg Asp Val Lys Pro Lys
        435

<210> SEQ ID NO 7
<211> LENGTH: 169
<212> TYPE: PRT
<213> ORGANISM: Artificial
<220> FEATURE:
<223> OTHER INFORMATION: Synthetic

<400> SEQUENCE: 7

Met Leu Leu Ser Pro Ser Leu Leu Leu Leu Leu Leu Gly Ala Pro
1               5                   10                  15

```
Arg Gly Cys Ala Glu Gly Val Ala Ala Ala Leu Thr Pro Glu Arg Leu
            20                  25                  30

Leu Glu Trp Gln Asp Lys Gly Ile Phe Val Ile Gln Ser Glu Ser Leu
        35                  40                  45

Lys Lys Cys Ile Gln Ala Gly Lys Ser Val Leu Thr Leu Glu Asn Cys
50                  55                  60

Lys Gln Ala Asn Lys His Met Leu Trp Lys Trp Val Ser Asn His Gly
65                  70                  75                  80

Leu Phe Asn Ile Gly Gly Ser Gly Cys Leu Gly Leu Asn Phe Ser Ala
                85                  90                  95

Pro Glu Gln Pro Leu Ser Leu Tyr Glu Cys Asp Ser Thr Leu Val Ser
            100                 105                 110

Leu Arg Trp Arg Cys Asn Arg Lys Met Ile Thr Gly Pro Leu Gln Tyr
        115                 120                 125

Ser Val Gln Val Ala His Asp Asn Thr Val Val Ala Ser Arg Lys Tyr
    130                 135                 140

Ile His Lys Trp Ile Ser Tyr Gly Ser Gly Gly Asp Ile Cys Glu
145                 150                 155                 160

Tyr Leu His Lys Asp Leu His Thr Ile
                165
```

```
<210> SEQ ID NO 8
<211> LENGTH: 228
<212> TYPE: PRT
<213> ORGANISM: Artificial
<220> FEATURE:
<223> OTHER INFORMATION: Synthetic

<400> SEQUENCE: 8

Met Leu Leu Ser Pro Ser Leu Leu Leu Leu Leu Leu Gly Ala Pro
1               5                   10                  15

Arg Gly Cys Ala Glu Gly Val Ala Ala Ala Leu Thr Pro Glu Arg Leu
            20                  25                  30

Leu Glu Trp Gln Asp Lys Gly Ile Phe Val Ile Gln Ser Glu Ser Leu
        35                  40                  45

Lys Lys Cys Ile Gln Ala Gly Lys Ser Val Leu Thr Leu Glu Asn Cys
50                  55                  60

Lys Gln Ala Asn Lys His Met Leu Trp Lys Trp Val Ser Asn His Gly
65                  70                  75                  80

Leu Phe Asn Ile Gly Gly Ser Gly Cys Leu Gly Leu Asn Phe Ser Ala
                85                  90                  95

Pro Glu Gln Pro Leu Ser Leu Tyr Glu Cys Asp Ser Thr Leu Val Ser
            100                 105                 110

Leu Arg Trp Arg Cys Asn Arg Lys Met Ile Thr Gly Pro Leu Gln Tyr
        115                 120                 125

Ser Val Gln Val Ala His Asp Asn Thr Val Val Ala Ser Arg Lys Tyr
    130                 135                 140

Ile His Lys Trp Ile Ser Tyr Gly Ser Gly Gly Asp Ile Cys Glu
145                 150                 155                 160

Tyr Leu His Lys Asp Leu His Thr Ile Lys Gly Asn Thr His Gly Met
                165                 170                 175

Pro Cys Met Phe Pro Phe Gln Tyr Asn His Gln Trp His His Glu Cys
            180                 185                 190

Thr Arg Glu Gly Arg Glu Asp Asp Leu Leu Trp Cys Ala Thr Thr Ser
        195                 200                 205
```

Arg Tyr Glu Arg Asp Glu Lys Trp Gly Phe Cys Pro Asp Pro Thr Ser
210                 215                 220

Ala Glu Val Gly
225

<210> SEQ ID NO 9
<211> LENGTH: 367
<212> TYPE: PRT
<213> ORGANISM: Artificial
<220> FEATURE:
<223> OTHER INFORMATION: Synthetic

<400> SEQUENCE: 9

Met Leu Leu Ser Pro Ser Leu Leu Leu Leu Leu Leu Gly Ala Pro
1               5                   10                  15

Arg Gly Cys Ala Glu Gly Val Ala Ala Leu Thr Pro Glu Arg Leu
            20                  25                  30

Leu Glu Trp Gln Asp Lys Gly Ile Phe Val Ile Gln Ser Glu Ser Leu
        35                  40                  45

Lys Lys Cys Ile Gln Ala Gly Lys Ser Val Leu Thr Leu Glu Asn Cys
    50                  55                  60

Lys Gln Ala Asn Lys His Met Leu Trp Lys Trp Val Ser Asn His Gly
65                  70                  75                  80

Leu Phe Asn Ile Gly Gly Ser Gly Cys Leu Gly Leu Asn Phe Ser Ala
                85                  90                  95

Pro Glu Gln Pro Leu Ser Leu Tyr Glu Cys Asp Ser Thr Leu Val Ser
                100                 105                 110

Leu Arg Trp Arg Cys Asn Arg Lys Met Ile Thr Gly Pro Leu Gln Tyr
            115                 120                 125

Ser Val Gln Val Ala His Asp Asn Thr Val Val Ala Ser Arg Lys Tyr
    130                 135                 140

Ile His Lys Trp Ile Ser Tyr Gly Ser Gly Gly Gly Asp Ile Cys Glu
145                 150                 155                 160

Tyr Leu His Lys Asp Leu His Thr Ile Lys Gly Asn Thr His Gly Met
                165                 170                 175

Pro Cys Met Phe Pro Phe Gln Tyr Asn His Gln Trp His His Glu Cys
            180                 185                 190

Thr Arg Glu Gly Arg Glu Asp Asp Leu Leu Trp Cys Ala Thr Thr Ser
        195                 200                 205

Arg Tyr Glu Arg Asp Glu Lys Trp Gly Phe Cys Pro Asp Pro Thr Ser
    210                 215                 220

Ala Glu Val Gly Cys Asp Thr Ile Trp Glu Lys Asp Leu Asn Ser His
225                 230                 235                 240

Ile Cys Tyr Gln Phe Asn Leu Leu Ser Ser Leu Ser Trp Ser Glu Ala
                245                 250                 255

His Ser Ser Cys Gln Met Gln Gly Gly Thr Leu Leu Ser Ile Thr Asp
            260                 265                 270

Glu Thr Glu Glu Asn Phe Ile Arg Glu His Met Ser Ser Lys Thr Val
        275                 280                 285

Glu Val Trp Met Gly Leu Asn Gln Leu Asp Glu His Ala Gly Trp Gln
    290                 295                 300

Trp Ser Asp Gly Thr Pro Leu Asn Tyr Leu Asn Trp Ser Pro Glu Val
305                 310                 315                 320

Asn Phe Glu Pro Phe Val Glu Asp His Cys Gly Thr Phe Ser Ser Phe
                325                 330                 335

Met Pro Ser Ala Trp Arg Ser Arg Asp Cys Glu Ser Thr Leu Pro Tyr
                340                 345                 350

Ile Cys Lys Lys Tyr Leu Asn His Ile Asp His Glu Ile Val Glu
        355                 360                 365

<210> SEQ ID NO 10
<211> LENGTH: 510
<212> TYPE: PRT
<213> ORGANISM: Artificial
<220> FEATURE:
<223> OTHER INFORMATION: Synthetic

<400> SEQUENCE: 10

Met Leu Leu Ser Pro Ser Leu Leu Leu Leu Leu Leu Gly Ala Pro
1               5                   10                  15

Arg Gly Cys Ala Glu Gly Val Ala Ala Ala Leu Thr Pro Glu Arg Leu
                20                  25                  30

Leu Glu Trp Gln Asp Lys Gly Ile Phe Val Ile Gln Ser Glu Ser Leu
            35                  40                  45

Lys Lys Cys Ile Gln Ala Gly Lys Ser Val Leu Thr Leu Glu Asn Cys
        50                  55                  60

Lys Gln Ala Asn Lys His Met Leu Trp Lys Trp Val Ser Asn His Gly
65                  70                  75                  80

Leu Phe Asn Ile Gly Gly Ser Gly Cys Leu Gly Leu Asn Phe Ser Ala
                85                  90                  95

Pro Glu Gln Pro Leu Ser Leu Tyr Glu Cys Asp Ser Thr Leu Val Ser
                100                 105                 110

Leu Arg Trp Arg Cys Asn Arg Lys Met Ile Thr Gly Pro Leu Gln Tyr
            115                 120                 125

Ser Val Gln Val Ala His Asp Asn Thr Val Val Ala Ser Arg Lys Tyr
        130                 135                 140

Ile His Lys Trp Ile Ser Tyr Gly Ser Gly Gly Gly Asp Ile Cys Glu
145                 150                 155                 160

Tyr Leu His Lys Asp Leu His Thr Ile Lys Gly Asn Thr His Gly Met
                165                 170                 175

Pro Cys Met Phe Pro Phe Gln Tyr Asn His Gln Trp His His Glu Cys
                180                 185                 190

Thr Arg Glu Gly Arg Glu Asp Asp Leu Leu Trp Cys Ala Thr Thr Ser
            195                 200                 205

Arg Tyr Glu Arg Asp Glu Lys Trp Gly Phe Cys Pro Asp Pro Thr Ser
        210                 215                 220

Ala Glu Val Gly Cys Asp Thr Ile Trp Glu Lys Asp Leu Asn Ser His
225                 230                 235                 240

Ile Cys Tyr Gln Phe Asn Leu Leu Ser Ser Leu Ser Trp Ser Glu Ala
                245                 250                 255

His Ser Ser Cys Gln Met Gln Gly Gly Thr Leu Leu Ser Ile Thr Asp
                260                 265                 270

Glu Thr Glu Glu Asn Phe Ile Arg Glu His Met Ser Ser Lys Thr Val
            275                 280                 285

Glu Val Trp Met Gly Leu Asn Gln Leu Asp Glu His Ala Gly Trp Gln
        290                 295                 300

Trp Ser Asp Gly Thr Pro Leu Asn Tyr Leu Asn Trp Ser Pro Glu Val
305                 310                 315                 320

Asn Phe Glu Pro Phe Val Glu Asp His Cys Gly Thr Phe Ser Ser Phe
                325                 330                 335

```
Met Pro Ser Ala Trp Arg Ser Arg Asp Cys Glu Ser Thr Leu Pro Tyr
                340                 345                 350

Ile Cys Lys Lys Tyr Leu Asn His Ile Asp His Glu Ile Val Glu Lys
                355                 360                 365

Asp Ala Trp Lys Tyr Tyr Ala Thr His Cys Glu Pro Gly Trp Asn Pro
            370                 375                 380

Tyr Asn Arg Asn Cys Tyr Lys Leu Gln Lys Glu Lys Thr Trp His
385                 390                 395                 400

Glu Ala Leu Arg Ser Cys Gln Ala Asp Asn Ser Ala Leu Ile Asp Ile
                405                 410                 415

Thr Ser Leu Ala Glu Val Glu Phe Leu Val Thr Leu Leu Gly Asp Glu
            420                 425                 430

Asn Ala Ser Glu Thr Trp Ile Gly Leu Ser Ser Asn Lys Ile Pro Val
            435                 440                 445

Ser Phe Glu Trp Ser Asn Asp Ser Ser Val Ile Phe Thr Asn Trp His
        450                 455                 460

Thr Leu Glu Pro His Ile Phe Pro Asn Arg Ser Gln Leu Cys Val Ser
465                 470                 475                 480

Ala Glu Gln Ser Glu Gly His Trp Lys Val Lys Asn Cys Glu Arg
                485                 490                 495

Leu Phe Tyr Ile Cys Lys Lys Ala Gly His Val Leu Ser Asp
            500                 505                 510

<210> SEQ ID NO 11
<211> LENGTH: 651
<212> TYPE: PRT
<213> ORGANISM: Artificial
<220> FEATURE:
<223> OTHER INFORMATION: Synthetic

<400> SEQUENCE: 11

Met Leu Leu Ser Pro Ser Leu Leu Leu Leu Leu Leu Gly Ala Pro
1               5                   10                  15

Arg Gly Cys Ala Glu Gly Val Ala Ala Ala Leu Thr Pro Glu Arg Leu
                20                  25                  30

Leu Glu Trp Gln Asp Lys Gly Ile Phe Val Ile Gln Ser Glu Ser Leu
            35                  40                  45

Lys Lys Cys Ile Gln Ala Gly Lys Ser Val Leu Thr Leu Glu Asn Cys
        50                  55                  60

Lys Gln Ala Asn Lys His Met Leu Trp Lys Trp Val Ser Asn His Gly
65                  70                  75                  80

Leu Phe Asn Ile Gly Gly Ser Gly Cys Leu Gly Leu Asn Phe Ser Ala
                85                  90                  95

Pro Glu Gln Pro Leu Ser Leu Tyr Glu Cys Asp Ser Thr Leu Val Ser
            100                 105                 110

Leu Arg Trp Arg Cys Asn Arg Lys Met Ile Thr Gly Pro Leu Gln Tyr
        115                 120                 125

Ser Val Gln Val Ala His Asp Asn Thr Val Val Ala Ser Arg Lys Tyr
    130                 135                 140

Ile His Lys Trp Ile Ser Tyr Gly Ser Gly Gly Asp Ile Cys Glu
145                 150                 155                 160

Tyr Leu His Lys Asp Leu His Thr Ile Lys Gly Asn Thr His Gly Met
                165                 170                 175

Pro Cys Met Phe Pro Phe Gln Tyr Asn His Gln Trp His His Glu Cys
            180                 185                 190
```

-continued

```
Thr Arg Glu Gly Arg Glu Asp Asp Leu Leu Trp Cys Ala Thr Thr Ser
            195                 200                 205
Arg Tyr Glu Arg Asp Glu Lys Trp Gly Phe Cys Pro Asp Pro Thr Ser
        210                 215                 220
Ala Glu Val Gly Cys Asp Thr Ile Trp Glu Lys Asp Leu Asn Ser His
225                 230                 235                 240
Ile Cys Tyr Gln Phe Asn Leu Leu Ser Ser Leu Ser Trp Ser Glu Ala
                245                 250                 255
His Ser Ser Cys Gln Met Gln Gly Gly Thr Leu Leu Ser Ile Thr Asp
            260                 265                 270
Glu Thr Glu Glu Asn Phe Ile Arg Glu His Met Ser Ser Lys Thr Val
        275                 280                 285
Glu Val Trp Met Gly Leu Asn Gln Leu Asp Glu His Ala Gly Trp Gln
    290                 295                 300
Trp Ser Asp Gly Thr Pro Leu Asn Tyr Leu Asn Trp Ser Pro Glu Val
305                 310                 315                 320
Asn Phe Glu Pro Phe Val Glu Asp His Cys Gly Thr Phe Ser Ser Phe
                325                 330                 335
Met Pro Ser Ala Trp Arg Ser Arg Asp Cys Glu Ser Thr Leu Pro Tyr
            340                 345                 350
Ile Cys Lys Lys Tyr Leu Asn His Ile Asp His Glu Ile Val Glu Lys
        355                 360                 365
Asp Ala Trp Lys Tyr Tyr Ala Thr His Cys Glu Pro Gly Trp Asn Pro
    370                 375                 380
Tyr Asn Arg Asn Cys Tyr Lys Leu Gln Lys Glu Glu Lys Thr Trp His
385                 390                 395                 400
Glu Ala Leu Arg Ser Cys Gln Ala Asp Asn Ser Ala Leu Ile Asp Ile
                405                 410                 415
Thr Ser Leu Ala Glu Val Glu Phe Leu Val Thr Leu Leu Gly Asp Glu
            420                 425                 430
Asn Ala Ser Glu Thr Trp Ile Gly Leu Ser Ser Asn Lys Ile Pro Val
        435                 440                 445
Ser Phe Glu Trp Ser Asn Asp Ser Ser Val Ile Phe Thr Asn Trp His
    450                 455                 460
Thr Leu Glu Pro His Ile Phe Pro Asn Arg Ser Gln Leu Cys Val Ser
465                 470                 475                 480
Ala Glu Gln Ser Glu Gly His Trp Lys Val Lys Asn Cys Glu Glu Arg
                485                 490                 495
Leu Phe Tyr Ile Cys Lys Lys Ala Gly His Val Leu Ser Asp Ala Glu
            500                 505                 510
Ser Gly Cys Gln Glu Gly Trp Glu Arg His Gly Gly Phe Cys Tyr Lys
        515                 520                 525
Ile Asp Thr Val Leu Arg Ser Phe Asp Gln Ala Ser Ser Gly Tyr Tyr
    530                 535                 540
Cys Pro Pro Ala Leu Val Thr Ile Thr Asn Arg Phe Glu Gln Ala Phe
545                 550                 555                 560
Ile Thr Ser Leu Ile Ser Ser Val Val Lys Met Lys Asp Ser Tyr Phe
                565                 570                 575
Trp Ile Ala Leu Gln Asp Gln Asn Asp Thr Gly Glu Tyr Thr Trp Lys
            580                 585                 590
Pro Val Gly Gln Lys Pro Glu Pro Val Gln Tyr Thr His Trp Asn Thr
        595                 600                 605
His Gln Pro Arg Tyr Ser Gly Gly Cys Val Ala Met Arg Gly Arg His
```

```
            610                 615                 620
Pro Leu Gly Arg Trp Glu Val Lys His Cys Arg His Phe Lys Ala Met
625                 630                 635                 640

Ser Leu Cys Lys Gln Pro Val Glu Asn Gln Glu
                645                 650

<210> SEQ ID NO 12
<211> LENGTH: 805
<212> TYPE: PRT
<213> ORGANISM: Artificial
<220> FEATURE:
<223> OTHER INFORMATION: Synthetic

<400> SEQUENCE: 12

Met Leu Leu Ser Pro Ser Leu Leu Leu Leu Leu Gly Ala Pro
1               5                   10                  15

Arg Gly Cys Ala Glu Gly Val Ala Ala Ala Leu Thr Pro Glu Arg Leu
                20                  25                  30

Leu Glu Trp Gln Asp Lys Gly Ile Phe Val Ile Gln Ser Glu Ser Leu
            35                  40                  45

Lys Lys Cys Ile Gln Ala Gly Lys Ser Val Leu Thr Leu Glu Asn Cys
50                  55                  60

Lys Gln Ala Asn Lys His Met Leu Trp Lys Trp Val Ser Asn His Gly
65                  70                  75                  80

Leu Phe Asn Ile Gly Gly Ser Gly Cys Leu Gly Leu Asn Phe Ser Ala
                85                  90                  95

Pro Glu Gln Pro Leu Ser Leu Tyr Glu Cys Asp Ser Thr Leu Val Ser
            100                 105                 110

Leu Arg Trp Arg Cys Asn Arg Lys Met Ile Thr Gly Pro Leu Gln Tyr
        115                 120                 125

Ser Val Gln Val Ala His Asp Asn Thr Val Val Ala Ser Arg Lys Tyr
130                 135                 140

Ile His Lys Trp Ile Ser Tyr Gly Ser Gly Gly Asp Ile Cys Glu
145                 150                 155                 160

Tyr Leu His Lys Asp Leu His Thr Ile Lys Gly Asn Thr His Gly Met
                165                 170                 175

Pro Cys Met Phe Pro Phe Gln Tyr Asn His Gln Trp His His Glu Cys
            180                 185                 190

Thr Arg Glu Gly Arg Glu Asp Asp Leu Leu Trp Cys Ala Thr Thr Ser
        195                 200                 205

Arg Tyr Glu Arg Asp Glu Lys Trp Gly Phe Cys Pro Asp Pro Thr Ser
210                 215                 220

Ala Glu Val Gly Cys Asp Thr Ile Trp Glu Lys Asp Leu Asn Ser His
225                 230                 235                 240

Ile Cys Tyr Gln Phe Asn Leu Leu Ser Ser Leu Ser Trp Ser Glu Ala
                245                 250                 255

His Ser Ser Cys Gln Met Gln Gly Gly Thr Leu Leu Ser Ile Thr Asp
            260                 265                 270

Glu Thr Glu Glu Asn Phe Ile Arg Glu His Met Ser Ser Lys Thr Val
        275                 280                 285

Glu Val Trp Met Gly Leu Asn Gln Leu Asp Glu His Ala Gly Trp Gln
290                 295                 300

Trp Ser Asp Gly Thr Pro Leu Asn Tyr Leu Asn Trp Ser Pro Glu Val
305                 310                 315                 320

Asn Phe Glu Pro Phe Val Glu Asp His Cys Gly Thr Phe Ser Ser Phe
```

```
                            325                 330                 335
        Met Pro Ser Ala Trp Arg Ser Arg Asp Cys Glu Ser Thr Leu Pro Tyr
                        340                 345                 350

Ile Cys Lys Lys Tyr Leu Asn His Ile Asp His Glu Ile Val Glu Lys
                        355                 360                 365

Asp Ala Trp Lys Tyr Tyr Ala Thr His Cys Glu Pro Gly Trp Asn Pro
                        370                 375                 380

Tyr Asn Arg Asn Cys Tyr Lys Leu Gln Lys Glu Glu Lys Thr Trp His
        385                 390                 395                 400

Glu Ala Leu Arg Ser Cys Gln Ala Asp Asn Ser Ala Leu Ile Asp Ile
                        405                 410                 415

Thr Ser Leu Ala Glu Val Glu Phe Leu Val Thr Leu Leu Gly Asp Glu
                        420                 425                 430

Asn Ala Ser Glu Thr Trp Ile Gly Leu Ser Ser Asn Lys Ile Pro Val
                        435                 440                 445

Ser Phe Glu Trp Ser Asn Asp Ser Ser Val Ile Phe Thr Asn Trp His
                        450                 455                 460

Thr Leu Glu Pro His Ile Phe Pro Asn Arg Ser Gln Leu Cys Val Ser
        465                 470                 475                 480

Ala Glu Gln Ser Glu Gly His Trp Lys Val Lys Asn Cys Glu Glu Arg
                        485                 490                 495

Leu Phe Tyr Ile Cys Lys Lys Ala Gly His Val Leu Ser Asp Ala Glu
                        500                 505                 510

Ser Gly Cys Gln Glu Gly Trp Glu Arg His Gly Gly Phe Cys Tyr Lys
                        515                 520                 525

Ile Asp Thr Val Leu Arg Ser Phe Asp Gln Ala Ser Ser Gly Tyr Tyr
                        530                 535                 540

Cys Pro Pro Ala Leu Val Thr Ile Thr Asn Arg Phe Glu Gln Ala Phe
        545                 550                 555                 560

Ile Thr Ser Leu Ile Ser Ser Val Val Lys Met Lys Asp Ser Tyr Phe
                        565                 570                 575

Trp Ile Ala Leu Gln Asp Gln Asn Asp Thr Gly Glu Tyr Thr Trp Lys
                        580                 585                 590

Pro Val Gly Gln Lys Pro Glu Pro Val Gln Tyr Thr His Trp Asn Thr
                        595                 600                 605

His Gln Pro Arg Tyr Ser Gly Gly Cys Val Ala Met Arg Gly Arg His
                        610                 615                 620

Pro Leu Gly Arg Trp Glu Val Lys His Cys Arg His Phe Lys Ala Met
        625                 630                 635                 640

Ser Leu Cys Lys Gln Pro Val Glu Asn Gln Glu Lys Ala Glu Tyr Glu
                        645                 650                 655

Glu Arg Trp Pro Phe His Pro Cys Tyr Leu Asp Trp Glu Ser Glu Pro
                        660                 665                 670

Gly Leu Ala Ser Cys Phe Lys Val Phe His Ser Glu Lys Val Leu Met
                        675                 680                 685

Lys Arg Thr Trp Arg Glu Ala Glu Ala Phe Cys Glu Glu Phe Gly Ala
        690                 695                 700

His Leu Ala Ser Phe Ala His Ile Glu Glu Asn Phe Val Asn Glu
        705                 710                 715                 720

Leu Leu His Ser Lys Phe Asn Trp Thr Glu Glu Arg Gln Phe Trp Ile
                        725                 730                 735

Gly Phe Asn Lys Arg Asn Pro Leu Asn Ala Gly Ser Trp Glu Trp Ser
                        740                 745                 750
```

```
Asp Arg Thr Pro Val Val Ser Ser Phe Leu Asp Asn Thr Tyr Phe Gly
        755                 760                 765

Glu Asp Ala Arg Asn Cys Ala Val Tyr Lys Ala Asn Lys Thr Leu Leu
        770                 775                 780

Pro Leu His Cys Gly Ser Lys Arg Glu Trp Ile Cys Lys Ile Pro Arg
785                 790                 795                 800

Asp Val Lys Pro Lys
            805

<210> SEQ ID NO 13
<211> LENGTH: 139
<212> TYPE: PRT
<213> ORGANISM: Artificial
<220> FEATURE:
<223> OTHER INFORMATION: Synthetic

<400> SEQUENCE: 13

Cys Asp Thr Ile Trp Glu Lys Asp Leu Asn Ser His Ile Cys Tyr Gln
1               5                   10                  15

Phe Asn Leu Leu Ser Ser Leu Ser Trp Ser Glu Ala His Ser Ser Cys
            20                  25                  30

Gln Met Gln Gly Gly Thr Leu Leu Ser Ile Thr Asp Glu Thr Glu Glu
        35                  40                  45

Asn Phe Ile Arg Glu His Met Ser Ser Lys Thr Val Glu Val Trp Met
    50                  55                  60

Gly Leu Asn Gln Leu Asp Glu His Ala Gly Trp Gln Trp Ser Asp Gly
65                  70                  75                  80

Thr Pro Leu Asn Tyr Leu Asn Trp Ser Pro Glu Val Asn Phe Glu Pro
                85                  90                  95

Phe Val Glu Asp His Cys Gly Thr Phe Ser Ser Phe Met Pro Ser Ala
            100                 105                 110

Trp Arg Ser Arg Asp Cys Glu Ser Thr Leu Pro Tyr Ile Cys Lys Lys
        115                 120                 125

Tyr Leu Asn His Ile Asp His Glu Ile Val Glu
    130                 135

<210> SEQ ID NO 14
<211> LENGTH: 1462
<212> TYPE: PRT
<213> ORGANISM: Artificial
<220> FEATURE:
<223> OTHER INFORMATION: Synthetic

<400> SEQUENCE: 14

Met Leu Leu Ser Pro Ser Leu Leu Leu Leu Leu Leu Leu Gly Ala Pro
1               5                   10                  15

Arg Gly Cys Ala Glu Gly Val Ala Ala Ala Leu Thr Pro Glu Arg Leu
            20                  25                  30

Leu Glu Trp Gln Asp Lys Gly Ile Phe Val Ile Gln Ser Glu Ser Leu
        35                  40                  45

Lys Lys Cys Ile Gln Ala Gly Lys Ser Val Leu Thr Leu Glu Asn Cys
    50                  55                  60

Lys Gln Ala Asn Lys His Met Leu Trp Lys Trp Val Ser Asn His Gly
65                  70                  75                  80

Leu Phe Asn Ile Gly Gly Ser Gly Cys Leu Gly Leu Asn Phe Ser Ala
                85                  90                  95

Pro Glu Gln Pro Leu Ser Leu Tyr Glu Cys Asp Ser Thr Leu Val Ser
```

```
             100                 105                110
Leu Arg Trp Arg Cys Asn Arg Lys Met Ile Thr Gly Pro Leu Gln Tyr
            115                 120                125

Ser Val Gln Val Ala His Asp Asn Thr Val Val Ala Ser Arg Lys Tyr
            130                 135                140

Ile His Lys Trp Ile Ser Tyr Gly Ser Gly Gly Asp Ile Cys Glu
145                 150                 155                160

Tyr Leu His Lys Asp Leu His Thr Ile Lys Gly Asn Thr His Gly Met
                165                 170                 175

Pro Cys Met Phe Pro Phe Gln Tyr Asn His Gln Trp His His Glu Cys
                180                 185                 190

Thr Arg Glu Gly Arg Glu Asp Asp Leu Leu Trp Cys Ala Thr Thr Ser
                195                 200                 205

Arg Tyr Glu Arg Asp Glu Lys Trp Gly Phe Cys Pro Asp Pro Thr Ser
                210                 215                 220

Ala Glu Val Gly Cys Asp Thr Ile Trp Glu Lys Asp Leu Asn Ser His
225                 230                 235                240

Ile Cys Tyr Gln Phe Asn Leu Leu Ser Ser Leu Ser Trp Ser Glu Ala
                245                 250                 255

His Ser Ser Gln Met Gln Gly Gly Thr Leu Leu Ser Ile Thr Asp Glu
                260                 265                 270

Thr Glu Glu Asn Phe Ile Arg Glu His Met Ser Ser Lys Thr Val Glu
                275                 280                 285

Val Trp Met Gly Leu Asn Gln Leu Asp Glu His Ala Gly Trp Gln Trp
            290                 295                 300

Ser Asp Gly Thr Pro Leu Asn Tyr Leu Asn Trp Ser Pro Glu Val Asn
305                 310                 315                 320

Phe Glu Pro Phe Val Glu Asp His Cys Gly Thr Phe Ser Ser Phe Met
                325                 330                 335

Pro Ser Ala Trp Arg Ser Arg Asp Cys Glu Ser Thr Leu Pro Tyr Ile
                340                 345                 350

Cys Lys Lys Tyr Leu Asn His Ile Asp His Glu Ile Val Glu Lys Asp
                355                 360                 365

Ala Trp Lys Tyr Tyr Ala Thr His Cys Glu Pro Gly Trp Asn Pro Tyr
                370                 375                 380

Asn Arg Asn Cys Tyr Lys Leu Gln Lys Glu Glu Lys Thr Trp His Glu
385                 390                 395                 400

Ala Leu Arg Ser Cys Gln Ala Asp Asn Ser Ala Leu Ile Asp Ile Thr
                405                 410                 415

Ser Leu Ala Glu Val Glu Phe Leu Val Thr Leu Leu Gly Asp Glu Asn
                420                 425                 430

Ala Ser Glu Thr Trp Ile Gly Leu Ser Ser Asn Lys Ile Pro Val Ser
                435                 440                 445

Phe Glu Trp Ser Asn Asp Ser Ser Val Ile Phe Thr Asn Trp His Thr
450                 455                 460

Leu Glu Pro His Ile Phe Pro Asn Arg Ser Gln Leu Cys Val Ser Ala
465                 470                 475                 480

Glu Gln Ser Glu Gly His Trp Lys Val Lys Asn Cys Glu Glu Arg Leu
                485                 490                 495

Phe Tyr Ile Cys Lys Lys Ala Gly His Val Leu Ser Asp Ala Glu Ser
                500                 505                 510

Gly Cys Gln Glu Gly Trp Glu Arg His Gly Gly Phe Cys Tyr Lys Ile
                515                 520                 525
```

```
Asp Thr Val Leu Arg Ser Phe Asp Gln Ala Ser Ser Gly Tyr Tyr Cys
    530                 535                 540

Pro Pro Ala Leu Val Thr Ile Thr Asn Arg Phe Glu Gln Ala Phe Ile
545                 550                 555                 560

Thr Ser Leu Ile Ser Ser Val Val Lys Met Lys Asp Ser Tyr Phe Trp
                565                 570                 575

Ile Ala Leu Gln Asp Gln Asn Asp Thr Gly Glu Tyr Thr Trp Lys Pro
                580                 585                 590

Val Gly Gln Lys Pro Glu Pro Val Gln Tyr Thr His Trp Asn Thr His
            595                 600                 605

Gln Pro Arg Tyr Ser Gly Gly Cys Val Ala Met Arg Gly Arg His Pro
            610                 615                 620

Leu Gly Arg Trp Glu Val Lys His Cys Arg His Phe Lys Ala Met Ser
625                 630                 635                 640

Leu Cys Lys Gln Pro Val Glu Asn Gln Glu Lys Ala Glu Tyr Glu Glu
                645                 650                 655

Arg Trp Pro Phe His Pro Cys Tyr Leu Asp Trp Glu Ser Glu Pro Gly
                660                 665                 670

Leu Ala Ser Cys Phe Lys Val Phe His Ser Glu Lys Val Leu Met Lys
                675                 680                 685

Arg Thr Trp Arg Glu Ala Glu Ala Phe Cys Glu Glu Phe Gly Ala His
690                 695                 700

Leu Ala Ser Phe Ala His Ile Glu Glu Glu Asn Phe Val Asn Glu Leu
705                 710                 715                 720

Leu His Ser Lys Phe Asn Trp Thr Glu Glu Arg Gln Phe Trp Ile Gly
                725                 730                 735

Phe Asn Lys Arg Asn Pro Leu Asn Ala Gly Ser Trp Glu Trp Ser Asp
                740                 745                 750

Arg Thr Pro Val Val Ser Ser Phe Leu Asp Asn Thr Tyr Phe Gly Glu
                755                 760                 765

Asp Ala Arg Asn Cys Ala Val Tyr Lys Ala Asn Lys Thr Leu Leu Pro
                770                 775                 780

Leu His Cys Gly Ser Lys Arg Glu Trp Ile Cys Lys Ile Pro Arg Asp
785                 790                 795                 800

Val Lys Pro Lys Ile Pro Phe Trp Tyr Gln Tyr Asp Val Pro Trp Leu
                805                 810                 815

Phe Tyr Gln Asp Ala Glu Tyr Leu Phe His Thr Phe Ala Ser Glu Trp
                820                 825                 830

Leu Asn Phe Glu Phe Val Cys Ser Trp Leu His Ser Asp Leu Leu Thr
                835                 840                 845

Ile His Ser Ala His Glu Gln Glu Phe Ile His Ser Lys Ile Lys Ala
            850                 855                 860

Leu Ser Lys Tyr Gly Ala Ser Trp Trp Ile Gly Leu Gln Glu Glu Arg
865                 870                 875                 880

Ala Asn Asp Glu Phe Arg Trp Arg Asp Gly Thr Pro Val Ile Tyr Gln
                885                 890                 895

Asn Trp Asp Thr Gly Arg Glu Arg Thr Val Asn Asn Gln Ser Gln Arg
                900                 905                 910

Cys Gly Phe Ile Ser Ser Ile Thr Gly Leu Trp Gly Ser Glu Glu Cys
            915                 920                 925

Ser Val Ser Met Pro Ser Ile Cys Lys Arg Lys Val Trp Leu Ile
            930                 935                 940
```

-continued

```
Glu Lys Lys Lys Asp Thr Pro Lys Gln His Gly Thr Cys Pro Lys Gly
945                 950                 955                 960

Trp Leu Tyr Phe Asn Tyr Lys Cys Leu Leu Asn Ile Pro Lys Asp
                965                 970                 975

Pro Ser Ser Trp Lys Asn Trp Thr His Ala Gln His Phe Cys Ala Glu
            980                 985                 990

Glu Gly Gly Thr Leu Val Ala Ile Glu Ser Glu Val Glu Gln Ala Phe
        995                 1000                1005

Ile Thr Met Asn Leu Phe Gly Gln Thr Thr Ser Val Trp Ile Gly
    1010                1015                1020

Leu Gln Asn Asp Asp Tyr Glu Thr Trp Leu Asn Gly Lys Pro Val
    1025                1030                1035

Val Tyr Ser Asn Trp Ser Pro Phe Asp Ile Ile Asn Ile Pro Ser
    1040                1045                1050

His Asn Thr Thr Glu Val Gln Lys His Ile Pro Leu Cys Ala Leu
    1055                1060                1065

Leu Ser Ser Asn Pro Asn Phe His Phe Thr Gly Lys Trp Tyr Phe
    1070                1075                1080

Glu Asp Cys Gly Lys Glu Gly Tyr Gly Phe Val Cys Glu Lys Met
    1085                1090                1095

Gln Asp Thr Ser Gly His Gly Val Asn Thr Ser Asp Met Tyr Pro
    1100                1105                1110

Met Pro Asn Thr Leu Glu Tyr Gly Asn Arg Thr Tyr Lys Ile Ile
    1115                1120                1125

Asn Ala Asn Met Thr Trp Tyr Ala Ala Ile Lys Thr Cys Leu Met
    1130                1135                1140

His Lys Ala Gln Leu Val Ser Ile Thr Asp Gln Tyr His Gln Ser
    1145                1150                1155

Phe Leu Thr Val Val Leu Asn Arg Leu Gly Tyr Ala His Trp Ile
    1160                1165                1170

Gly Leu Phe Thr Thr Asp Asn Gly Leu Asn Phe Asp Trp Ser Asp
    1175                1180                1185

Gly Thr Lys Ser Ser Phe Thr Phe Trp Lys Asp Glu Glu Ser Ser
    1190                1195                1200

Leu Leu Gly Asp Cys Val Phe Ala Asp Ser Asn Gly Arg Trp His
    1205                1210                1215

Ser Thr Ala Cys Glu Ser Phe Leu Gln Gly Ala Ile Cys His Val
    1220                1225                1230

Pro Pro Glu Thr Arg Gln Ser Glu His Pro Glu Leu Cys Ser Glu
    1235                1240                1245

Thr Ser Ile Pro Trp Ile Lys Phe Lys Ser Asn Cys Tyr Ser Phe
    1250                1255                1260

Ser Thr Val Leu Asp Ser Met Ser Phe Glu Ala Ala His Glu Phe
    1265                1270                1275

Cys Lys Lys Glu Gly Ser Asn Leu Leu Thr Ile Lys Asp Glu Ala
    1280                1285                1290

Glu Asn Ala Phe Leu Leu Glu Glu Leu Phe Ala Phe Gly Ser Ser
    1295                1300                1305

Val Gln Met Val Trp Leu Asn Ala Gln Phe Asp Gly Asn Asn Glu
    1310                1315                1320

Thr Ile Lys Trp Phe Asp Gly Thr Pro Thr Asp Gln Ser Asn Trp
    1325                1330                1335

Gly Ile Arg Lys Pro Asp Thr Asp Tyr Phe Lys Pro His His Cys
```

```
                    1340                1345                1350

Val  Ala  Leu  Arg  Ile  Pro  Glu  Gly  Leu  Trp  Gln  Leu  Ser  Pro  Cys
                    1355                1360                1365

Gln  Glu  Lys  Lys  Gly  Phe  Ile  Cys  Lys  Met  Glu  Ala  Asp  Ile  His
                    1370                1375                1380

Thr  Ala  Glu  Ala  Leu  Pro  Glu  Lys  Gly  Pro  Ser  His  Ser  Ile  Ile
                    1385                1390                1395

Pro  Leu  Ala  Val  Val  Leu  Thr  Leu  Ile  Val  Ile  Val  Ala  Ile  Cys
                    1400                1405                1410

Thr  Leu  Ser  Phe  Cys  Ile  Tyr  Lys  His  Asn  Gly  Gly  Phe  Phe  Arg
                    1415                1420                1425

Arg  Leu  Ala  Gly  Phe  Arg  Asn  Pro  Tyr  Tyr  Pro  Ala  Thr  Asn  Phe
                    1430                1435                1440

Ser  Thr  Val  Tyr  Leu  Glu  Glu  Asn  Ile  Leu  Ile  Ser  Asp  Leu  Glu
                    1445                1450                1455

Lys  Ser  Asp  Gln
     1460

<210> SEQ ID NO 15
<211> LENGTH: 272
<212> TYPE: PRT
<213> ORGANISM: Artificial
<220> FEATURE:
<223> OTHER INFORMATION: Synthetic

<400> SEQUENCE: 15

Met  Asp  Ser  Tyr  Leu  Leu  Met  Trp  Gly  Leu  Leu  Thr  Phe  Ile  Met  Val
1                  5                   10                  15

Pro  Gly  Cys  Gln  Ala  Glu  Leu  Cys  Asp  Asp  Asp  Pro  Pro  Glu  Ile  Pro
                   20                  25                  30

His  Ala  Thr  Phe  Lys  Ala  Met  Ala  Tyr  Lys  Glu  Gly  Thr  Met  Leu  Asn
              35                  40                  45

Cys  Glu  Cys  Lys  Arg  Gly  Phe  Arg  Arg  Ile  Lys  Ser  Gly  Ser  Leu  Tyr
     50                  55                  60

Met  Leu  Cys  Thr  Gly  Asn  Ser  Ser  His  Ser  Ser  Trp  Asp  Asn  Gln  Cys
65                  70                  75                  80

Gln  Cys  Thr  Ser  Ser  Ala  Thr  Arg  Asn  Thr  Thr  Lys  Gln  Val  Thr  Pro
              85                  90                  95

Gln  Pro  Glu  Glu  Gln  Lys  Glu  Arg  Lys  Thr  Thr  Glu  Met  Gln  Ser  Pro
                   100                 105                 110

Met  Gln  Pro  Val  Asp  Gln  Ala  Ser  Leu  Pro  Gly  His  Cys  Arg  Glu  Pro
              115                 120                 125

Pro  Pro  Trp  Glu  Asn  Glu  Ala  Thr  Glu  Arg  Ile  Tyr  His  Phe  Val  Val
         130                 135                 140

Gly  Gln  Met  Val  Tyr  Tyr  Gln  Cys  Val  Gln  Gly  Tyr  Arg  Ala  Leu  His
145                 150                 155                 160

Arg  Gly  Pro  Ala  Glu  Ser  Val  Cys  Lys  Met  Thr  His  Gly  Lys  Thr  Arg
                   165                 170                 175

Trp  Thr  Gln  Pro  Gln  Leu  Ile  Cys  Thr  Gly  Glu  Met  Glu  Thr  Ser  Gln
              180                 185                 190

Phe  Pro  Gly  Glu  Glu  Lys  Pro  Gln  Ala  Ser  Pro  Glu  Gly  Arg  Pro  Glu
         195                 200                 205

Ser  Glu  Thr  Ser  Cys  Leu  Val  Thr  Thr  Thr  Asp  Phe  Gln  Ile  Gln  Thr
     210                 215                 220

Glu  Met  Ala  Ala  Thr  Met  Glu  Thr  Ser  Ile  Phe  Thr  Thr  Glu  Tyr  Gln
```

```
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
                260                 265                 270

<210> SEQ ID NO 16
<211> LENGTH: 336
<212> TYPE: PRT
<213> ORGANISM: Artificial
<220> FEATURE:
<223> OTHER INFORMATION: Synthetic

<400> SEQUENCE: 16

Glu Trp Ile Lys Phe Ala Ala Ala Cys Arg Glu Gly Glu Asp Asn Ser
1               5                   10                  15

Lys Arg Asn Pro Ile Ala Lys Ile His Ser Asp Cys Ala Ala Asn Gln
                20                  25                  30

Gln Val Thr Tyr Arg Ile Ser Gly Val Gly Ile Asp Gln Pro Pro Tyr
            35                  40                  45

Gly Ile Phe Val Ile Asn Gln Lys Thr Gly Glu Ile Asn Ile Thr Ser
        50                  55                  60

Ile Val Asp Arg Glu Val Thr Pro Phe Phe Ile Ile Tyr Cys Arg Ala
65                  70                  75                  80

Leu Asn Ser Met Gly Gln Asp Leu Glu Arg Pro Leu Glu Leu Arg Val
                85                  90                  95

Arg Val Leu Asp Ile Asn Asp Asn Pro Pro Val Phe Ser Met Ala Thr
                100                 105                 110

Phe Ala Gly Gln Ile Glu Glu Asn Ser Asn Ala Asn Thr Leu Val Met
            115                 120                 125

Ile Leu Asn Ala Thr Asp Ala Asp Glu Pro Asn Asn Leu Asn Ser Lys
        130                 135                 140

Ile Ala Phe Lys Ile Ile Arg Gln Glu Pro Ser Asp Ser Pro Met Phe
145                 150                 155                 160

Ile Ile Asn Arg Asn Thr Gly Glu Ile Arg Thr Met Asn Asn Phe Leu
                165                 170                 175

Asp Arg Glu Gln Tyr Gly Gln Tyr Ala Leu Ala Val Arg Gly Ser Asp
                180                 185                 190

Arg Asp Gly Gly Ala Asp Gly Met Ser Ala Glu Cys Glu Cys Asn Ile
            195                 200                 205

Lys Ile Leu Asp Val Asn Asp Asn Ile Pro Tyr Met Glu Gln Ser Ser
        210                 215                 220

Tyr Thr Ile Glu Ile Gln Glu Asn Thr Leu Asn Ser Asn Leu Leu Glu
225                 230                 235                 240

Ile Arg Val Ile Asp Leu Asp Glu Glu Phe Ser Ala Asn Trp Met Ala
                245                 250                 255

Val Ile Phe Phe Ile Ser Gly Asn Glu Gly Asn Trp Phe Glu Ile Glu
                260                 265                 270

Met Asn Glu Arg Thr Asn Val Gly Ile Leu Lys Val Lys Pro Leu
            275                 280                 285

Asp Tyr Glu Ala Met Gln Ser Leu Gln Leu Ser Ile Gly Val Arg Asn
            290                 295                 300

Lys Ala Glu Phe His His Ser Ile Met Ser Gln Tyr Lys Leu Lys Ala
305                 310                 315                 320

Ser Ala Ile Ser Val Thr Val Leu Asn Val Ile Glu Gly Pro Val Phe
```

```
                    325                 330                 335

<210> SEQ ID NO 17
<211> LENGTH: 450
<212> TYPE: PRT
<213> ORGANISM: Artificial
<220> FEATURE:
<223> OTHER INFORMATION: Synthetic

<400> SEQUENCE: 17

Glu Trp Val Lys Phe Ala Lys Pro Cys Arg Glu Gly Glu Asp Asn Ser
1               5                   10                  15

Lys Arg Asn Pro Ile Ala Lys Ile Thr Ser Asp Tyr Gln Ala Thr Gln
            20                  25                  30

Lys Ile Thr Tyr Arg Ile Ser Gly Val Gly Ile Asp Gln Pro Pro Phe
        35                  40                  45

Gly Ile Phe Val Val Asp Lys Asn Thr Gly Asp Ile Asn Ile Thr Ala
    50                  55                  60

Ile Val Asp Arg Glu Glu Thr Pro Ser Phe Leu Ile Thr Cys Arg Ala
65                  70                  75                  80

Leu Asn Ala Gln Gly Leu Asp Val Glu Lys Pro Leu Ile Leu Thr Val
                85                  90                  95

Lys Ile Leu Asp Ile Asn Asp Asn Pro Pro Val Phe Ser Gln Gln Ile
            100                 105                 110

Phe Met Gly Glu Ile Glu Asn Ser Ala Ser Asn Ser Leu Val Met
        115                 120                 125

Ile Leu Asn Ala Thr Asp Ala Asp Glu Pro Asn His Leu Asn Ser Lys
    130                 135                 140

Ile Ala Phe Lys Ile Val Ser Gln Glu Pro Ala Gly Thr Pro Met Phe
145                 150                 155                 160

Leu Leu Ser Arg Asn Thr Gly Glu Val Arg Thr Leu Thr Asn Ser Leu
                165                 170                 175

Asp Arg Glu Gln Ala Ser Ser Tyr Arg Leu Val Val Ser Gly Ala Asp
            180                 185                 190

Lys Asp Gly Glu Gly Leu Ser Thr Gln Cys Glu Cys Asn Ile Lys Val
        195                 200                 205

Lys Asp Val Asn Asp Asn Phe Pro Met Phe Arg Asp Ser Gln Tyr Ser
    210                 215                 220

Ala Arg Ile Glu Glu Asn Ile Leu Ser Ser Glu Leu Leu Arg Phe Gln
225                 230                 235                 240

Val Thr Asp Leu Asp Glu Glu Tyr Thr Asp Asn Trp Leu Ala Val Tyr
                245                 250                 255

Phe Phe Thr Ser Gly Asn Glu Gly Asn Trp Phe Glu Ile Gln Thr Asp
            260                 265                 270

Pro Arg Thr Asn Glu Gly Ile Leu Lys Val Val Lys Ala Leu Asp Tyr
        275                 280                 285

Glu Gln Leu Gln Ser Val Lys Leu Ser Ile Ala Val Lys Asn Lys Ala
    290                 295                 300

Glu Phe His Gln Ser Val Ile Ser Arg Tyr Arg Val Gln Ser Thr Pro
305                 310                 315                 320

Val Thr Ile Gln Val Ile Asn Val Arg Glu Gly Ile Ala Phe Arg Pro
                325                 330                 335

Ala Ser Lys Thr Phe Thr Val Gln Lys Gly Ile Ser Ser Lys Lys Leu
            340                 345                 350

Val Asp Tyr Ile Leu Gly Thr Tyr Gln Ala Ile Asp Glu Asp Thr Asn
```

-continued

```
                355                 360                 365
Lys Ala Ala Ser Asn Val Lys Tyr Val Met Gly Arg Asn Asp Gly Gly
        370                 375                 380

Tyr Leu Met Ile Asp Ser Lys Thr Ala Glu Ile Lys Phe Val Lys Asn
385                 390                 395                 400

Met Asn Arg Asp Ser Thr Phe Ile Val Asn Lys Thr Ile Thr Ala Glu
                405                 410                 415

Val Leu Ala Ile Asp Glu Tyr Thr Gly Lys Thr Ser Thr Gly Thr Val
                420                 425                 430

Tyr Val Arg Val Pro Asp Phe Asn Asp Asn Cys Pro Thr Ala Val Leu
        435                 440                 445

Glu Lys
    450
```

UNITED STATES PATENT AND TRADEMARK OFFICE
CERTIFICATE OF CORRECTION

| | |
|---|---|
| PATENT NO. | : 11,266,717 B2 |
| APPLICATION NO. | : 16/324870 |
| DATED | : March 8, 2022 |
| INVENTOR(S) | : Quansheng Zhu |

It is certified that error appears in the above-identified patent and that said Letters Patent is hereby corrected as shown below:

In the Claims

In Column 79, Claim 22, Line 5, delete "11," and insert --1,--.

Signed and Sealed this
Twenty-sixth Day of July, 2022

*Katherine Kelly Vidal*

Katherine Kelly Vidal
*Director of the United States Patent and Trademark Office*